(12) United States Patent
Jaeschke et al.

(10) Patent No.: US 10,011,607 B2
(45) Date of Patent: Jul. 3, 2018

(54) ETHYNYL DERIVATIVES

(71) Applicant: Hoffmann-La Roche Inc., Little Falls, NJ (US)

(72) Inventors: Georg Jaeschke, Basel (CH); Fionn O'Hara, Basel (CH); Jean-Marc Plancher, Hagenthal-le-Bas (FR); Antonio Ricci, Birsfelden (CH); Daniel Rueher, Raedersdorf (FR); Eric Vieira, Frenkendorf (CH)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/867,097

(22) Filed: Jan. 10, 2018

(65) Prior Publication Data

US 2018/0127429 A1  May 10, 2018

Related U.S. Application Data

(63) Continuation of application No. PCT/EP2016/068359, filed on Feb. 8, 2016.

(30) Foreign Application Priority Data

Aug. 3, 2015 (EP) .................................... 15179550

(51) Int. Cl.
| | |
|---|---|
| *C07D 487/04* | (2006.01) |
| *A61P 25/00* | (2006.01) |
| *A61P 3/08* | (2006.01) |
| *A61P 25/22* | (2006.01) |
| *A61P 35/00* | (2006.01) |
| *A61P 25/16* | (2006.01) |
| *A61P 25/24* | (2006.01) |

(52) U.S. Cl.
CPC .............. *C07D 487/04* (2013.01); *A61P 3/08* (2018.01); *A61P 25/00* (2018.01); *A61P 25/16* (2018.01); *A61P 25/22* (2018.01); *A61P 25/24* (2018.01); *A61P 35/00* (2018.01); *C07B 2200/07* (2013.01); *C07B 2200/09* (2013.01)

(58) Field of Classification Search
CPC .................................................... C07D 487/04
USPC ........................................................ 514/249
See application file for complete search history.

(56) References Cited

FOREIGN PATENT DOCUMENTS

| WO | 2015/044075 A1 | 4/2015 |
|---|---|---|
| WO | 2015/104271 A1 | 7/2015 |
| WO | 2015/128307 A1 | 9/2015 |

OTHER PUBLICATIONS

ISR and Written Opinion of PCT/EP2016/068359, dated as of actual completion of the international search Sep. 6, 2016.

*Primary Examiner* — Kahsay Habte
(74) *Attorney, Agent, or Firm* — Brian L. Buckwalter

(57) ABSTRACT

The present invention relates to compounds of formula I

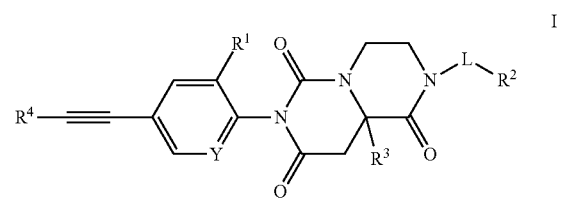

wherein
$R^1$ is hydrogen, F or Cl;
L is a bond or lower alkylene;
$R^2$ is —$(CH_2)_n$O-lower alkyl, lower alkyl substituted by halogen, —$(CH_2)_n$C(O)O-lower alkyl, phenyl substituted by lower alkyl or halogen, or is a 5 or 6-membered heteroaryl group, selected from pyridinyl, pyrimidinyl, pyridazinyl, thiazolyl, imidazolyl, pyrazolyl or triazolyl, which are optionally substituted by lower alkyl, halogen, lower alkoxy, =O, benzyloxy, cycloalkyloxy, hydroxy, cyano, lower alkyl substituted by halogen, or by —$(CH_2)_n$O-lower alkyl;
n is 1, 2 or 3;
$R^3$ is hydrogen, lower alkyl or —$(CH_2)_n$O-lower alkyl;
$R^4$ is phenyl, pyridinyl or pyrimidinyl, optionally substituted by F;
Y is CF or CCl;
or to a pharmaceutically acceptable salt or acid addition salt, to a racemic mixture, or to its corresponding enantiomer and/or optical isomer and/or stereoisomers thereof.
The compounds may be used for the treatment of Parkinson's disease, anxiety, emesis, obsessive compulsive disorder, autism, neuroprotection, cancer, depression and diabetes type 2.

10 Claims, 1 Drawing Sheet

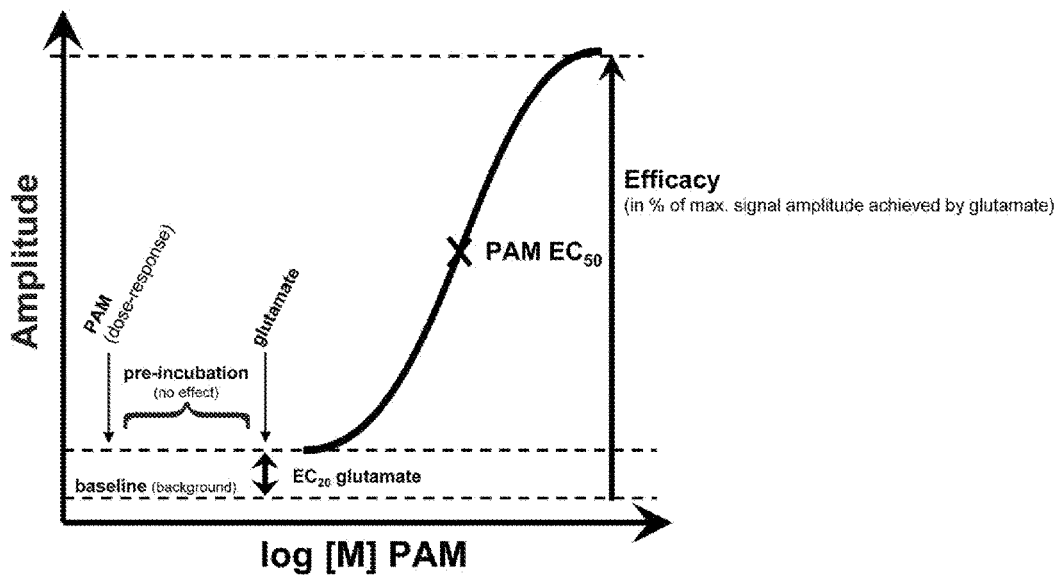

ETHYNYL DERIVATIVES

CROSS REFERENCE TO RELATED APPLICATIONS

This application is a continuation of International Application No. PCT/EP2016/068359 having an international filing date of Aug. 2, 2016 and which claims benefit under 35 U.S.C. § 119 to European Patent Application No. 15179550.7 having an international filing date of Aug. 3, 2015. The entire contents of both are incorporated herein by reference.

FIELD OF THE INVENTION

The present invention relates to organic of general formula I that are positive allosteric modulators (PAMs) of metabotropic glutamate receptor 4 (mGluR4). useful for therapy of diseases associated with aberrant functioning of the mGluR4 receptor.

BACKGROUND OF THE INVENTION

It has been surprisingly been found that the compounds of general formula I are positive allosteric modulators (PAMs) of metabotropic glutamate receptor 4 (mGluR4).

Metabotropic glutamate receptor 4 is a protein that in humans is encoded by the GRM4 gene. Together with GRM6, GRM7 and GRM8 it belongs to group III of the Metabotropic glutamate receptor family, and is negatively coupled to adenylate cyclase via activation of the Pop/ 02.05.2016

Gαi/o protein. It is expressed primarily on presynaptic terminals, functioning as an autoreceptor or heteroceptor and its activation leads to decreases in transmitter release from presynaptic terminals. mGluR4 is currently receiving much attention based primarily upon its unique distribution and the recent evidence that activation of this receptor plays key modulatory role in many CNS and non-CNS pathways (Celanire S, Campo B, *Expert Opinion in Drug Discovery*, 2012)

The similarity in the ligand binding domains of group III mGluRs creates a challenge for identifying selective orthosteric agonists of this receptor, although some progress has been made in this area. However, targeting positive allosteric modulators (PAMs) rather than orthosteric agonists provides a broader opportunity to identify molecules that are exclusively selective between mGluRs.

mGluR4 PAM is emerging as a promising target for the treatment of motor (and non motor) symptoms as well as a disease-modifying agent in Parkinson's disease through a non-dopaminergic approach.

Parkinson's disease is a progressive neurodegenerative disease that results in the loss of dopaminergic neurons in the substantia nigra (SN). One consequence of the depletion of dopamine in this disease is a series of movement disorders, including bradykinesia, akinesia, tremor, gait disorders and problems with balance. These motor disturbances form the hallmark of PD, although there are many other non-motor symptoms that are associated with the disease. Early in the course of the disease, PD symptoms are effectively treated by dopamine replacement or augmentation, with the use of dopamine D2 receptor agonists, levodopa or monoamine oxidase B inhibitors. However, as the disease progresses these agents become less effective in controlling motor symptoms. Additionally, their use is limited by the emergence of adverse effects including dopamine agonist-induced dyskinesias. Consequently, there remains a need for new approaches to the treatment of PD that improve the effectiveness of the control of motor symptoms.

Activation of metabotropic glutamate receptor 4 (mGluR4) has been proposed as a potential therapeutic approach to Parkinson's disease. A member of the group III mGluRs, mGluR4 is predominantly a presynaptic glutamate receptor that is expressed in several key locations in the basal ganglia circuits that control movement. Activation of mGluR4 with group III-preferring agonists decreases inhibitory and excitatory post synaptic potentials, presumably by decreasing the release of GABA and glutamate respectively.

The search for novel drugs that relieve motor symptoms of Parkinsonism whilst attenuating the ongoing degeneration of nigrostriatal neurons is of particular interest. Orthosteric mGluR4 agonist L-AP4 has demonstrated neuroprotective effects in a 6-OHDA rodent model of PD and first positive allosteric modulator (−)-PHCCC reduced nigrostriatal degeneration in mice treated with 1-Methyl-4-Phenyl-1,2,3,6-Tetrahydropyridine (MPTP). Those studies provide preclinical evidence suggesting that mGluR4 activators constitute a strong approach not only for symptomatic treatments of PD, but also potentially as disease modifiers.

The neuroprotective effect of selective mGluR4 agonists was also described in *Neuroreport*, 19(4), 475-8, 2008, *Proc. Natl. Acad. Sci, USA*, 100(23), 13668-73, 2003 and *J. Neurosci.* 26(27), 7222-9, 2006 and *Mol. Pharmacol.* 74(5), 1345-58, 2008.

Anxiety disorders are among the most prevalent psychiatric disorders in the world, and are co-morbid with Parkinson's disease (Prediger R, et al. *Neuropharmacology* 2012; 62:115-24). Excessive glutamatergic neurotransmission is one important feature of anxiety pathophysiology. Based on presynaptic localization of mGluR4 in brain areas involved in anxiety and mood disorders, and dampening excessive brain excitability, the mGluR4 activators may represent a new generation of anxiolytic therapeutics (*Eur. J. Pharmacol.*, 498(1-3), 153-6, 2004).

Addex has reported in 2010 that ADX88178 was active in two preclinical rodent models of anxiety: the marble burying test in mice and EPM in mice and rats. ADX88178 also displayed an anxiolytic-like profile in the rat EPM test after oral dosing.

mGluR4 modulators were also shown to exert anti-depressive actions (*Neuropharmacology*, 46(2), 151-9, 2004).

In addition, mGluR4 were also shown to be involved in glucagon secretion inhibition (*Diabetes*, 53(4), 998-1006, 2004). Therefore, orthosteric or positive allosteric modulators of mGluR4 have potential for the treatment of type 2 diabetes through its hypoglycemic effect.

Moreover, mGluR4 was shown to be expressed in prostate cancer cell-line (*Anticancer Res.* 29(1), 371-7, 2009) or colorectal carcinoma (*Cli. Cancer Research*, 11(9)3288-95, 2005). mGluR4 modulators may therefore have also potential role for the treatment of cancers.

Other proposed effects of mGluR4 PAM's can be expected for the treatment of emesis, obsessive compulsive disorder and autism.

SUMMARY OF THE INVENTION

Objects of the present invention are novel compounds of formula (I), their manufacture, medicaments based on a compound in accordance with the invention and their production as well as the use of compounds of formula (I)

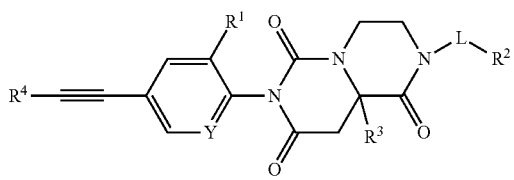

wherein
R¹ is hydrogen, F or Cl;
L is a bond or lower alkylene;
R² is —(CH₂)ₙO-lower alkyl, lower alkyl substituted by halogen, —(CH₂)ₙC(O)O-lower alkyl, phenyl substituted by lower alkyl or halogen, or is a 5 or 6-membered heteroaryl group, selected from pyridinyl, pyrimidinyl, pyridazinyl, thiazolyl, imidazolyl, pyrazolyl or triazolyl, which are optionally substituted by lower alkyl, halogen, lower alkoxy, =O, benzyloxy, cycloalkyloxy, hydroxy, cyano, lower alkyl substituted by halogen, or by —(CH₂)ₙO-lower alkyl;
n is 1, 2 or 3;
R³ is hydrogen, lower alkyl or —(CH₂)ₙO-lower alkyl;
R⁴ is phenyl, pyridinyl or pyrimidinyl, optionally substituted by F;
Y is CF or CCl;
or to a pharmaceutically acceptable salt or acid addition salt, to a racemic mixture, or to its corresponding enantiomer and/or optical isomer and/or stereoisomers thereof.

In another embodiment, the present inventions provide for pharmaceutical compositions comprising compounds of Formula I.

In yet another embodiment, the present invention provides for methods of treating disease associated with the mGluR4 receptors.

BRIEF DESCRIPTION OF THE DRAWINGS

FIG. 1: Illustrates the experimental outline for mGlu4 PAM Ca²⁺ mobilization screening assay and the determination of EC₅₀ and % E_max values. Positive signals obtained during the pre-incubation with the PAM test compounds (i.e. before application of an EC₂₀ concentration of L-AP4) were indicative of an agonistic activity, the absence of such signals were demonstrating the lack of agonistic activities. A depression of the signal observed after addition of the EC₂₀ concentration of L-AP4 was indicative of an inhibitory activity of the test compound.

DETAILED DESCRIPTION OF THE INVENTION

Compounds of formula I are distinguished by having valuable therapeutic properties. They can be used in the treatment or prevention of disorders, relating to allosteric modulators for the mGluR4 receptor.

The most preferred indications for compounds which are allosteric modulators for the mGluR4 receptor are Parkinson's disease, anxiety, emesis, obsessive compulsive disorder, autism, neuroprotection, cancer, depression and type 2 diabetes.

The present invention relates to compounds of formula I and to their pharmaceutically acceptable salts, to these compounds as pharmaceutically active substances, to the processes for their production as well as to the use in the treatment or prevention of disorders, relating to allosteric modulators for the mGluR4 receptor, such as Parkinson's disease, anxiety, emesis, obsessive compulsive disorder, anorexia, autism, neuroprotection, cancer, depression and diabetes type 2 and to pharmaceutical compositions containing the compounds of formula I.

A further object of the present invention is a method for the treatment or prophylaxis of Parkinson's disease, anxiety, emesis, obsessive compulsive disorder, autism, neuroprotection, cancer, depression and type 2 diabetes, which method comprises administering an effective amount of a compound of formula I to a mammal in need.

Furthermore, the invention includes all racemic mixtures, all their corresponding enantiomers and/or optical isomers.

The following definitions of the general terms used in the present description apply irrespective of whether the terms in question appear alone or in combination.

The following definitions of the general terms used in the present description apply irrespective of whether the terms in question appear alone or in combination.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

The term "lower alkyl substituted by halogen" denotes a lower alkyl group as defined above, wherein at least one hydrogen atom is replaced by a halogen atom.

The term "lower alkoxy" denotes a lower alkyl group as defined above, wherein this group is connected with an oxygen atom.

The term "lower alkylene" denotes linking groups like —CH₂— or —CH₂CH₂—.

The term "cycloalkyl" denotes a saturated ring containing from 3 to 7 carbon atoms, for example cyclopropyl, cyclobutyl, cyclopentyl, cyclohexyl or cycloheptyl.

The term "cycloalkoxy" denotes a cycloalkyl group, wherein this group is connected with an oxygen atom.

The term "halogen" denotes chlorine, iodine, fluorine and bromine.

The term "5 or 6-membered heteroaryl group, selected from pyridinyl, pyrimidinyl, pyridazinyl, thiazolyl, imidazolyl, pyrazolyl or triazolyl" denote the following groups;

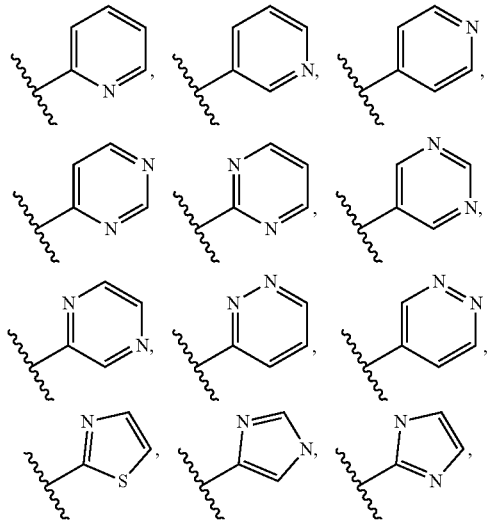

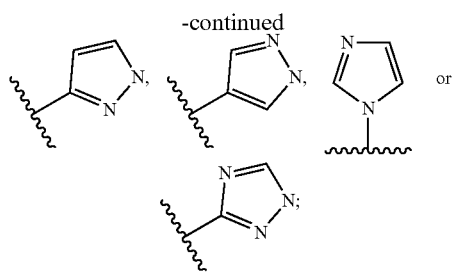

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention are compounds of formula Ia,

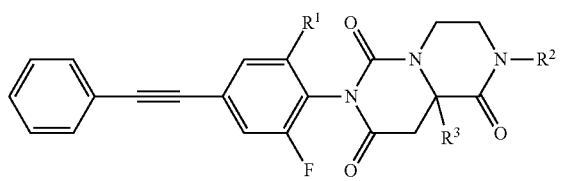

$R^1$ is F or Cl;
$R^2$ is —$(CH_2)_n$O-lower alkyl, lower alkyl substituted by halogen or —$(CH_2)_n$C(O)O-lower alkyl,
n is 1, 2 or 3;
$R^3$ hydrogen, lower alkyl or —$(CH_2)_n$O-lower alkyl;
or a pharmaceutically acceptable salt or acid addition salt, a racemic mixture, or its corresponding enantiomer and/or optical isomer and/or stereoisomers thereof, for example the following compounds:
(9aS)-7-[2,6-difluoro-4-(2-phenylethynyl)phenyl]-2-(2-methoxyethyl)-9a-methyl-4,9-dihydro-3H-pyrazino[1,2-c]pyrimidine-1,6,8-trione
(9aS)-7-[2,6-difluoro-4-(2-phenylethynyl)phenyl]-2-(3-methoxypropyl)-9a-methyl-4,9-dihydro-3H-pyrazino[1,2-c]pyrimidine-1,6,8-trione
(9aS)-7-[2,6-difluoro-4-(2-phenylethynyl)phenyl]-9a-methyl-2-(2,2,2-trifluoroethyl)-4,9-dihydro-3H-pyrazino[1,2-c]pyrimidine-1,6,8-trione or
Ethyl 4-[(9aS)-7-[2,6-difluoro-4-(2-phenylethynyl)phenyl]-9a-methyl-1,6,8-trioxo-4,9-dihydro-3H-pyrazino[1,2-c]pyrimidin-2-yl]butanoate.

One further object of the present invention are compounds of formula Ib

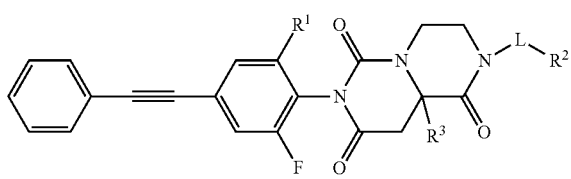

wherein
$R^1$ is F or Cl;
L is lower alkylene;
$R^2$ is phenyl substituted by lower alkyl or by halogen;
$R^3$ hydrogen, lower alkyl or —$(CH_2)_n$O-lower alkyl;
n is 1, 2 or 3;
or a pharmaceutically acceptable salt or acid addition salt, a racemic mixture, or its corresponding enantiomer and/or optical isomer and/or stereoisomers thereof, for example the following compounds
(9RS)-7-[2,6-difluoro-4-(2-phenylethynyl)phenyl]-9a-methyl-2-(m-tolylmethyl)-4,9-dihydro-3H-pyrazino[1,2-c]pyrimidine-1,6,8-trione
(9aRS)-7-[2,6-difluoro-4-(2-phenylethynyl)phenyl]-9a-methyl-2-(p-tolylmethyl)-4,9-dihydro-3H-pyrazino[1,2-c]pyrimidine-1,6,8-trione
(9aRS)-7-[2,6-difluoro-4-(2-phenylethynyl)phenyl]-9a-methyl-2-(o-tolylmethyl)-4,9-dihydro-3H-pyrazino[1,2-c]pyrimidine-1,6,8-trione
(9aRS)-7-[2,6-difluoro-4-(2-phenylethynyl)phenyl]-2-[(2,6-dimethylphenyl)methyl]-9a-methyl-4,9-dihydro-3H-pyrazino[1,2-c]pyrimidine-1,6,8-trione
(9aRS)-2-[(2-chlorophenyl)methyl]-7-[2,6-difluoro-4-(2-phenylethynyl)phenyl]-9a-methyl-4,9-dihydro-3H-pyrazino[1,2-c]pyrimidine-1,6,8-trione
(9aRS)-2-[(3-chlorophenyl)methyl]-7-[2,6-difluoro-4-(2-phenylethynyl)phenyl]-9a-methyl-4,9-dihydro-3H-pyrazino[1,2-c]pyrimidine-1,6,8-trione
(9aS)-7-[2,6-difluoro-4-(2-phenylethynyl)phenyl]-2-[(2-fluorophenyl)methyl]-9a-methyl-4,9-dihydro-3H-pyrazino[1,2-c]pyrimidine-1,6,8-trione
(9aS)-7-[2,6-difluoro-4-(2-phenylethynyl)phenyl]-2-[(3-fluorophenyl)methyl]-9a-methyl-4,9-dihydro-3H-pyrazino[1,2-c]pyrimidine-1,6,8-trione or
(9aS)-7-[2,6-difluoro-4-(2-phenylethynyl)phenyl]-2-[(4-fluorophenyl)methyl]-9a-methyl-4,9-dihydro-3H-pyrazino[1,2-c]pyrimidine-1,6,8-trione.

A further embodiment of the invention are compounds of formula Ic

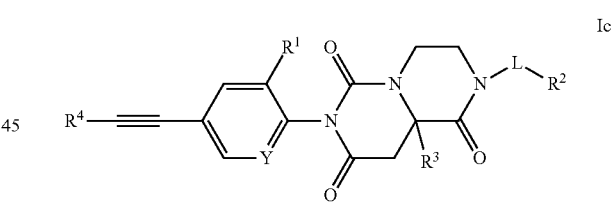

wherein
$R^1$ is hydrogen, F or Cl;
L is a bond or lower alkylene;
$R^2$ is a 5 or 6-membered heteroaryl group, selected from pyridinyl, pyrimidinyl, pyridazinyl, thiazolyl, imidazolyl, pyrazolyl or triazolyl, which are optionally substituted by lower alkyl, halogen, lower alkoxy, =O, benzyloxy, cycloalkyloxy, hydroxy, cyano, lower alkyl substituted by halogen, or by
$(CH_2)_n$O-lower alkyl;
n is 1, 2 or 3;
$R^3$ is hydrogen, lower alkyl or —$(CH_2)_n$O-lower alkyl;
$R^4$ is phenyl, optionally substituted by F;
Y is CF or CCl;
or a pharmaceutically acceptable salt or acid addition salt, a racemic mixture, or its corresponding enantiomer and/or optical isomer and/or stereoisomers thereof, for example the following compounds (9aRS)-7-[2,6-difluoro-4-(2-phenylethynyl)phenyl]-2-(3-pyridyl)-3,4,9,9a-tetrahydropyrazino[1,2-c]pyrimidine-1,6,8-trione (9aRS)-7-[2,6-difluoro-4-(2-phenylethynyl)phenyl]-2-pyrimidin-4-yl-3,4,9,9a-tetrahydropyrazino[1,2-c]pyrimidine-1,6,8-trione (9aRS)-7-[2,6-difluoro-4-(2-phenylethynyl)phenyl]-2-(2-pyridyl)-3,4,9,9a-tetrahydropyrazino[1,2-c]pyrimidine-1,6,8-trione (9aRS)-7-[2,6-difluoro-4-(2-phenylethynyl)phenyl]-9a-methyl-2-(2-pyridyl)-4,9-dihydro-3H-pyrazino[1,2-c]pyrimidine-1,6,8-trione (9aS)-7-[2,6-difluoro-4-(2-phenylethynyl)phenyl]-9a-methyl-2-(2-pyridyl)-4,9-dihydro-3H-pyrazino[1,2-c]pyrimidine-1,6,8-trione (9aRS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione (9aS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione (9aRS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione (9aS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione (9aRS)-7-[2,6-difluoro-4-(2-phenylethynyl)phenyl]-9a-methyl-2-(6-methyl-2-pyridyl)-4,9-dihydro-3H-pyrazino[1,2-c]pyrimidine-1,6,8-trione (9aRS)-7-[2,6-difluoro-4-(2-phenylethynyl)phenyl]-9a-methyl-2-(2-methyl-4-pyridyl)-4,9-dihydro-3H-pyrazino[1,2-c]pyrimidine-1,6,8-trione (9aRS)-7-(2,6-difluoro-4-(phenylethynyl)phenyl)-9a-methyl-2-(4-methylpyridin-2-yl)tetrahydro-1H-pyrazino[1,2-c]pyrimidine-1,6,8(2H,7H)-trione (9aS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione (9aRS)-7-[2,6-difluoro-4-(2-phenylethynyl)phenyl]-9a-methyl-2-(5-methyl-3-pyridyl)-4,9-dihydro-3H-pyrazino[1,2-c]pyrimidine-1,6,8-trione (9aS)-7-[2,6-difluoro-4-(2-phenylethynyl)phenyl]-9a-methyl-2-(5-methyl-3-pyridyl)-4,9-dihydro-3H-pyrazino[1,2-c]pyrimidine-1,6,8-trione (9aRS)-7-[2,6-difluoro-4-(2-phenylethynyl)phenyl]-9a-methyl-2-(6-methyl-3-pyridyl)-4,9-dihydro-3H-pyrazino[1,2-c]pyrimidine-1,6,8-trione (9aS)-7-[2,6-difluoro-4-(2-phenylethynyl)phenyl]-2-(3,5-dimethyl-4-pyridyl)-9a-methyl-4,9-dihydro-3H-pyrazino[1,2-c]pyrimidine-1,6,8-trione (9aRS)-2-(2-chloro-4-pyridyl)-7-[2,6-difluoro-4-(2-phenylethynyl)phenyl]-9a-methyl-4,9-dihydro-3H-pyrazino[1,2-c]pyrimidine-1,6,8-trione (9aS)-2-(2-chloro-4-pyridyl)-7-[2,6-difluoro-4-(2-phenylethynyl)phenyl]-9a-methyl-4,9-dihydro-3H-pyrazino[1,2-c]pyrimidine-1,6,8-trione (9aRS)-2-(6-chloro-3-pyridyl)-7-[2,6-difluoro-4-(2-phenylethynyl)phenyl]-9a-methyl-4,9-dihydro-3H-pyrazino[1,2-c]pyrimidine-1,6,8-trione (9aS)-2-(6-chloro-3-pyridyl)-7-[2,6-difluoro-4-(2-phenylethynyl)phenyl]-9a-methyl-4,9-dihydro-3H-pyrazino[1,2-c]pyrimidine-1,6,8-trione (9aRS)-7-[2,6-difluoro-4-(2-phenylethynyl)phenyl]-2-(6-methoxy-3-pyridyl)-9a-methyl-4,9-dihydro-3H-pyrazino[1,2-c]pyrimidine-1,6,8-trione (9aS)-7-[2,6-difluoro-4-(2-phenylethynyl)phenyl]-2-(6-methoxy-3-pyridyl)-9a-methyl-4,9-dihydro-3H-pyrazino[1,2-c]pyrimidine-1,6,8-trione (9aS)-7-[2,6-difluoro-4-(2-phenylethynyl)phenyl]-9a-methyl-2-(1-methyl-6-oxo-3-pyridyl)-4,9-dihydro-3H-pyrazino[1,2-c]pyrimidine-1,6,8-trione (9aRS)-7-[2,6-difluoro-4-(2-phenylethynyl)phenyl]-9a-methyl-2-pyrimidin-2-yl-4,9-dihydro-3H-pyrazino[1,2-c]pyrimidine-1,6,8-trione (9aRS)-7-[2,6-difluoro-4-(2-phenylethynyl)phenyl]-9a-methyl-2-pyrimidin-4-yl-4,9-dihydro-3H-pyrazino[1,2-c]pyrimidine-1,6,8-trione (9aS)-7-[2,6-difluoro-4-(2-phenylethynyl)phenyl]-9a-methyl-2-pyrimidin-4-yl-4,9-dihydro-3H-pyrazino[1,2-c]pyrimidine-1,6,8-trione (9aRS)-7-[2,6-difluoro-4-(2-phenylethynyl)phenyl]-9a-methyl-2-pyrimidin-5-yl-4,9-dihydro-3H-pyrazino[1,2-c]pyrimidine-1,6,8-trione (9aRS)-7-[2,6-difluoro-4-(2-phenylethynyl)phenyl]-2-(2,6-dimethylpyrimidin-4-yl)-9a-methyl-4,9-dihydro-3H-pyrazino[1,2-c]pyrimidine-1,6,8-trione (9aRS)-7-[2,6-difluoro-4-(2-phenylethynyl)phenyl]-9a-methyl-2-(2-methylpyrimidin-4-yl)-4,9-dihydro-3H-pyrazino[1,2-c]pyrimidine-1,6,8-trione (9aS)-7-[2,6-difluoro-4-(2-phenylethynyl)phenyl]-9a-methyl-2-(2-methylpyrimidin-4-yl)-4,9-dihydro-3H-pyrazino[1,2-c]pyrimidine-1,6,8-trione (9aRS)-7-[2,6-difluoro-4-(2-phenylethynyl)phenyl]-9a-methyl-2-pyrazin-2-yl-4,9-dihydro-3H-pyrazino[1,2-c]pyrimidine-1,6,8-trione (9aS)-7-[2,6-difluoro-4-(2-phenylethynyl)phenyl]-9a-methyl-2-pyrazin-2-yl-4,9-dihydro-3H-pyrazino[1,2-c]pyrimidine-1,6,8-trione (9aRS)-7-[2,6-difluoro-4-(2-phenylethynyl)phenyl]-9a-methyl-2-(6-methylpyrazin-2-yl)-4,9-dihydro-3H-pyrazino[1,2-c]pyrimidine-1,6,8-trione (9aS)-7-[2,6-difluoro-4-(2-phenylethynyl)phenyl]-9a-methyl-2-(6-methylpyrimidin-4-yl)-4,9-dihydro-3H-pyrazino[1,2-c]pyrimidine-1,6,8-trione (9aS)-7-[2,6-difluoro-4-(2-phenylethynyl)phenyl]-9a-methyl-2-(5-methylpyrimidin-4-yl)-4,9-dihydro-3H-pyrazino[1,2-c]pyrimidine-1,6,8-trione (9aS)-7-[2,6-difluoro-4-(2-phenylethynyl)phenyl]-2-(2-methoxypyrimidin-5-yl)-9a-methyl-4,9-dihydro-3H-pyrazino[1,2-c]pyrimidine-1,6,8-trione (9aS)-2-(2-tert-butoxypyrimidin-5-yl)-7-[2,6-difluoro-4-(2-phenylethynyl)phenyl]-9a-methyl-4,9-dihydro-3H-pyrazino[1,2-c]pyrimidine-1,6,8-trione (9aS or 9aR)-7-[2,6-difluoro-4-(2-phenylethynyl)phenyl]-2-(2-ethoxypyrimidin-5-yl)-9a-methyl-4,9-dihydro-3H-pyrazino[1,2-c]pyrimidine-1,6,8-trione (9aS)-7-[2,6-difluoro-4-(2-phenylethynyl)phenyl]-2-(2-isopropoxypyrimidin-5-yl)-9a-methyl-4,9-dihydro-3H-pyrazino[1,2-c]pyrimidine-1,6,8-trione (9aS)-2-(2-benzyloxypyrimidin-5-yl)-7-[2,6-difluoro-4-(2-phenylethynyl)phenyl]-9a-methyl-4,9-dihydro-3H-pyrazino[1,2-c]pyrimidine-1,6,8-trione (9aS)-7-[2,6-difluoro-4-(2-phenylethynyl)phenyl]-2-(2-hydroxypyrimidin-5-yl)-9a-methyl-4,9-dihydro-3H-pyrazino[1,2-c]pyrimidine-1,6,8-trione (9aS)-2-[2-(cyclopropoxy)pyrimidin-5-yl]-7-[2,6-difluoro-4-(2-phenylethynyl)phenyl]-9a-methyl-4,9-dihydro-3H-pyrazino[1,2-c]pyrimidine-1,6,8-trione (9aS)-7-[2,6-difluoro-4-(2-phenylethynyl)phenyl]-2-(5-methoxypyrazin-2-yl)-9a-methyl-4,9-dihydro-3H-pyrazino[1,2-c]pyrimidine-1,6,8-trione (9aS)-2-(5-benzyloxypyrazin-2-yl)-7-[2,6-difluoro-4-(2-phenylethynyl)phenyl]-9a-methyl-4,9-dihydro-3H-pyrazino[1,2-c]pyrimidine-1,6,8-trione (9aRS)-7-[2,6-difluoro-4-(2-phenylethynyl)phenyl]-9a-methyl-2-pyridazin-3-yl-4,9-dihydro-3H-pyrazino[1,2-c]pyrimidine-1,6,8-trione (9aS)-7-[2,6-difluoro-4-(2-phenylethynyl)phenyl]-9a-methyl-2-pyrazin-2-yl-4,9-dihydro-3H-pyrazino[1,2-c]pyrimidine-1,6,8-trione (9aRS)-7-[2,6-difluoro-4-(2-phenylethynyl)phenyl]-9a-methyl-2-(6-methylpyridazin-3-yl)-4,9-dihydro-3H-pyrazino[1,2-c]pyrimidine-1,6,8-trione (9aS)-7-[2,6-difluoro-4-(2-phenylethynyl)phenyl]-9a-methyl-2-(1-methyl-6-oxo-pyridazin-3-yl)-4,9-dihydro-3H-pyrazino[1,2-c]pyrimidine-1,6,8-trione (9aS)-7-[2,6-difluoro-4-(2-phenylethynyl)phenyl]-9a-methyl-2-pyridazin-4-yl-4,9-dihydro-3H-pyrazino[1,2-c]pyrimidine-1,6,8-trione (9aRS)-7-[2,6-difluoro-4-(2-phenylethynyl)phenyl]-9a-methyl-2-(1-methyl-6-oxo-pyridazin-4-yl)-4,9-dihydro-3H-pyrazino[1,2-c]pyrimidine-1,6,8-trione (9aRS)-7-[2,6-difluoro-4-(2-phenylethynyl)phenyl]-9a-methyl-2-thiazol-2-yl-4,9-dihydro-3H-pyrazino[1,2-c]pyrimidine-1,6,8-trione (9aRS)-7-[2,6-difluoro-4-(2-phenylethynyl)phenyl]-9a-methyl-2-(5-methylthiazol-2-yl)-4,9-dihydro-3H-pyrazino[1,2-c]pyrimidine-1,6,8-trione (9aRS)-7-[2,6-difluoro-4-(2-phenylethynyl)phenyl]-9a-methyl-2-(4-methylthiazol-2-yl)-4,9-dihydro-3H-pyrazino[1,2-c]pyrimidine-1,6,8-trione 2-[(9aRS)-7-[2,6-difluoro-4-(2-phenylethynyl)phenyl]-9a-methyl-1,6,8-trioxo-4,9-dihydro-3H-pyrazino[1,2-c]pyrimidin-2-yl]thiazole-4-carbonitrile (9aRS)-7-[2,6-difluoro-4-(2-phenylethynyl)phenyl]-9a-methyl-2-[4-(trifluoromethyl)thiazol-2-yl]-4,9-dihydro-3H-pyrazino[1,2-c]pyrimidine-1,6,8-trione (9aRS)-7-[2,6-difluoro-4-(2-phenylethynyl)phenyl]-9a-methyl-2-[5-(trifluoromethyl)thiazol-2-yl]-4,9-dihydro-3H-pyrazino[1,2-c]pyrimidine-1,6,8-trione (9aRS)-7-[2,6-difluoro-4-(2-phenylethynyl)phenyl]-9a-methyl-2-(1-methylimidazol-4-yl)-4,9-dihydro-3H-pyrazino[1,2-c]pyrimidine-1,6,8-trione (9aRS)-7-[2,6-difluoro-4-(2-phenylethynyl)phenyl]-2-(1,4-dimethylimidazol-2-yl)-9a-methyl-4,9-dihydro-3H-pyrazino[1,2-c]pyrimidine-1,6,8-trione (9aRS)-7-[2,6-difluoro-4-(2-phenylethynyl)phenyl]-2-(1,2-dimethylimidazol-4-yl)-9a-methyl-4,9-dihydro-3H-pyrazino[1,2-c]pyrimidine-1,6,8-trione (9aS)-7-[2,6-difluoro-4-(2-phenylethynyl)phenyl]-9a-methyl-2-[2-methyl-1-(2,2,2-trifluoroethyl)imidazol-4-yl]-4,9-dihydro-3H-pyrazino[1,2-c]pyrimidine-1,6,8-trione (9aRS)-7-[2,6-difluoro-4-(2-phenylethynyl)phenyl]-9a-methyl-2-(1-methylpyrazol-3-yl)-4,9-dihydro-3H-pyrazino[1,2-c]pyrimidine-1,6,8-trione (9aS)-7-[2,6-difluoro-4-(2-phenylethynyl)phenyl]-9a-methyl-2-(1-methylpyrazol-3-yl)-4,9-dihydro-3H-pyrazino[1,2-c]pyrimidine-1,6,8-trione (9aRS)-7-[2,6-difluoro-4-(2-phenylethynyl)phenyl]-9a-methyl-2-(2-methylpyrazol-3-yl)-4,9-dihydro-3H-pyrazino[1,2-c]pyrimidine-1,6,8-trione (9aS)-7-[2,6-difluoro-4-(2-phenylethynyl)phenyl]-9a-methyl-2-(2-methylpyrazol-3-yl)-4,9-dihydro-3H-pyrazino[1,2-c]pyrimidine-1,6,8-trione (9aRS)-7-[2,6-difluoro-4-(2-phenylethynyl)phenyl]-2-(2,5-dimethylpyrazol-3-yl)-9a-methyl-4,9-dihydro-3H-pyrazino[1,2-c]pyrimidine-1,6,8-trione (9aRS)-7-[2,6-difluoro-4-(2-phenylethynyl)phenyl]-9a-methyl-2-(1-methylpyrazol-4-yl)-4,9-dihydro-3H-pyrazino[1,2-c]pyrimidine-1,6,8-trione (9aS)-7-[2,6-difluoro-4-(2-phenylethynyl)phenyl]-9a-methyl-2-(1-methylpyrazol-4-yl)-4,9-dihydro-3H-pyrazino[1,2-c]pyrimidine-1,6,8-trione (9aS)-7-[2,6-difluoro-4-(2-phenylethynyl)phenyl]-2-(1-ethylpyrazol-4-yl)-9a-methyl-4,9-dihydro-3H-pyrazino[1,2-c]pyrimidine-1,6,8-trione (9aS)-7-[2,6-difluoro-4-(2-phenylethynyl)phenyl]-2-(1-isopropylpyrazol-4-yl)-9a-methyl-4,9-dihydro-3H-pyrazino[1,2-c]pyrimidine-1,6,8-trione (9aS)-7-[2,6-difluoro-4-(2-phenylethynyl)phenyl]-9a-methyl-2-(1H-pyrazol-4-yl)-4,9-dihydro-3H-pyrazino[1,2-c]pyrimidine-1,6,8-trione (9aS)-7-[2,6-difluoro-4-(2-phenylethynyl)phenyl]-2-[1-(3-methoxypropyl)pyrazol-4-yl]-9a-methyl-4,9-dihydro-3H-pyrazino[1,2-c]pyrimidine-1,6,8-trione (9aS)-7-[2,6-difluoro-4-(2-phenylethynyl)phenyl]-9a-methyl-2-(1-methyl-1,2,4-triazol-3-yl)-4,9-dihydro-3H-pyrazino[1,2-c]pyrimidine-1,6,8-trione (9aRS)-7-[2-chloro-6-fluoro-4-(2-phenylethynyl)phenyl]-9a-methyl-2-(3-pyridyl)-4,9-dihydro-3H-pyrazino[1,2-c]pyrimidine-1,6,8-trione (9aRS)-7-[2-chloro-6-fluoro-4-(2-phenylethynyl)phenyl]-9a-methyl-2-(4-pyridyl)-4,9-dihydro-3H-pyrazino[1,2-c]pyrimidine-1,6,8-trione (9aRS)-7-[2-chloro-6-fluoro-4-(2-phenylethynyl)phenyl]-9a-methyl-2-(2-pyridyl)-4,9-dihydro-3H-pyrazino[1,2-c]pyrimidine-1,6,8-trione (9aRS)-7-[2-chloro-6-fluoro-4-(2-phenylethynyl)phenyl]-9a-methyl-2-(4-pyridyl)-4,9-dihydro-3H-pyrazino[1,2-c]pyrimidine-1,6,8-trione (9aS)-7-[2-chloro-6-fluoro-4-(2-phenylethynyl)phenyl]-9a-methyl-2-(4-pyridyl)-4,9-dihydro-3H-pyrazino[1,2-c]pyrimidine-1,6,8-trione (9aRS)-7-[2,6-difluoro-4-(2-phenylethynyl)phenyl]-9a-methyl-2-(2-pyridylmethyl)-4,9-dihydro-3H-pyrazino[1,2-c]pyrimidine-1,6,8-trione (9aRS)-7-[2,6-difluoro-4-(2-phenylethynyl)phenyl]-9a-methyl-2-(3-pyridylmethyl)-4,9-dihydro-3H-pyrazino[1,2-c]pyrimidine-1,6,8-trione (9aRS)-7-[2,6-difluoro-4-(2-phenylethynyl)phenyl]-9a-methyl-2-(4-pyridylmethyl)-4,9-dihydro-3H-pyrazino[1,2-c]pyrimidine-1,6,8-trione (9aRS)-7-[2,6-difluoro-4-(2-phenylethynyl)phenyl]-9a-methyl-2-(pyrimidin-4-ylmethyl)-4,9-dihydro-3H-pyrazino[1,2-c]pyrimidine-1,6,8-trione (9aRS)-7-[2,6-difluoro-4-(2-phenylethynyl)phenyl]-9a-methyl-2-[(1-methylpyrazol-4-yl)methyl]-4,9-dihydro-3H-pyrazino[1,2-c]pyrimidine-1,6,8-trione (9aS)-7-[2,6-difluoro-4-(2-phenylethynyl)phenyl]-9a-methyl-2-[(2-methylpyrazol-3-yl)methyl]-4,9-dihydro-3H-pyrazino[1,2-c]pyrimidine-1,6,8-trione (9aS)-7-[2,6-difluoro-4-(2-phenylethynyl)phenyl]-2-(2-imidazol-1-ylethyl)-9a-methyl-4,9-dihydro-3H-pyrazino[1,2-c]pyrimidine-1,6,8-trione (9aS)-7-[2,6-difluoro-4-(2-phenylethynyl)phenyl]-9a-methyl-2-[2-(2-methylimidazol-1-yl)ethyl]-4,9-dihydro-3H-pyrazino[1,2-c]pyrimidine-1,6,8-trione (9aS)-7-[2,6-difluoro-4-(2-phenylethynyl)phenyl]-9a-methyl-2-[2-(2-methylpyrazol-3-yl)ethyl]-4,9-dihydro-3H-pyrazino[1,2-c]pyrimidine-1,6,8-trione (9aS)-7-[2,6-difluoro-4-(2-phenylethynyl)phenyl]-9a-methyl-2-[2-(1-methylpyrazol-4-yl)ethyl]-4,9-dihydro-3H-pyrazino[1,2-c]pyrimidine-1,6,8-trione (9aRS)-7-[2,6-difluoro-4-(2-phenylethynyl)phenyl]-9a-(methoxymethyl)-2-(3-pyridyl)-4,9-dihydro-3H-pyrazino[1,2-c]pyrimidine-1,6,8-trione
(9aR)-7-[2,6-difluoro-4-(2-phenylethynyl)phenyl]-9a-(methoxymethyl)-2-(3-pyridyl)-4,9-dihydro-3H-pyrazino[1,2-c]pyrimidine-1,6,8-trione
(9aRS)-7-[2,6-difluoro-4-(2-phenylethynyl)phenyl]-9a-(methoxymethyl)-2-(1-methylpyrazol-4-yl)-4,9-dihydro-3H-pyrazino[1,2-c]pyrimidine-1,6,8-trione
(9aR)-7-[2,6-difluoro-4-(2-phenylethynyl)phenyl]-9a-(methoxymethyl)-2-(1-methylpyrazol-4-yl)-4,9-dihydro-3H-pyrazino[1,2-c]pyrimidine-1,6,8-trione
(9aS)-7-[2,6-difluoro-4-(2-phenylethynyl)phenyl]-9a-ethyl-2-(3-pyridyl)-4,9-dihydro-3H-pyrazino[1,2-c]pyrimidine-1,6,8-trione
(9aS)-7-[2,6-difluoro-4-(2-phenylethynyl)phenyl]-9a-ethyl-2-(1-methylpyrazol-4-yl)-4,9-dihydro-3H-pyrazino[1,2-c]pyrimidine-1,6,8-trione
(9aRS)-7-[2-fluoro-4-(2-phenylethynyl)phenyl]-9a-methyl-2-(3-pyridyl)-4,9-dihydro-3H-pyrazino[1,2-c]pyrimidine-1,6,8-trione
(9aS)-7-[2,6-difluoro-4-[2-(2-fluorophenyl)ethynyl]phenyl]-9a-methyl-2-(3-pyridyl)-4,9-dihydro-3H-pyrazino[1,2-c]pyrimidine-1,6,8-trione
(9aS)-7-[2,6-difluoro-4-[2-(2-fluorophenyl)ethynyl]phenyl]-9a-methyl-2-pyrimidin-4-yl-4,9-dihydro-3H-pyrazino[1,2-c]pyrimidine-1,6,8-trione
(9aS)-7-[2,6-difluoro-4-[2-(2-fluorophenyl)ethynyl]phenyl]-9a-methyl-2-(1-methylpyrazol-4-yl)-4,9-dihydro-3H-pyrazino[1,2-c]pyrimidine-1,6,8-trione or
(9aS)-7-[2-chloro-4-(2-phenylethynyl)phenyl]-9a-methyl-2-(1-methylpyrazol-4-yl)-4,9-dihydro-3H-pyrazino[1,2-c]pyrimidine-1,6,8-trione.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variant described below, which process comprises a) reacting a compound of formula IV

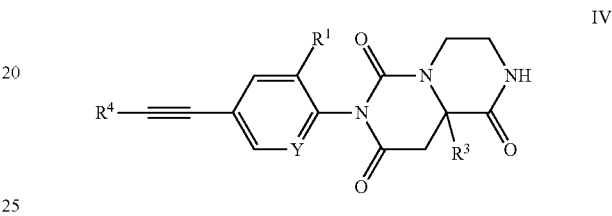

with a compound of formula XLR², wherein X is halogen, to a compound of formula I

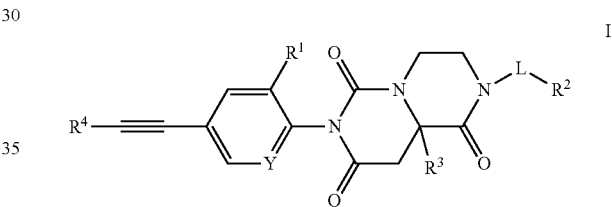

and, if desired, converting the compounds obtained into pharmaceutically acceptable acid addition salts.

The preparation of compounds of formula I is further described in more detail in schemes 1 and 2 and in the examples 1-112.

Scheme 1

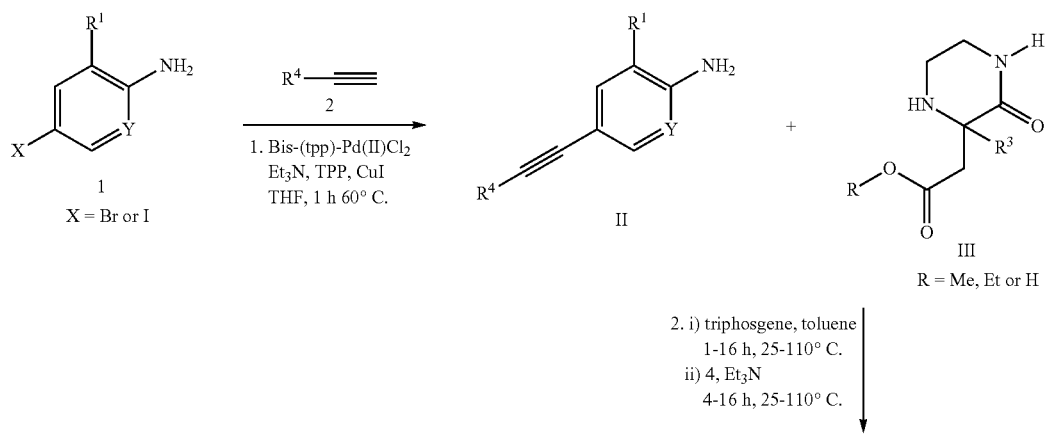

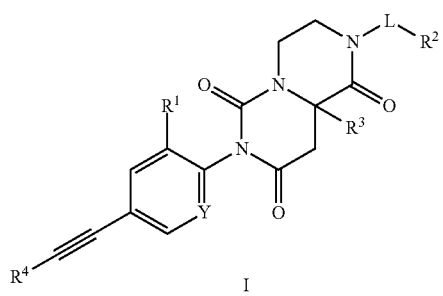
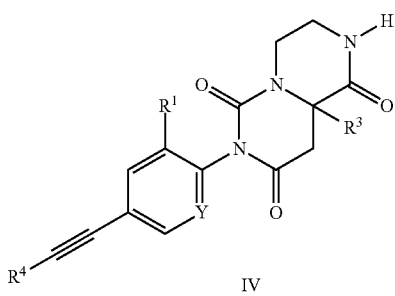

A substituted pyrimidine-2,6-dione compound of general formula I can be obtained for example by Sonogashira coupling of an appropriately substituted aniline or aminopyridine 1 with a phenyl-acetylene 2 to yield the desired ethynyl compounds of formula II. Reacting ethynyl compounds of formula II with an appropriately substituted aminoester or amino acid of formula III with phosgene or a phosgene equivalent such as triphosgene or carbonyldiimidazole (CDI) in presence or absence of a base such as triethylamine in a solvent such as toluene or dioxane forms the desired ethynyl-phenyl, ethynyl-pyridyl or ethynyl-pyrimidinyl substituted imidazolidine-2,4-dione compounds of general formula IV (scheme 1). The two steps involving reaction of intermediates II and III to form a urea derivative which then reacts with the ester group to form the pyrimidine dione of formula IV can be conducted in a one pot two step reaction or the two steps can be performed sequentially in normal or reverse order (amide formation followed by urea formation) depending on the starting materials available. Introduction of the L-R² substituent can also be realized at various points in the synthetic sequence via functionalization of the corresponding intermediates III or IV.

The R⁴ substituent can also be introduced by reacting a compound of formula I with trimethylsilylacetylene followed by a second Sonogashira reaction in presence of fluoride with an aryl iodide or bromide R⁴—X to yield the corresponding R⁴ substituted acetylene derivative II. Generally speaking, the sequence of steps used to synthesize the compounds of formula I can also be further modified in certain cases. It is also possible to separate the racemic mixtures of compounds of formula I, III or IV on a chiral stationary phase in order to yield the corresponding optically pure enantiomers. The intermediate of formula IV can also be synthesized for example using the following method (scheme 2):

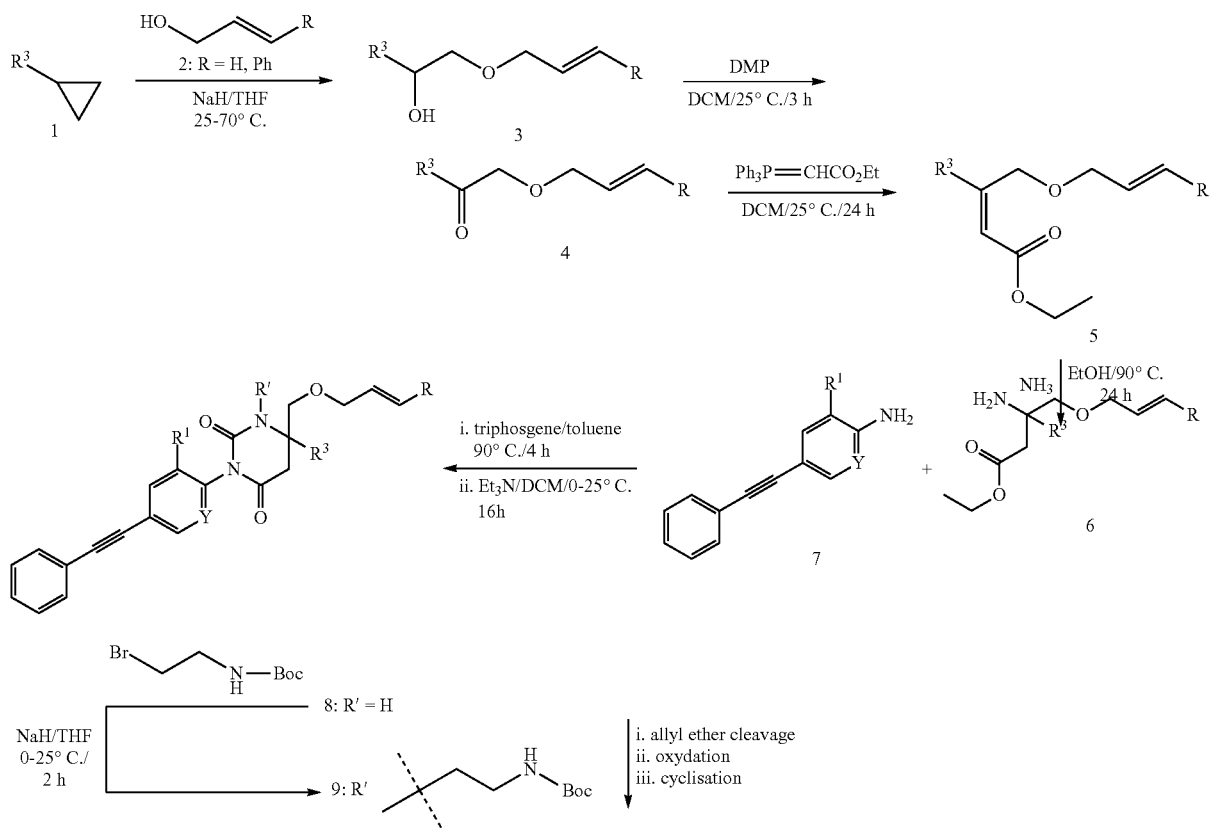

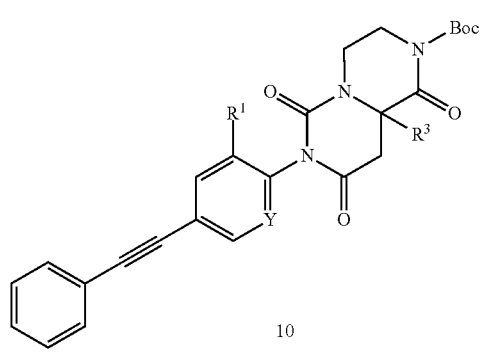

10

-continued

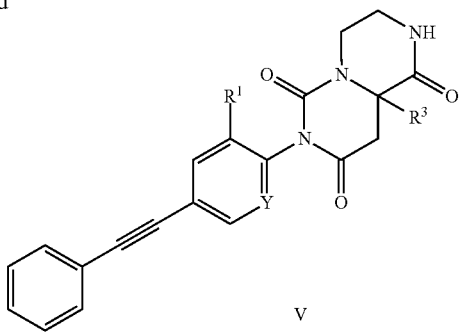

V

An appropriately substituted epoxide (1) is ring-opened under basic or acidic conditions with an alcohol (2) which has a protecting group moiety attached such as allyl- or cinnamyl-alcohol. The secondary alcohol formed (3) is oxidized to the corresponding ketone 4 which is then transformed to the corresponding α,β-unsaturated ester 5 using Wittig or Wittig-Horner conditions. The ester is then treated with ammonia to yield the Michael-addition product 6 which is cyclized using the same conditions mentioned before to yield compound 8. The urea nitrogen is then alkylated using a suitable protected bromoethylamino-derivative to yield the alkylated compound 9. Deprotection of the alcohol followed by oxidation to the carboxylic acid leads to cyclised product (10) which is deprotected to yield intermediate V which can then be further transformed to form compounds of formula I.

Biological Assay and Data

Determination of $EC_{50}$ Values Using a Ca2+ Mobilization In Vitro Assay on Recombinant Human mGlu4 Expressed in HEK293 Cells:

A monoclonal HEK-293 cell line stably transfected with a cDNA encoding for the human mGlu4 receptor was generated; for the work with mGlu4 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist (2S)-2-amino-4-phosphonobutanoic acid (L-AP4) was added to the cells at a concentration corresponding to $EC_{20}$ with on-line recording of fluorescence; in order to account for day-to-day variations in the responsiveness of cells, the $EC_{20}$ of L-AP4 was determined immediately ahead of each experiment by recording of a full dose-response curve of L-AP4.

Responses were measured as peak increase in fluorescence minus basal (i.e. fluorescence without addition of L-AP4), normalized to the maximal stimulatory effect obtained with saturating concentrations of L-AP4. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (drug concentration at which 50% of the maximal receptor activation was achieved), the Hill coefficient as well as the maximal response in % of the maximal stimulatory effect obtained with saturating concentrations of L-AP4 were calculated (see FIG. 1).

List of Examples and data:

| Ex. | Structure | Name | $EC_{50}$ (nM) mGlu4PAM | Eff. (%) |
|---|---|---|---|---|
| 1 | 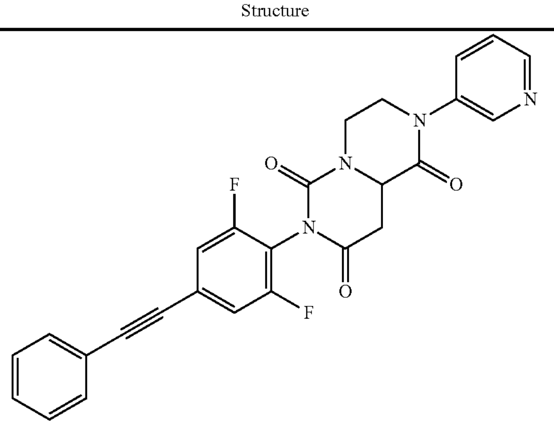 | (9aRS)-7-[2,6-difluoro-4-(2-phenylethynyl)phenyl]-2-(3-pyridyl)-3,4,9,9a-tetrahydropyrazino[1,2-c]pyrimidine-1,6,8-trione | 224 | 105 |

-continued

List of Examples and data:

| Ex. | Structure | Name | EC$_{50}$ (nM) mGlu4PAM | Eff. (%) |
|---|---|---|---|---|
| 2 | 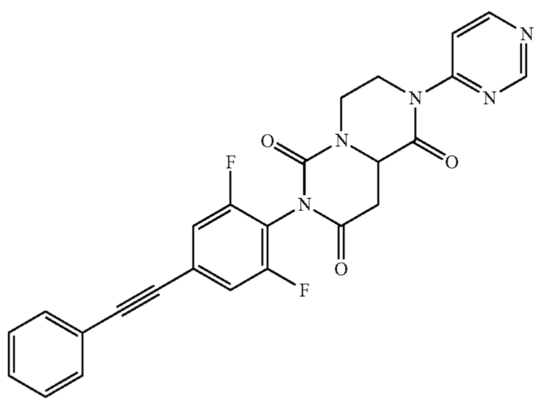 [SMILES: O=C1C2CC(=O)N(c3c(F)cc(C#Cc4ccccc4)cc3F)C(=O)N2CCN1c1ccncn1] | (9aRS)-7-[2,6-difluoro-4-(2-phenylethynyl)phenyl]-2-pyrimidin-4-yl-3,4,9,9a-tetrahydro-pyrazino[1,2-c]pyrimidine-1,6,8-trione | 85 | 88 |
| 3 | 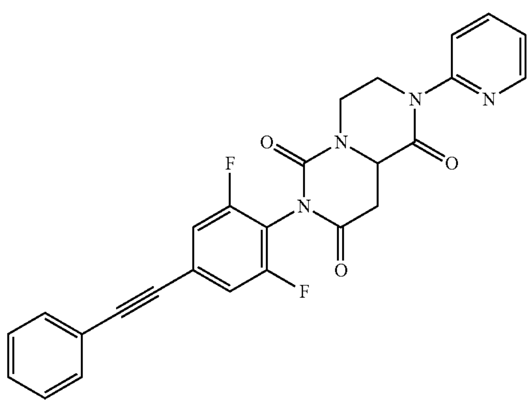 [SMILES: O=C1C2CC(=O)N(c3c(F)cc(C#Cc4ccccc4)cc3F)C(=O)N2CCN1c1ccccn1] | (9aRS)-7-[2,6-difluoro-4-(2-phenylethynyl)phenyl]-2-(2-pyridyl)-3,4,9,9a-tetrahydropyrazino[1,2-c]pyrimidine-1,6,8-trione | 235 | 116 |
| 4 | 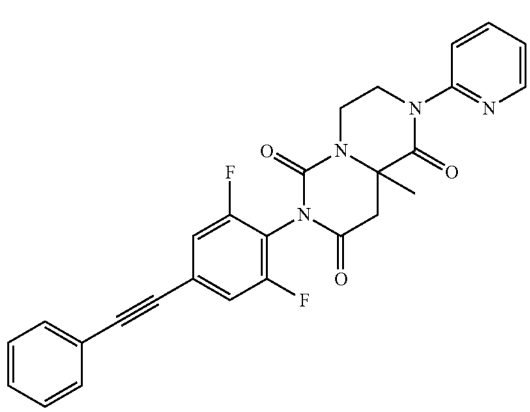 [SMILES: CC12CC(=O)N(c3c(F)cc(C#Cc4ccccc4)cc3F)C(=O)N1CCN(c1ccccn1)C2=O] | (9aRS)-7-(2,6-difluoro-4-(phenylethynyl)phenyl)-9a-methyl-2-(pyridin-2-yl)tetrahydro-1H-pyrazino[1,2-c]pyrimidine-1,6,8(2H,7H)-trione | 119 | 110 |

-continued

List of Examples and data:

| Ex. | Structure | Name | EC$_{50}$ (nM) mGlu4PAM | Eff. (%) |
|---|---|---|---|---|
| 5 | 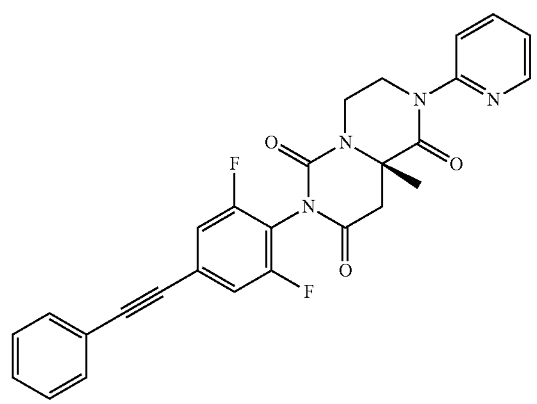 [SMILES: C[C@@]12CC(=O)N(c3c(F)cc(C#Cc4ccccc4)cc3F)C(=O)N1CCN(c1ccccn1)C2=O] | (9aS)-7-[2,6-difluoro-4-(2-phenylethynyl)phenyl]-9a-methyl-2-(2-pyridyl)-4,9-dihydro-3H-pyrazino[1,2-c]pyrimidine-1,6,8-trione | 46 | 92 |
| 6 | 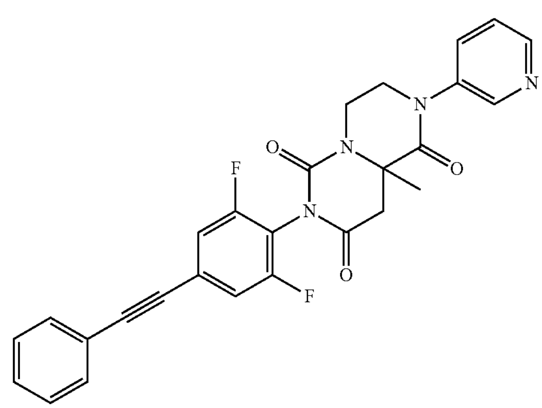 [SMILES: CC12CC(=O)N(c3c(F)cc(C#Cc4ccccc4)cc3F)C(=O)N1CCN(c1cccnc1)C2=O] | (9aRS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione | 118 | 122 |
| 7 | 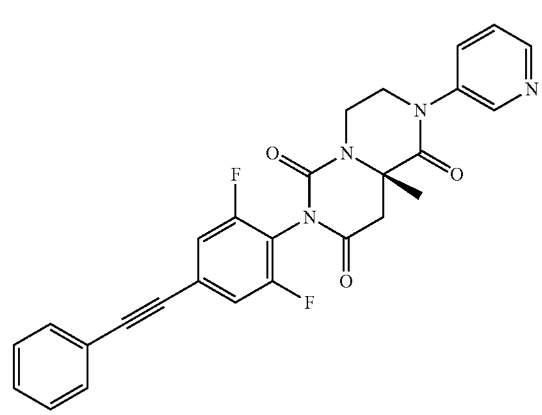 [SMILES: C[C@@]12CC(=O)N(c3c(F)cc(C#Cc4ccccc4)cc3F)C(=O)N1CCN(c1cccnc1)C2=O] | (9aS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione | 73 | 126 |

-continued

List of Examples and data:

| Ex. | Structure | Name | EC$_{50}$ (nM) mGlu4PAM | Eff. (%) |
|---|---|---|---|---|
| 8 | 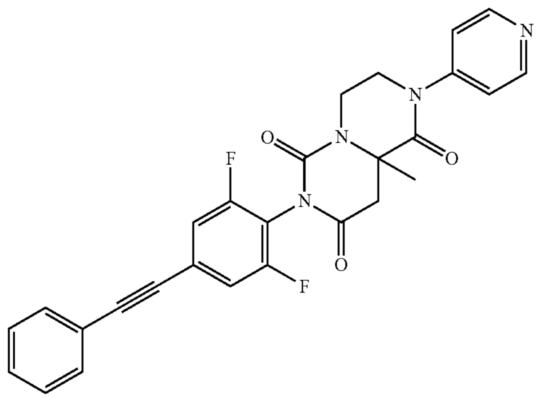 [SMILES: CC12CC(=O)N(c3c(F)cc(C#Cc4ccccc4)cc3F)C(=O)N1CCN(c1ccncc1)C2=O] | (9aRS)-7-[2,6-difluoro-4-(2-phenylethynyl)phenyl]-9a-methyl-2-(4-pyridyl)-4,9-dihydro-3H-pyrazino[1,2-c]pyrimidine-1,6,8-trione | 129 | 118 |
| 9 | 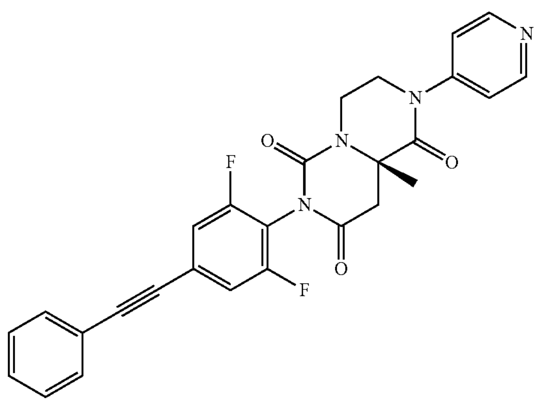 [SMILES: C[C@@]12CC(=O)N(c3c(F)cc(C#Cc4ccccc4)cc3F)C(=O)N1CCN(c1ccncc1)C2=O] | (9aS)-7-[2,6-difluoro-4-(2-phenylethynyl)phenyl]-9a-methyl-2-(4-pyridyl)-4,9-dihydro-3H-pyrazino[1,2-c]pyrimidine-1,6,8-trione | 29 | 85 |
| 10 | 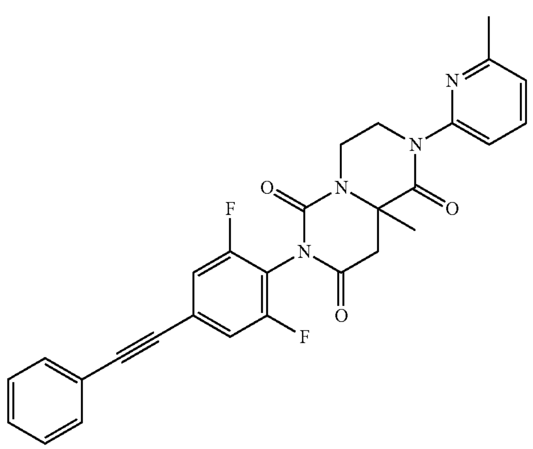 [SMILES: Cc1cccc(N2CCN3C(=O)N(c4c(F)cc(C#Cc5ccccc5)cc4F)C(=O)CC3(C)C2=O)n1] | (9aRS)-7-(2,6-difluoro-4-(phenylethynyl)phenyl)-9a-methyl-2-(6-methylpyridin-2-yl)tetrahydro-1H-pyrazino[1,2-c]pyrimidine-1,6,8(2H,7H)-trione | 163 | 127 |

-continued

List of Examples and data:

| Ex. | Structure | Name | EC$_{50}$ (nM) mGlu4PAM | Eff. (%) |
|---|---|---|---|---|
| 11 | 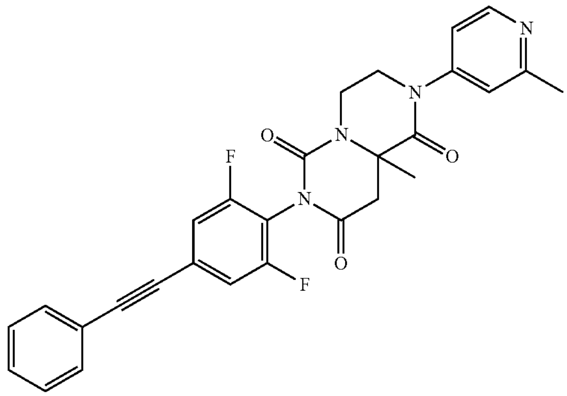 [SMILES: Cc1cc(N2CCN3C(=O)N(c4c(F)cc(C#Cc5ccccc5)cc4F)C(=O)CC3(C)C2=O)ccn1] | (9aRS)-7-[2,6-difluoro-4-(2-phenylethynyl)phenyl]-9a-methyl-2-(2-methyl-4-pyridyl)-4,9-dihydro-3H-pyrazino[1,2-c]pyrimidine-1,6,8-trione | 214 | 119 |
| 12 | 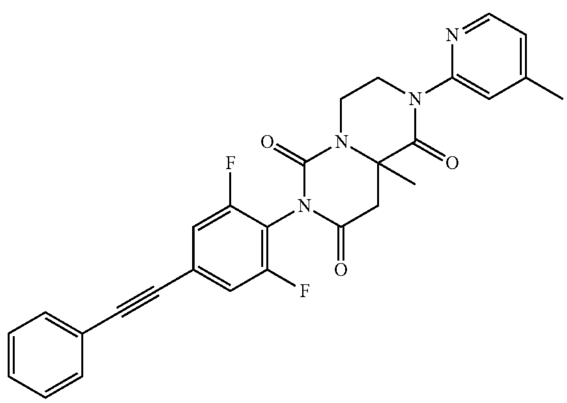 | (9aRS)-7-(2,6-difluoro-4-(phenylethynyl)phenyl)-9a-methyl-2-(4-methylpyridin-2-yl)tetrahydro-1H-pyrazino[1,2-c]pyrimidine-1,6,8(2H,7H)-trione | 131 | 126 |
| 13 | Chiral | (9aS)-7-[2,6-difluoro-4-(2-phenylethynyl)phenyl]-9a-methyl-2-(4-methyl-2-pyridyl)-4,9-dihydro-3H-pyrazino[1,2-c]pyrimidine-1,6,8-trione | 131 | 148 |

-continued

List of Examples and data:

| Ex. | Structure | Name | EC$_{50}$ (nM) mGlu4PAM | Eff. (%) |
|---|---|---|---|---|
| 14 | 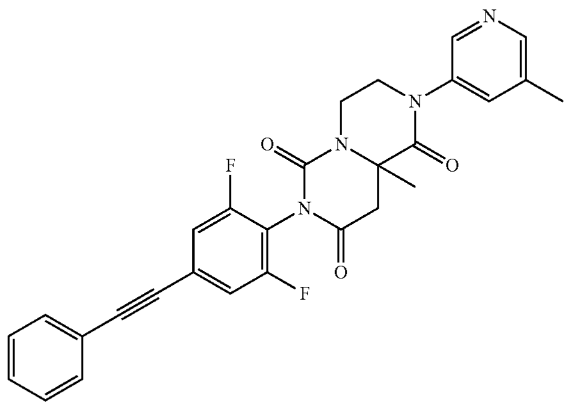 [SMILES: Cc1cncc(N2CCN3C(=O)N(c4c(F)cc(C#Cc5ccccc5)cc4F)C(=O)CC3(C)C2=O)c1] | (9aRS)-7-(2,6-difluoro-4-(phenylethynyl)phenyl)-9a-methyl-2-(5-methylpyridin-3-yl)tetrahydro-1H-pyrazino[1,2-c]pyrimidine-1,6,8(2H,7H)-trione | 105 | 129 |
| 15 | 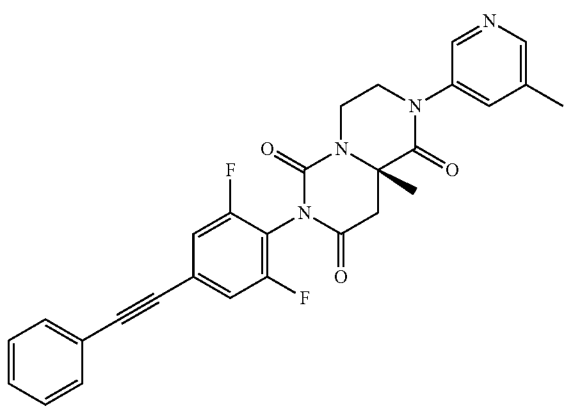 [SMILES: Cc1cncc(N2CCN3C(=O)N(c4c(F)cc(C#Cc5ccccc5)cc4F)C(=O)C[C@@]3(C)C2=O)c1] | (9aS)-7-(2,6-difluoro-4-(phenylethynyl)phenyl)-9a-methyl-2-(5-methylpyridin-3-yl)tetrahydro-1H-pyrazino[1,2-c]pyrimidine-1,6,8(2H,7H)-trione | 152 | 90 |
| 16 | 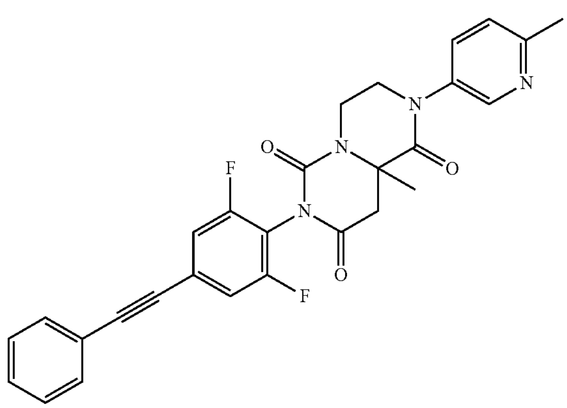 [SMILES: Cc1ccc(N2CCN3C(=O)N(c4c(F)cc(C#Cc5ccccc5)cc4F)C(=O)CC3(C)C2=O)cn1] | (9aRS)-7-(2,6-difluoro-4-(phenylethynyl)phenyl)-9a-methyl-2-(6-methylpyridin-3-yl)tetrahydro-1H-pyrazino[1,2-c]pyrimidine-1,6,8(2H,7H)-trione | 298 | 125 |

-continued

List of Examples and data:

| Ex. | Structure | Name | EC$_{50}$ (nM) mGlu4PAM | Eff. (%) |
|---|---|---|---|---|
| 17 | 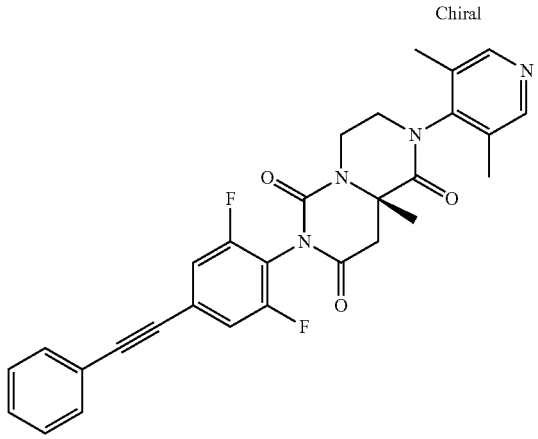 [SMILES: Cc1cncc(C)c1N1CCN2C(=O)N(c3c(F)cc(C#Cc4ccccc4)cc3F)C(=O)C[C@@]2(C)C1=O] Chiral | (9aS)-7-[2,6-difluoro-4-(2-phenylethynyl)phenyl]-2-(3,5-dimethyl-4-pyridyl)-9a-methyl-4,9-dihydro-3H-pyrazino[1,2-c]pyrimidine-1,6,8-trione | 201 | 136 |
| 18 | 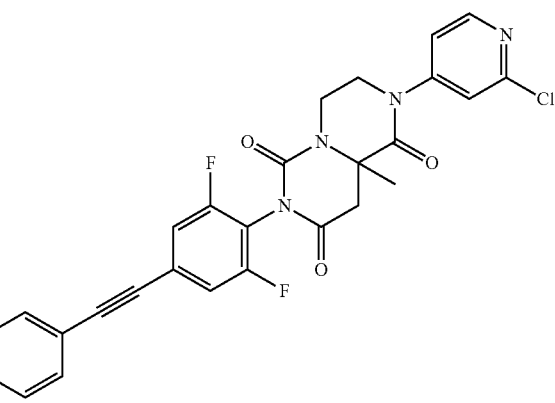 | (9aRS)-2-(2-chloro-4-pyridyl)-7-[2,6-difluoro-4-(2-phenylethynyl)phenyl]-9a-methyl-4,9-dihydro-3H-pyrazino[1,2-c]pyrimidine-1,6,8-trione | 114 | 131 |
| 19 | 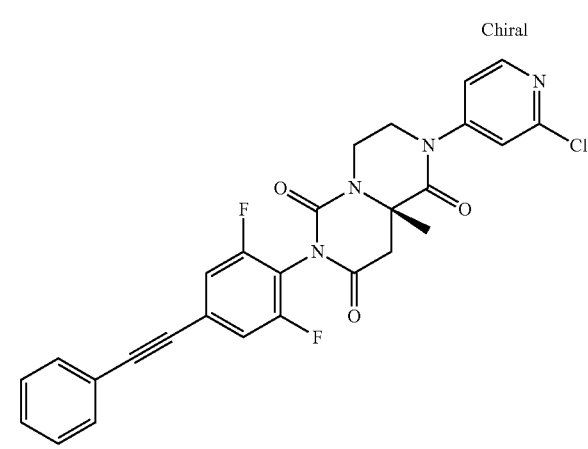 [SMILES: C[C@@]12CC(=O)N(c3c(F)cc(C#Cc4ccccc4)cc3F)C(=O)N1CCN(c1ccnc(Cl)c1)C2=O] Chiral | (9aS)-2-(2-chloro-4-pyridyl)-7-[2,6-difluoro-4-(2-phenylethynyl)phenyl]-9a-methyl-4,9-dihydro-3H-pyrazino[1,2-c]pyrimidine-1,6,8-trione | 69 | 100 |

-continued

List of Examples and data:

| Ex. | Structure | Name | EC$_{50}$ (nM) mGlu4PAM | Eff. (%) |
|---|---|---|---|---|
| 20 | 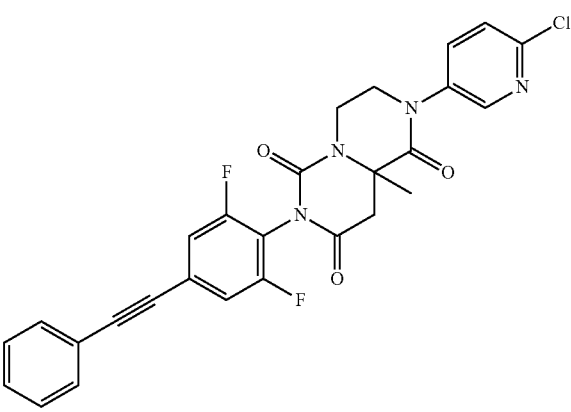 [SMILES: CC12CC(=O)N(c3c(F)cc(C#Cc4ccccc4)cc3F)C(=O)N1CCN(c1ccc(Cl)nc1)C2=O] | (9aRS)-2-(6-chloro-3-pyridyl)-7-[2,6-difluoro-4-(2-phenylethynyl)phenyl]-9a-methyl-4,9-dihydro-3H-pyrazino[1,2-c]pyrimidine-1,6,8-trione | 116 | 101 |
| 21 | Chiral 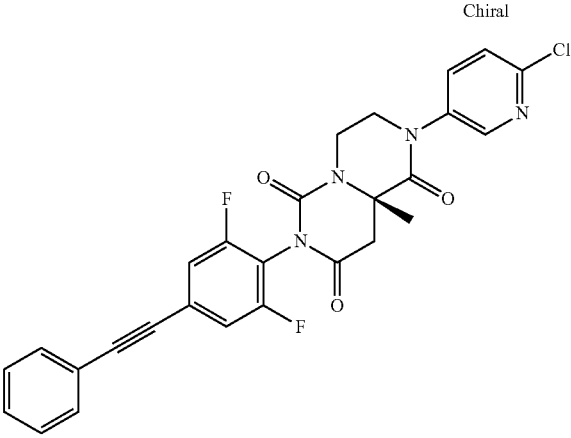 [SMILES: C[C@@]12CC(=O)N(c3c(F)cc(C#Cc4ccccc4)cc3F)C(=O)N1CCN(c1ccc(Cl)nc1)C2=O] | (9aS)-2-(6-chloro-3-pyridyl)-7-[2,6-difluoro-4-(2-phenylethynyl)phenyl]-9a-methyl-4,9-dihydro-3H-pyrazino[1,2-c]pyrimidine-1,6,8-trione | 73 | 142 |
| 22 | 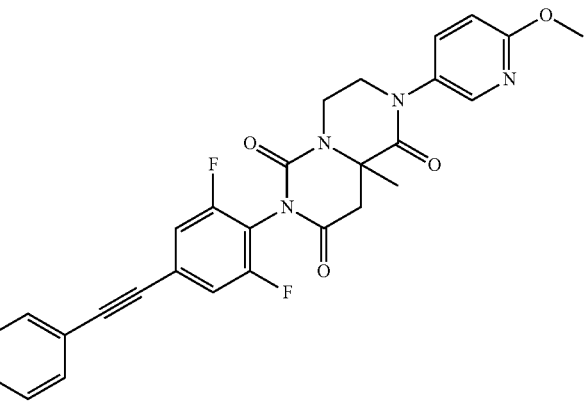 | (9aRS)-7-[2,6-difluoro-4-(2-phenylethynyl)phenyl]-2-(6-methoxy-3-pyridyl)-9a-methyl-4,9-dihydro-3H-pyrazino[1,2-c]pyrimidine-1,6,8-trione | 105 | 106 |

-continued

List of Examples and data:

| Ex. | Structure | Name | EC$_{50}$ (nM) mGlu4PAM | Eff. (%) |
|---|---|---|---|---|
| 23 | Chiral | (9aS)-7-[2,6-difluoro-4-(2-phenylethynyl)phenyl]-2-(6-methoxy-3-pyridyl)-9a-methyl-4,9-dihydro-3H-pyrazino[1,2-c]pyrimidine-1,6,8-trione | 61 | 114 |
| 24 | Chiral | (9aS)-7-[2,6-difluoro-4-(2-phenylethynyl)phenyl]-9a-methyl-2-(1-methyl-6-oxo-3-pyridyl)-4,9-dihydro-3H-pyrazino[1,2-c]pyrimidine-1,6,8-trione | 128 | 103 |
| 25 | 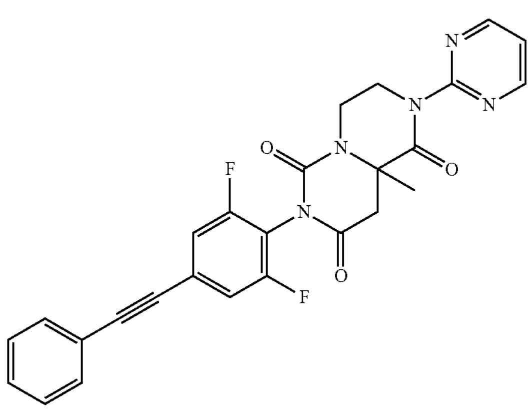 [SMILES: CC12CC(=O)N(c3c(F)cc(C#Cc4ccccc4)cc3F)C(=O)N1CCN(c1ncccn1)C2=O] | (9aRS)-7-[2,6-difluoro-4-(2-phenylethynyl)phenyl]-9a-methyl-2-pyrimidin-2-yl-4,9-dihydro-3H-pyrazino[1,2-c]pyrimidine-1,6,8-trione | 135 | 122 |

-continued

| | | | List of Examples and data: | | |
|---|---|---|---|---|---|
| Ex. | Structure | | Name | EC$_{50}$ (nM) mGlu4PAM | Eff. (%) |
| 26 | | | (9aRS)-7-[2,6-difluoro-4-(2-phenylethynyl)phenyl]-9a-methyl-2-pyrimidin-4-yl-4,9-dihydro-3H-pyrazino[1,2-c]pyrimidine-1,6,8-trione | 36 | 101 |
| 27 | | Chiral | (9aS)-7-[2,6-difluoro-4-(2-phenylethynyl)phenyl]-9a-methyl-2-pyrimidin-4-yl-4,9-dihydro-3H-pyrazino[1,2-c]pyrimidine-1,6,8-trione | 39 | 136 |
| 28 | | | (9aRS)-7-[2,6-difluoro-4-(2-phenylethynyl)phenyl]-9a-methyl-2-pyrimidin-5-yl-4,9-dihydro-3H-pyrazino[1,2-c]pyrimidine-1,6,8-trione | 145 | 120 |

-continued

List of Examples and data:

| Ex. | Structure | Name | EC$_{50}$ (nM) mGlu4PAM | Eff. (%) |
|---|---|---|---|---|
| 29 | 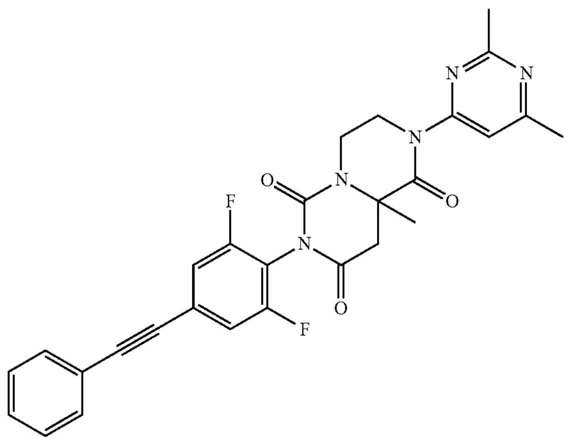 [SMILES: Cc1cc(N2CCN3C(=O)N(c4c(F)cc(C#Cc5ccccc5)cc4F)C(=O)CC3(C)C2=O)nc(C)n1] | (9aRS)-7-[2,6-difluoro-4-(2-phenylethynyl)phenyl]-2-(2,6-dimethylpyrimidin-4-yl)-9a-methyl-4,9-dihydro-3H-pyrazino[1,2-c]pyrimidine-1,6,8-trione | 177 | 112 |
| 30 | 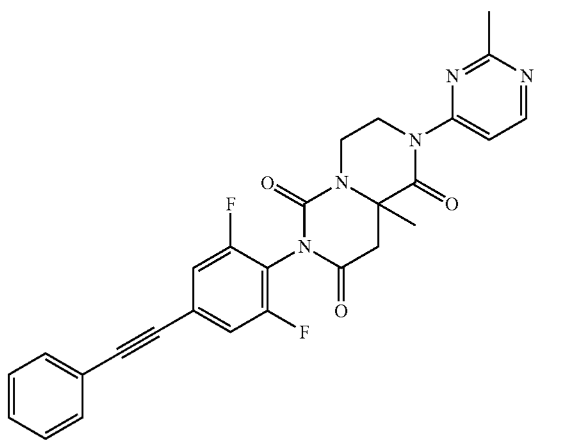 [SMILES: Cc1nccc(N2CCN3C(=O)N(c4c(F)cc(C#Cc5ccccc5)cc4F)C(=O)CC3(C)C2=O)n1] | (9aRS)-7-[2,6-difluoro-4-(2-phenylethynyl)phenyl]-9a-methyl-2-(2-methylpyrimidin-4-yl)-4,9-dihydro-3H-pyrazino[1,2-c]pyrimidine-1,6,8-trione | 113 | 101 |
| 31 | Chiral | (9aS)-7-[2,6-difluoro-4-(2-phenylethynyl)phenyl]-9a-methyl-2-(2-methylpyrimidin-4-yl)-4,9-dihydro-3H-pyrazino[1,2-c]pyrimidine-1,6,8-trione | 88 | 91 |

-continued

List of Examples and data:

| Ex. | Structure | Name | EC$_{50}$ (nM) mGlu4PAM | Eff. (%) |
|---|---|---|---|---|
| 32 | 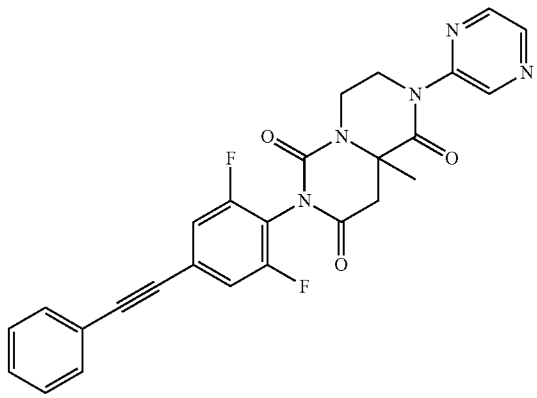 | (9aRS)-7-[2,6-difluoro-4-(2-phenylethynyl)phenyl]-9a-methyl-2-pyrazin-2-yl-4,9-dihydro-3H-pyrazino[1,2-c]pyrimidine-1,6,8-trione | 88 | 112 |
| 33 | Chiral | (9aS)-7-[2,6-difluoro-4-(2-phenylethynyl)phenyl]-9a-methyl-2-pyrazin-2-yl-4,9-dihydro-3H-pyrazino[1,2-c]pyrimidine-1,6,8-trione | 46 | 107 |
| 34 | 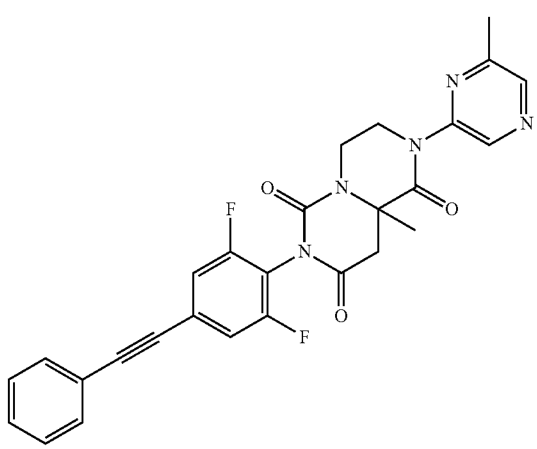 [SMILES: Cc1cncc(N2CCN3C(=O)N(c4c(F)cc(C#Cc5ccccc5)cc4F)C(=O)CC3(C)C2=O)n1] | (9aRS)-7-[2,6-difluoro-4-(2-phenylethynyl)phenyl]-9a-methyl-2-(6-methylpyrazin-2-yl)-4,9-dihydro-3H-pyrazino[1,2-c]pyrimidine-1,6,8-trione | 148 | 114 |

| Ex. | Structure | Name | EC$_{50}$ (nM) mGlu4PAM | Eff. (%) |
|---|---|---|---|---|
| 35 | 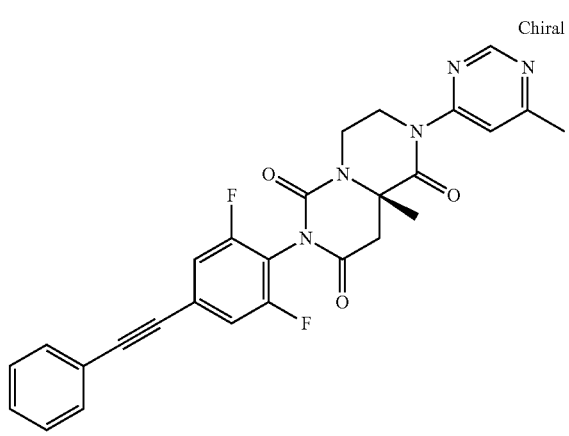 [SMILES: Cc1cc(N2CCN3C(=O)N(c4c(F)cc(C#Cc5ccccc5)cc4F)C(=O)C[C@@]3(C)C2=O)ncn1] | (9aS)-7-[2,6-difluoro-4-(2-phenylethynyl)phenyl]-9a-methyl-2-(6-methylpyrimidin-4-yl)-4,9-dihydro-3H-pyrazino[1,2-c]pyrimidine-1,6,8-trione | 91 | 121 |
| 36 | 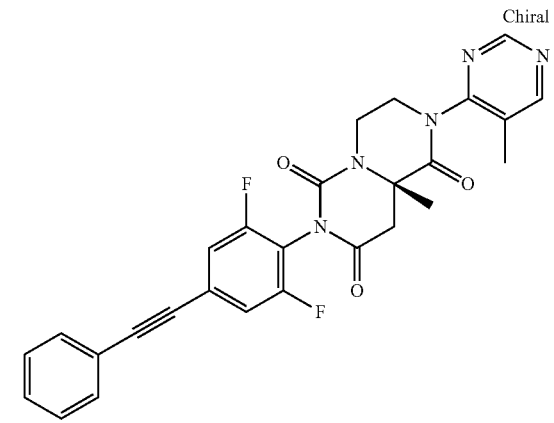 [SMILES: Cc1cncnc1N1CCN2C(=O)N(c3c(F)cc(C#Cc4ccccc4)cc3F)C(=O)C[C@@]2(C)C1=O] | (9aS)-7-[2,6-difluoro-4-(2-phenylethynyl)phenyl]-9a-methyl-2-(5-methylpyrimidin-4-yl)-4,9-dihydro-3H-pyrazino[1,2-c]pyrimidine-1,6,8-trione | 86 | 132 |
| 37 | 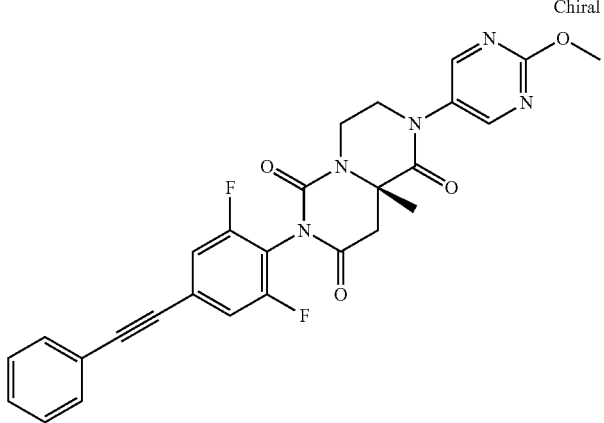 [SMILES: COc1ncc(N2CCN3C(=O)N(c4c(F)cc(C#Cc5ccccc5)cc4F)C(=O)C[C@@]3(C)C2=O)cn1] | (9aS)-7-[2,6-difluoro-4-(2-phenylethynyl)phenyl]-2-(2-methoxypyrimidin-5-yl)-9a-methyl-4,9-dihydro-3H-pyrazino[1,2-c]pyrimidine-1,6,8-trione | 55 | 90 |

-continued

List of Examples and data:

| Ex. | Structure | Name | EC$_{50}$ (nM) mGlu4PAM | Eff. (%) |
|---|---|---|---|---|
| 38 | Chiral | (9aS)-2-(2-tert-butoxypyrimidin-5-yl)-7-[2,6-difluoro-4-(2-phenylethynyl)phenyl]-9a-methyl-4,9-dihydro-3H-pyrazino[1,2-c]pyrimidine-1,6,8-trione | 157 | 107 |
| 39 | Chiral | (9aS or 9aR)-7-[2,6-difluoro-4-(2-phenylethynyl)phenyl]-2-(2-ethoxypyrimidin-5-yl)-9a-methyl-4,9-dihydro-3H-pyrazino[1,2-c]pyrimidine-1,6,8-trione | 96 | 103 |
| 40 | Chiral | (9aS)-7-[2,6-difluoro-4-(2-phenylethynyl)phenyl]-2-(2-isopropoxypyrimidin-5-yl)-9a-methyl-4,9-dihydro-3H-pyrazino[1,2-c]pyrimidine-1,6,8-trione | 113 | 103 |

-continued

List of Examples and data:

| Ex. | Structure | Name | EC$_{50}$ (nM) mGlu4PAM | Eff. (%) |
|---|---|---|---|---|
| 41 | Chiral | (9aS)-2-(2-benzyloxypyrimidin-5-yl)-7-[2,6-difluoro-4-(2-phenylethynyl)phenyl]-9a-methyl-4,9-dihydro-3H-pyrazino[1,2-c]pyrimidine-1,6,8-trione | 81 | 99 |
| 42 | Chiral | (9aS)-7-[2,6-difluoro-4-(2-phenylethynyl)phenyl]-2-(2-hydroxypyrimidin-5-yl)-9a-methyl-4,9-dihydro-3H-pyrazino[1,2-c]pyrimidine-1,6,8-trione | 73 | 129 |
| 43 | Chiral | (9aS)-2-[2-(cyclopropoxy)pyrimidin-5-yl]-7-[2,6-difluoro-4-(2-phenylethynyl)phenyl]-9a-methyl-4,9-dihydro-3H-pyrazino[1,2-c]pyrimidine-1,6,8-trione | 171 | 153 |

-continued

List of Examples and data:

| Ex. | Structure | Name | EC$_{50}$ (nM) mGlu4PAM | Eff. (%) |
|---|---|---|---|---|
| 44 | Chiral | (9aS)-7-[2,6-difluoro-4-(2-phenylethynyl)phenyl]-2-(5-methoxypyrazin-2-yl)-9a-methyl-4,9-dihydro-3H-pyrazino[1,2-c]pyrimidine-1,6,8-trione | 123 | 107 |
| 45 | Chiral | (9aS)-2-(5-benzyloxypyrazin-2-yl)-7-[2,6-difluoro-4-(2-phenylethynyl)phenyl]-9a-methyl-4,9-dihydro-3H-pyrazino[1,2-c]pyrimidine-1,6,8-trione | 190 | 122 |
| 46 | 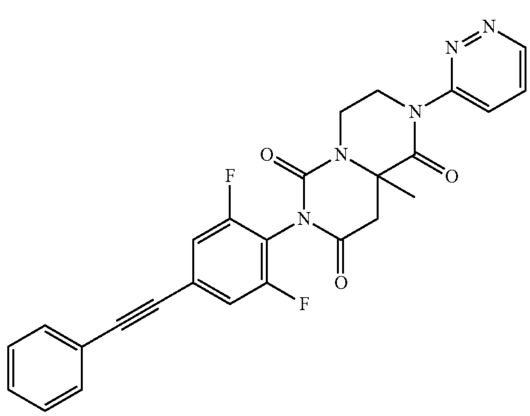 [SMILES: CC12CC(=O)N(c3c(F)cc(C#Cc4ccccc4)cc3F)C(=O)N1CCN(c1cccnn1)C2=O] | (9aRS)-7-[2,6-difluoro-4-(2-phenylethynyl)phenyl]-9a-methyl-2-pyridazin-3-yl-4,9-dihydro-3H-pyrazino[1,2-c]pyrimidine-1,6,8-trione | 132 | 106 |

-continued

List of Examples and data:

| Ex. | Structure | Name | EC$_{50}$ (nM) mGlu4PAM | Eff. (%) |
|---|---|---|---|---|
| 47 | 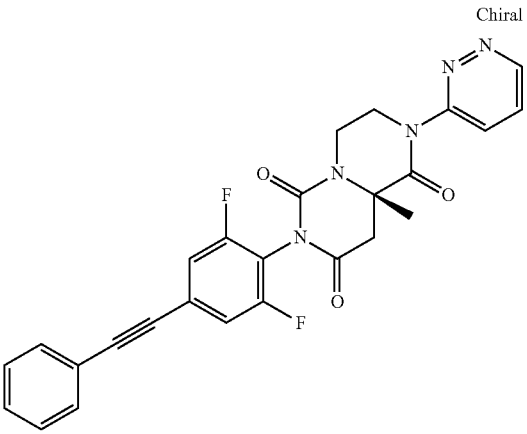 [SMILES: C[C@@]12CC(=O)N(c3c(F)cc(C#Cc4ccccc4)cc3F)C(=O)N1CCN(c1cccnn1)C2=O] Chiral | (9aS)-7-[2,6-difluoro-4-(2-phenylethynyl)phenyl]-9a-methyl-2-pyridazin-3-yl-4,9-dihydro-3H-pyrazino[1,2-c]pyrimidine-1,6,8-trione | 55 | 98 |
| 48 | 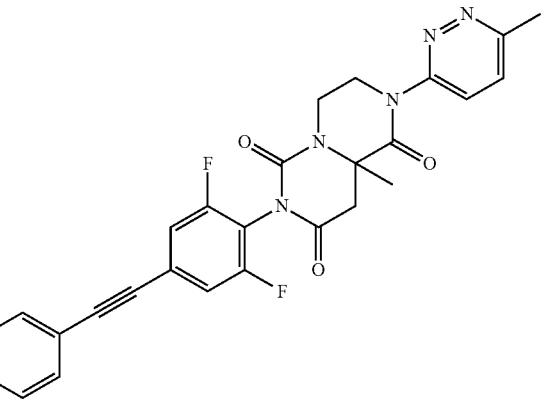 | (9aRS)-7-[2,6-difluoro-4-(2-phenylethynyl)phenyl]-9a-methyl-2-(6-methylpyridazin-3-yl)-4,9-dihydro-3H-pyrazino[1,2-c]pyrimidine-1,6,8-trione | 198 | 120 |
| 49 | 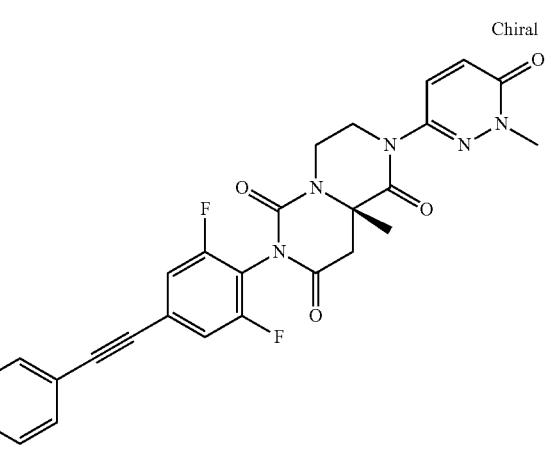 Chiral | (9aS)-7-[2,6-difluoro-4-(2-phenylethynyl)phenyl]-9a-methyl-2-(1-methyl-6-oxo-pyridazin-3-yl)-4,9-dihydro-3H-pyrazino[1,2-c]pyrimidine-1,6,8-trione | 197 | 109 |

-continued

List of Examples and data:

| Ex. | Structure | Name | EC$_{50}$ (nM) mGlu4PAM | Eff. (%) |
|---|---|---|---|---|
| 50 | 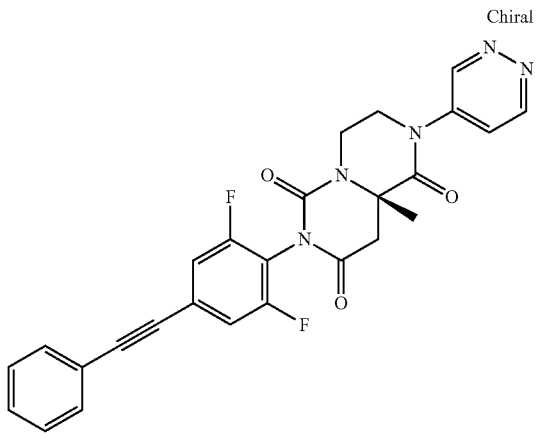 [SMILES: C[C@@]12CC(=O)N(c3c(F)cc(C#Cc4ccccc4)cc3F)C(=O)N1CCN(c1ccnnc1)C2=O] | (9aS)-7-[2,6-difluoro-4-(2-phenylethynyl)phenyl]-9a-methyl-2-pyridazin-4-yl-4,9-dihydro-3H-pyrazino[1,2-c]pyrimidine-1,6,8-trione | 74 | 133 |
| 51 | 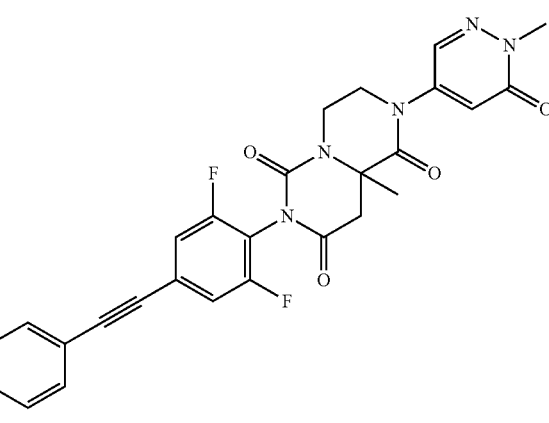 | (9aRS)-7-(2,6-difluoro-4-(phenylethynyl)phenyl)-9a-methyl-2-(1-methyl-6-oxo-1,6-dihydropyridazin-4-yl)tetrahydro-1H-pyrazino[1,2-c]pyrimidine-1,6,8(2H,7H)-trione | 191 | 120 |
| 52 | 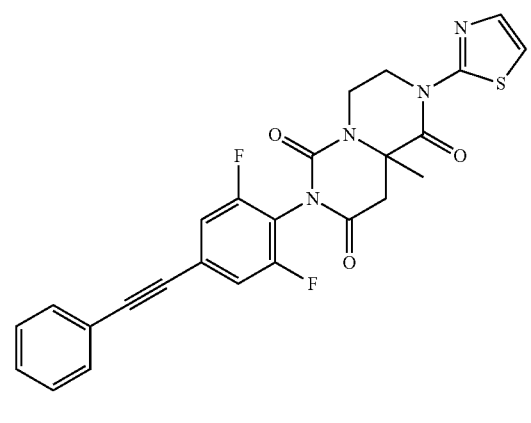 [SMILES: CC12CC(=O)N(c3c(F)cc(C#Cc4ccccc4)cc3F)C(=O)N1CCN(c1nccs1)C2=O] | (9aRS)-7-[2,6-difluoro-4-(2-phenylethynyl)phenyl]-9a-methyl-2-thiazol-2-yl-4,9-dihydro-3H-pyrazino[1,2-c]pyrimidine-1,6,8-trione | 113 | 97 |

-continued

List of Examples and data:

| Ex. | Structure | Name | EC$_{50}$ (nM) mGlu4PAM | Eff. (%) |
|---|---|---|---|---|
| 53 | 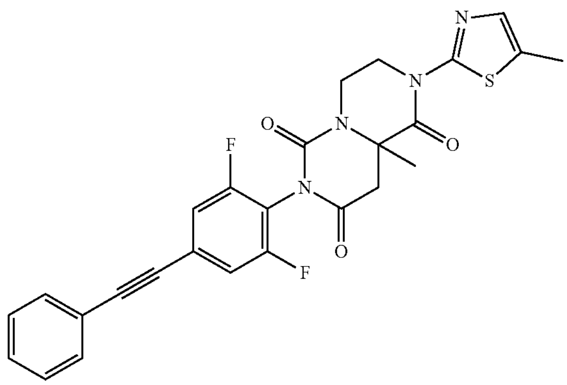 [SMILES: Cc1cnc(N2CCN3C(=O)N(c4c(F)cc(C#Cc5ccccc5)cc4F)C(=O)CC3(C)C2=O)s1] | (9aRS)-7-[2,6-difluoro-4-(2-phenylethynyl)phenyl]-9a-methyl-2-(5-methylthiazol-2-yl)-4,9-dihydro-3H-pyrazino[1,2-c]pyrimidine-1,6,8-trione | 88 | 100 |
| 54 | 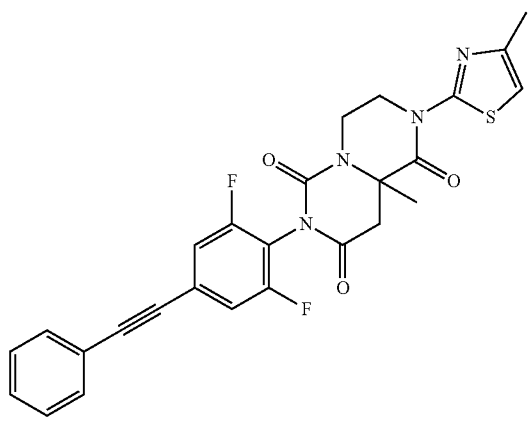 [SMILES: Cc1csc(N2CCN3C(=O)N(c4c(F)cc(C#Cc5ccccc5)cc4F)C(=O)CC3(C)C2=O)n1] | (9aRS)-7-[2,6-difluoro-4-(2-phenylethynyl)phenyl]-9a-methyl-2-(4-methylthiazol-2-yl)-4,9-dihydro-3H-pyrazino[1,2-c]pyrimidine-1,6,8-trione | 48 | 97 |
| 55 | 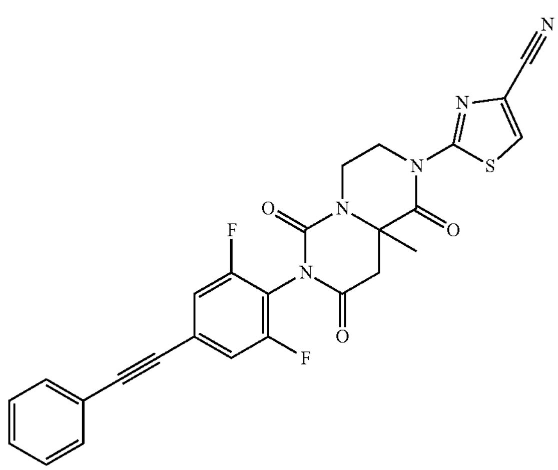 [SMILES: CC12CC(=O)N(c3c(F)cc(C#Cc4ccccc4)cc3F)C(=O)N1CCN(c1nc(C#N)cs1)C2=O] | 2-[(9aRS)-7-[2,6-difluoro-4-(2-phenylethynyl)phenyl]-9a-methyl-1,6,8-trioxo-4,9-dihydro-3H-pyrazino[1,2-c]pyrimidin-2-yl]thiazole-4-carbonitrile | 77 | 94 |

-continued

| | | | List of Examples and data: | | |
|---|---|---|---|---|---|
| Ex. | Structure | | Name | EC$_{50}$ (nM) mGlu4PAM | Eff. (%) |
| 56 | | | (9aRS)-7-[2,6-difluoro-4-(2-phenylethynyl)phenyl]-9a-methyl-2-[4-(trifluoromethyl)thiazol-2-yl]-4,9-dihydro-3H-pyrazino[1,2-c]pyrimidine-1,6,8-trione | 166 | 88 |
| 57 | | | (9aRS)-7-[2,6-difluoro-4-(2-phenylethynyl)phenyl]-9a-methyl-2-[5-(trifluoromethyl)thiazol-2-yl]-4,9-dihydro-3H-pyrazino[1,2-c]pyrimidine-1,6,8-trione | 108 | 103 |
| 58 | | | (9aRS)-7-[2,6-difluoro-4-(2-phenylethynyl)phenyl]-9a-methyl-2-(1-methylimidazol-4-yl)-4,9-dihydro-3H-pyrazino[1,2-c]pyrimidine-1,6,8-trione | 214 | 91 |

-continued

List of Examples and data:

| Ex. | Structure | Name | EC$_{50}$ (nM) mGlu4PAM | Eff. (%) |
|---|---|---|---|---|
| 59 | 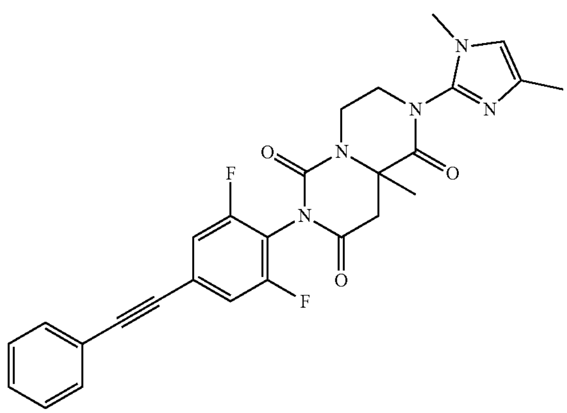 [SMILES: Cc1cn(C)c(N2CCN3C(=O)N(c4c(F)cc(C#Cc5ccccc5)cc4F)C(=O)CC3(C)C2=O)n1] | (9aRS)-7-[2,6-difluoro-4-(2-phenylethynyl)phenyl]-2-(1,4-dimethylimidazol-2-yl)-9a-methyl-4,9-dihydro-3H-pyrazino[1,2-c]pyrimidine-1,6,8-trione | 104 | 107 |
| 60 | 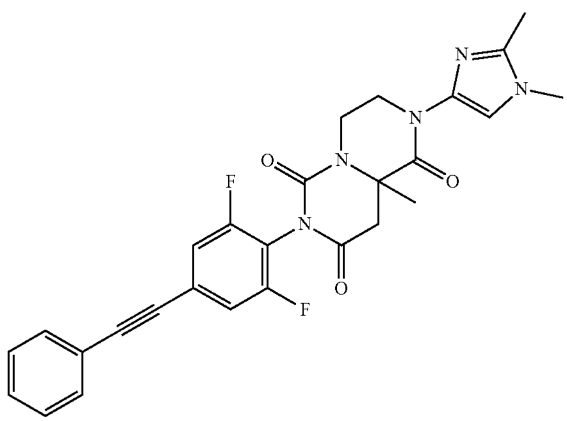 [SMILES: Cc1nc(N2CCN3C(=O)N(c4c(F)cc(C#Cc5ccccc5)cc4F)C(=O)CC3(C)C2=O)cn1C] | (9aRS)-7-[2,6-difluoro-4-(2-phenylethynyl)phenyl]-2-(1,2-dimethylimidazol-4-yl)-9a-methyl-4,9-dihydro-3H-pyrazino[1,2-c]pyrimidine-1,6,8-trione | 145 | 137 |
| 61 | 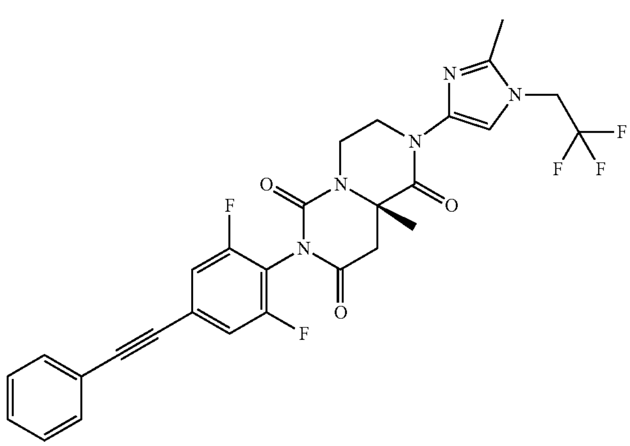 | (9aS)-7-[2,6-difluoro-4-(2-phenylethynyl)phenyl]-9a-methyl-2-[2-methyl-1-(2,2,2-trifluoroethyl)-imidazol-4-yl]-4,9-dihydro-3H-pyrazino[1,2-c]pyrimidine-1,6,8-trione | 272 | 172 |

-continued

List of Examples and data:

| Ex. | Structure | Name | EC$_{50}$ (nM) mGlu4PAM | Eff. (%) |
|---|---|---|---|---|
| 62 | 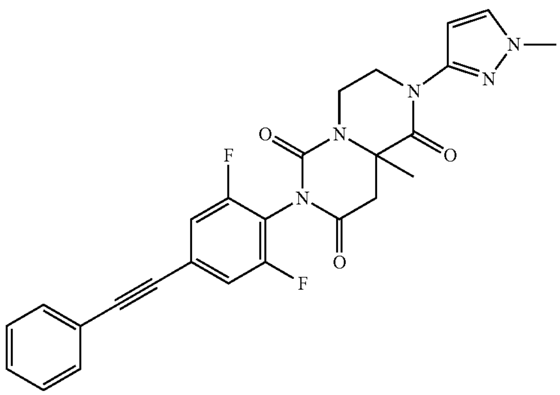 [SMILES: Cn1ccc(N2CCN3C(=O)N(c4c(F)cc(C#Cc5ccccc5)cc4F)C(=O)CC3(C)C2=O)n1] | (9aRS)-7-[2,6-difluoro-4-(2-phenylethynyl)phenyl]-9a-methyl-2-(1-methylpyrazol-3-yl)-4,9-dihydro-3H-pyrazino[1,2-c]pyrimidine-1,6,8-trione | 149 | 112 |
| 63 | Chiral | (9aS)-7-[2,6-difluoro-4-(2-phenylethynyl)phenyl]-9a-methyl-2-(1-methylpyrazol-3-yl)-4,9-dihydro-3H-pyrazino[1,2-c]pyrimidine-1,6,8-trione | 165 | 136 |
| 64 | 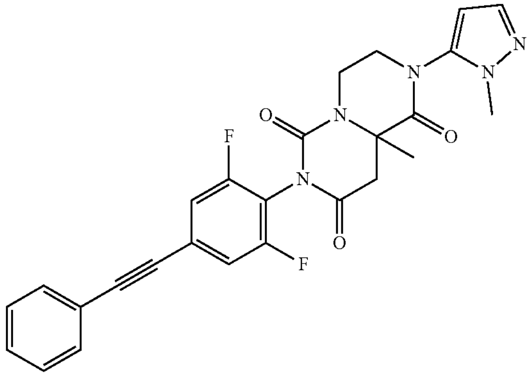 [SMILES: Cn1nccc1N1CCN2C(=O)N(c3c(F)cc(C#Cc4ccccc4)cc3F)C(=O)CC2(C)C1=O] | (9aRS)-7-[2,6-difluoro-4-(2-phenylethynyl)phenyl]-9a-methyl-2-(2-methylpyrazol-3-yl)-4,9-dihydro-3H-pyrazino[1,2-c]pyrimidine-1,6,8-trione | 125 | 155 |

-continued

List of Examples and data:

| Ex. | Structure | Name | EC$_{50}$ (nM) mGlu4PAM | Eff. (%) |
|---|---|---|---|---|
| 65 | 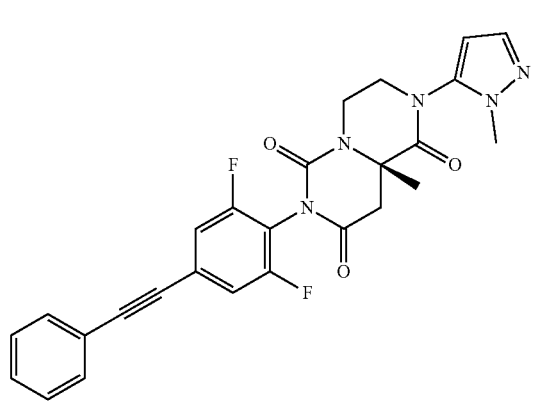 Chiral | (9aS)-7-[2,6-difluoro-4-(2-phenylethynyl)phenyl]-9a-methyl-2-(2-methylpyrazol-3-yl)-4,9-dihydro-3H-pyrazino[1,2-c]pyrimidine-1,6,8-trione | 92 | 92 |
| 66 | 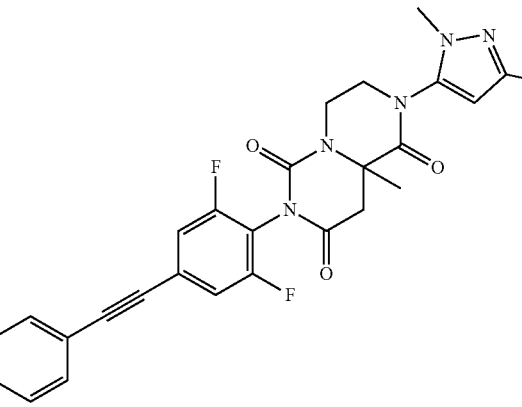 | (9aRS)-7-[2,6-difluoro-4-(2-phenylethynyl)phenyl]-2-(2,5-dimethylpyrazol-3-yl)-9a-methyl-4,9-dihydro-3H-pyrazino[1,2-c]pyrimidine-1,6,8-trione | 85 | 142 |
| 67 | 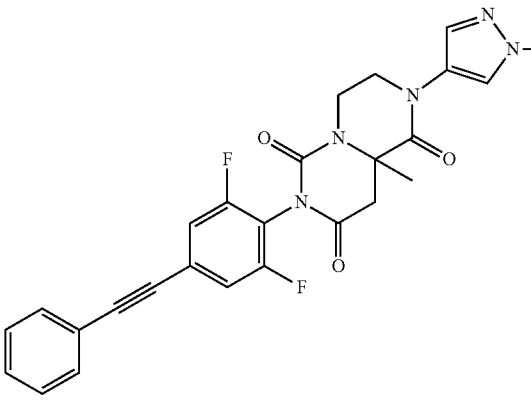 | (9aRS)-7-[2,6-difluoro-4-(2-phenylethynyl)phenyl]-9a-methyl-2-(1-methylpyrazol-4-yl)-4,9-dihydro-3H-pyrazino[1,2-c]pyrimidine-1,6,8-trione | 113 | 129 |

-continued

List of Examples and data:

| Ex. | Structure | Name | EC$_{50}$ (nM) mGlu4PAM | Eff. (%) |
|---|---|---|---|---|
| 68 | Chiral | (9aS)-7-[2,6-difluoro-4-(2-phenylethynyl)phenyl]-9a-methyl-2-(1-methylpyrazol-4-yl)-4,9-dihydro-3H-pyrazino[1,2-c]pyrimidine-1,6,8-trione | 90 | 135 |
| 69 | Chiral | (9aS)-7-[2,6-difluoro-4-(2-phenylethynyl)phenyl]-2-(1-ethylpyrazol-4-yl)-9a-methyl-4,9-dihydro-3H-pyrazino[1,2-c]pyrimidine-1,6,8-trione | 151 | 184 |
| 70 | Chiral | (9aS)-7-[2,6-difluoro-4-(2-phenylethynyl)phenyl]-2-(1-isopropylpyrazol-4-yl)-9a-methyl-4,9-dihydro-3H-pyrazino[1,2-c]pyrimidine-1,6,8-trione | 139 | 150 |

-continued

| Ex. | Structure | Name | EC$_{50}$ (nM) mGlu4PAM | Eff. (%) |
|---|---|---|---|---|
| 71 | Chiral | (9aS)-7-[2,6-difluoro-4-(2-phenylethynyl)phenyl]-9a-methyl-2-(1H-pyrazol-4-yl)-4,9-dihydro-3H-pyrazino[1,2-c]pyrimidine-1,6,8-trione | 101 | 182 |
| 72 | Chiral | (9aS)-7-[2,6-difluoro-4-(2-phenylethynyl)phenyl]-2-[1-(3-methoxypropyl)pyrazol-4-yl]-9a-methyl-4,9-dihydro-3H-pyrazino[1,2-c]pyrimidine-1,6,8-trione | 122 | 149 |
| 73 | Chiral | (9aS)-7-[2,6-difluoro-4-(2-phenylethynyl)phenyl]-9a-methyl-2-(1-methyl-1,2,4-triazol-3-yl)-4,9-dihydro-3H-pyrazino[1,2-c]pyrimidine-1,6,8-trione | 244 | 138 |

-continued

List of Examples and data:

| Ex. | Structure | Name | EC$_{50}$ (nM) mGlu4PAM | Eff. (%) |
|---|---|---|---|---|
| 74 | 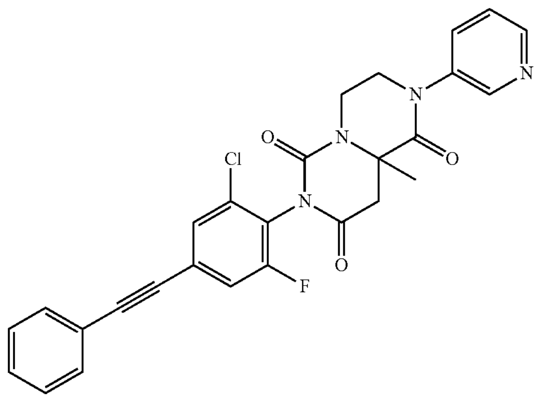 | (9aRS)-7-[2-chloro-6-fluoro-4-(2-phenylethynyl)phenyl]-9a-methyl-2-(3-pyridyl)-4,9-dihydro-3H-pyrazino[1,2-c]pyrimidine-1,6,8-trione | 102 | 120 |
| 75 | 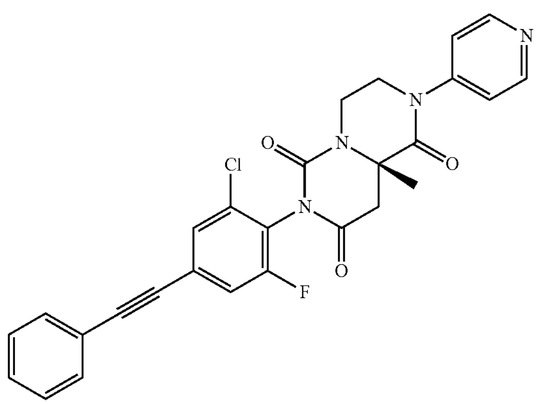 | (9aRS)-7-[2-chloro-6-fluoro-4-(2-phenylethynyl)phenyl]-9a-methyl-2-(4-pyridyl)-4,9-dihydro-3H-pyrazino[1,2-c]pyrimidine-1,6,8-trione | 210 | 128 |
| 76 | 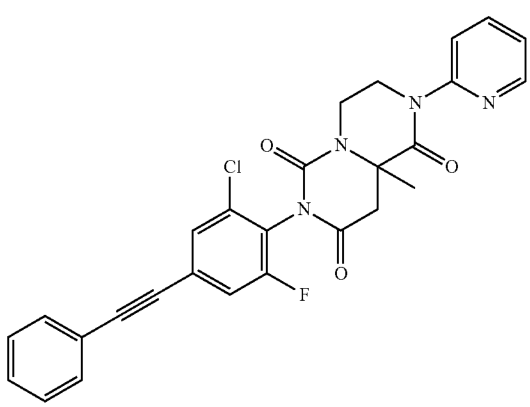 [SMILES: CC12CC(=O)N(c3c(F)cc(C#Cc4ccccc4)cc3Cl)C(=O)N1CCN(c1ccccn1)C2=O] | (9aRS)-7-[2-chloro-6-fluoro-4-(2-phenylethynyl)phenyl]-9a-methyl-2-(2-pyridyl)-4,9-dihydro-3H-pyrazino[1,2-c]pyrimidine-1,6,8-trione | 128 | 150 |

-continued

| | | | List of Examples and data: | | |
|---|---|---|---|---|---|
| Ex. | Structure | | Name | EC$_{50}$ (nM) mGlu4PAM | Eff. (%) |
| 77 | | | (9aRS)-7-[2-chloro-6-fluoro-4-(2-phenylethynyl)phenyl]-9a-methyl-2-(1-methylpyrazol-4-yl)-4,9-dihydro-3H-pyrazino[1,2-c]pyrimidine-1,6,8-trione | 104 | 111 |
| 78 | | Chiral | (9aS)-7-[2-chloro-6-fluoro-4-(2-phenylethynyl)phenyl]-9a-methyl-2-(1-methylpyrazol-4-yl)-4,9-dihydro-3H-pyrazino[1,2-c]pyrimidine-1,6,8-trione | 75 | 117 |
| 79 | | Chiral | (9aS)-7-[2,6-difluoro-4-(2-phenylethynyl)phenyl]-2-(2-methoxyethyl)-9a-methyl-4,9-dihydro-3H-pyrazino[1,2-c]pyrimidine-1,6,8-trione | 137 | 122 |

-continued

List of Examples and data:

| Ex. | Structure | Name | EC$_{50}$ (nM) mGlu4PAM | Eff. (%) |
|---|---|---|---|---|
| 80 | Chiral | (9aS)-7-[2,6-difluoro-4-(2-phenylethynyl)phenyl]-2-(3-methoxypropyl)-9a-methyl-4,9-dihydro-3H-pyrazino[1,2-c]pyrimidine-1,6,8-trione | 135 | 132 |
| 81 | Chiral | (9aS)-7-[2,6-difluoro-4-(2-phenylethynyl)phenyl]-9a-methyl-2-(2,2,2-trifluoroethyl)-4,9-dihydro-3H-pyrazino[1,2-c]pyrimidine-1,6,8-trione | 112 | 172 |
| 82 | Chiral | Ethyl 4-[(9aS)-7-[2,6-difluoro-4-(2-phenylethynyl)phenyl]-9a-methyl-1,6,8-trioxo-4,9-dihydro-3H-pyrazino[1,2-c]pyrimidin-2-yl]butanoate | 201 | 134 |
| 83 | 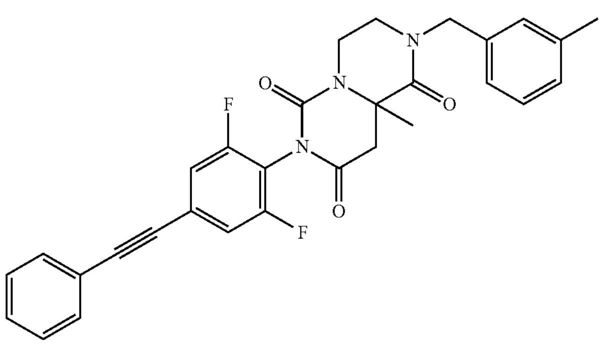 [SMILES: Cc1cccc(CN2CCN3C(=O)N(c4c(F)cc(C#Cc5ccccc5)cc4F)C(=O)CC3(C)C2=O)c1] | (9aRS)-7-[2,6-difluoro-4-(2-phenylethynyl)phenyl]-9a-methyl-2-(m-tolylmethyl)-4,9-dihydro-3H-pyrazino[1,2-c]pyrimidine-1,6,8-trione | 173 | 79 |

-continued

List of Examples and data:

| Ex. | Structure | Name | EC$_{50}$ (nM) mGlu4PAM | Eff. (%) |
|---|---|---|---|---|
| 84 | 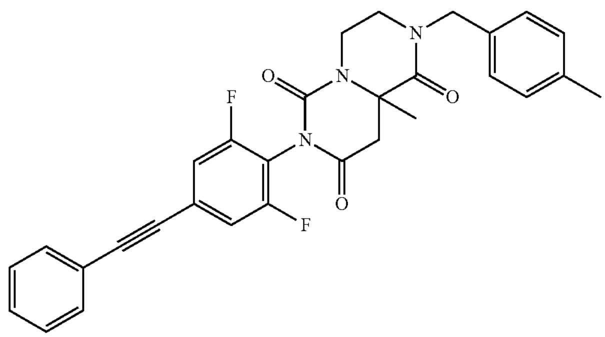 [SMILES: Cc1ccc(CN2CCN3C(=O)N(c4c(F)cc(C#Cc5ccccc5)cc4F)C(=O)CC3(C)C2=O)cc1] | (9aRS)-7-[2,6-difluoro-4-(2-phenylethynyl)phenyl]-9a-methyl-2-(p-tolylmethyl)-4,9-dihydro-3H-pyrazino[1,2-c]pyrimidine-1,6,8-trione | 117 | 87 |
| 85 | 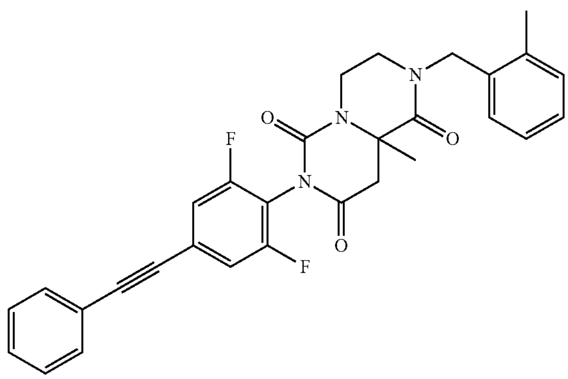 [SMILES: Cc1ccccc1CN1CCN2C(=O)N(c3c(F)cc(C#Cc4ccccc4)cc3F)C(=O)CC2(C)C1=O] | (9aRS)-7-[2,6-difluoro-4-(2-phenylethynyl)phenyl]-9a-methyl-2-(o-tolylmethyl)-4,9-dihydro-3H-pyrazino[1,2-c]pyrimidine-1,6,8-trione | 205 | 83 |
| 86 | 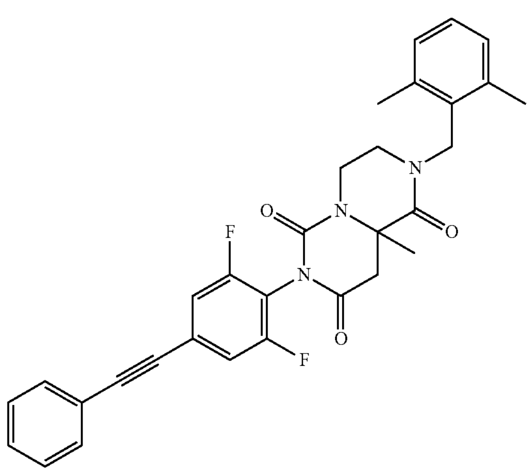 [SMILES: Cc1cccc(C)c1CN1CCN2C(=O)N(c3c(F)cc(C#Cc4ccccc4)cc3F)C(=O)CC2(C)C1=O] | (9aRS)-7-[2,6-difluoro-4-(2-phenylethynyl)phenyl]-2-[(2,6-dimethylphenyl)methyl]-9a-methyl-4,9-dihydro-3H-pyrazino[1,2-c]pyrimidine-1,6,8-trione | 68 | 118 |

-continued

List of Examples and data:

| Ex. | Structure | Name | EC$_{50}$ (nM) mGlu4PAM | Eff. (%) |
|---|---|---|---|---|
| 87 | 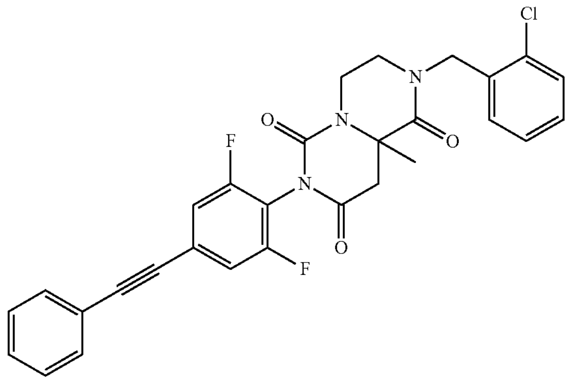 [SMILES: CC12CC(=O)N(c3c(F)cc(C#Cc4ccccc4)cc3F)C(=O)N1CCN(Cc1ccccc1Cl)C2=O] | (9aRS)-2-[(2-chlorophenyl)methyl]-7-[2,6-difluoro-4-(2-phenylethynyl)phenyl]-9a-methyl-4,9-dihydro-3H-pyrazino[1,2-c]pyrimidine-1,6,8-trione | 87 | 131 |
| 88 | 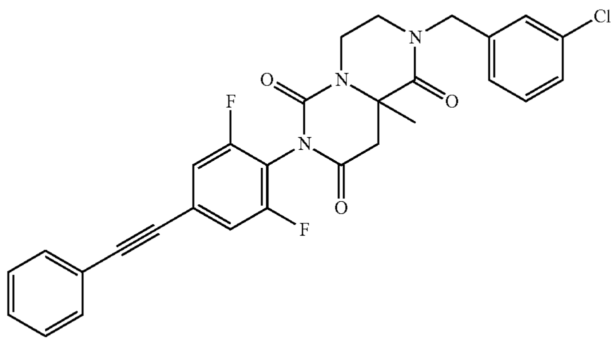 [SMILES: CC12CC(=O)N(c3c(F)cc(C#Cc4ccccc4)cc3F)C(=O)N1CCN(Cc1cccc(Cl)c1)C2=O] | (9aRS)-2-[(3-chlorophenyl)methyl]-7-[2,6-difluoro-4-(2-phenylethynyl)phenyl]-9a-methyl-4,9-dihydro-3H-pyrazino[1,2-c]pyrimidine-1,6,8-trione | 73 | 134 |
| 89 | Chiral | (9aS)-7-[2,6-difluoro-4-(2-phenylethynyl)phenyl]-2-[(2-fluorophenyl)methyl]-9a-methyl-4,9-dihydro-3H-pyrazino[1,2-c]pyrimidine-1,6,8-trione | 149 | 98 |
| 90 | Chiral | (9aS)-7-[2,6-difluoro-4-(2-phenylethynyl)phenyl]-2-[(3-fluorophenyl)methyl]-9a-methyl-4,9-dihydro-3H-pyrazino[1,2-c]pyrimidine-1,6,8-trione | 187 | 109 |

-continued

| | | | EC$_{50}$ (nM) | Eff. |
|---|---|---|---|---|
| Ex. | Structure | Name | mGlu4PAM | (%) |
| 91 | Chiral | (9aS)-7-[2,6-difluoro-4-(2-phenylethynyl)phenyl]-2-[(4-fluorophenyl)methyl]-9a-methyl-4,9-dihydro-3H-pyrazino[1,2-c]pyrimidine-1,6,8-trione | 147 | 101 |
| 92 | | (9aRS)-7-[2,6-difluoro-4-(2-phenylethynyl)phenyl]-9a-methyl-2-(2-pyridylmethyl)-4,9-dihydro-3H-pyrazino[1,2-c]pyrimidine-1,6,8-trione | 198 | 91 |
| 93 | | (9aRS)-7-[2,6-difluoro-4-(2-phenylethynyl)phenyl]-9a-methyl-2-(3-pyridylmethyl)-4,9-dihydro-3H-pyrazino[1,2-c]pyrimidine-1,6,8-trione | 217 | 90 |
| 94 | | (9aRS)-7-[2,6-difluoro-4-(2-phenylethynyl)phenyl]-9a-methyl-2-(4-pyridylmethyl)-4,9-dihydro-3H-pyrazino[1,2-c]pyrimidine-1,6,8-trione | 127 | 84 |

| Ex. | Structure | Name | EC$_{50}$ (nM) mGlu4PAM | Eff. (%) |
|---|---|---|---|---|
| 95 | 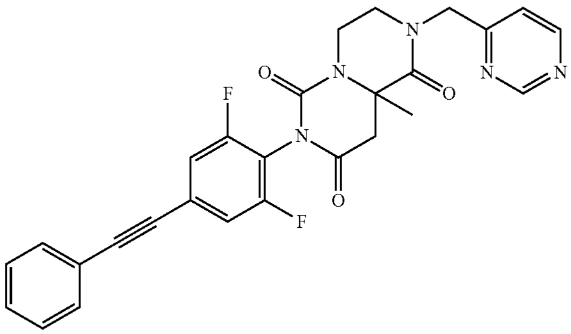 [SMILES: CC12CC(=O)N(c3c(F)cc(C#Cc4ccccc4)cc3F)C(=O)N1CCN(Cc1ccncn1)C2=O] | (9aRS)-7-[2,6-difluoro-4-(2-phenylethynyl)phenyl]-9a-methyl-2-(pyrimidin-4-ylmethyl)-4,9-dihydro-3H-pyrazino[1,2-c]pyrimidine-1,6,8-trione | 142 | 96 |
| 96 | 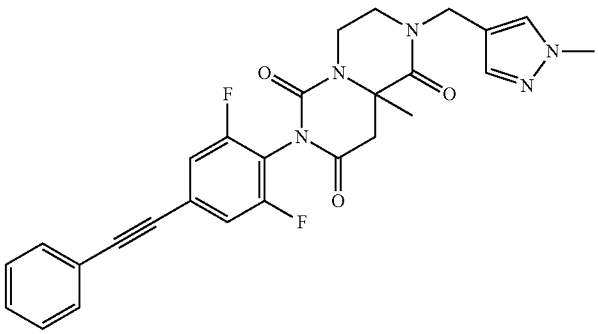 [SMILES: Cn1cc(CN2CCN3C(=O)N(c4c(F)cc(C#Cc5ccccc5)cc4F)C(=O)CC3(C)C2=O)cn1] | (9aRS)-7-[2,6-difluoro-4-(2-phenylethynyl)phenyl]-9a-methyl-2-[(1-methylpyrazol-4-yl)methyl]-4,9-dihydro-3H-pyrazino[1,2-c]pyrimidine-1,6,8-trione | 214 | 151 |
| 97 | Chiral | (9aS)-7-[2,6-difluoro-4-(2-phenylethynyl)phenyl]-9a-methyl-2-[(2-methylpyrazol-3-yl)methyl]-4,9-dihydro-3H-pyrazino[1,2-c]pyrimidine-1,6,8-trione | 76 | 128 |
| 98 | Chiral | (9aS)-7-[2,6-difluoro-4-(2-phenylethynyl)phenyl]-2-(2-imidazol-1-ylethyl)-9a-methyl-4,9-dihydro-3H-pyrazino[1,2-c]pyrimidine-1,6,8-trione | 283 | 135 |

-continued

List of Examples and data:

| Ex. | Structure | Name | EC$_{50}$ (nM) mGlu4PAM | Eff. (%) |
|---|---|---|---|---|
| 99 | Chiral | (9aS)-7-[2,6-difluoro-4-(2-phenylethynyl)phenyl]-9a-methyl-2-[2-(2-methylimidazol-1-yl)ethyl]-4,9-dihydro-3H-pyrazino[1,2-c]pyrimidine-1,6,8-trione | 282 | 146 |
| 100 | Chiral | (9aS)-7-[2,6-difluoro-4-(2-phenylethynyl)phenyl]-9a-methyl-2-[2-(2-methylpyrazol-3-yl)ethyl]-4,9-dihydro-3H-pyrazino[1,2-c]pyrimidine-1,6,8-trione | 219 | 123 |
| 101 | Chiral | (9aS)-7-[2,6-difluoro-4-(2-phenylethynyl)phenyl]-9a-methyl-2-[2-(1-methylpyrazol-4-yl)ethyl]-4,9-dihydro-3H-pyrazino[1,2-c]pyrimidine-1,6,8-trione | 125 | 129 |

-continued

List of Examples and data:

| Ex. | Structure | Name | EC$_{50}$ (nM) mGlu4PAM | Eff. (%) |
|---|---|---|---|---|
| 102 | 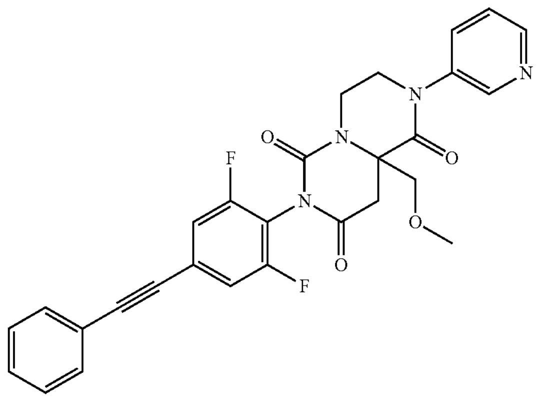 [SMILES: COCC12CC(=O)N(c3c(F)cc(C#Cc4ccccc4)cc3F)C(=O)N1CCN(c1cccnc1)C2=O] | (9aRS)-7-[2,6-difluoro-4-(2-phenylethynyl)phenyl]-9a-(methoxymethyl)-2-(3-pyridyl)-4,9-dihydro-3H-pyrazino[1,2-c]pyrimidine-1,6,8-trione | 129 | 136 |
| 103 | 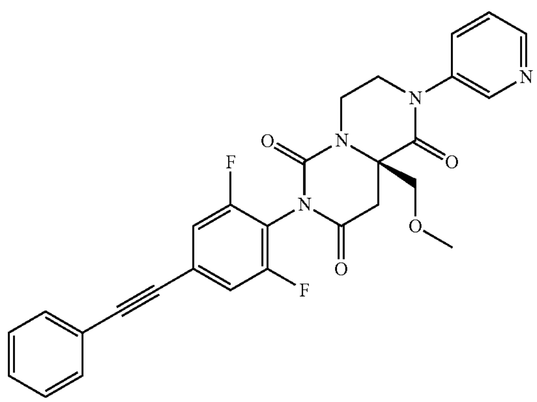 [SMILES: COC[C@@]12CC(=O)N(c3c(F)cc(C#Cc4ccccc4)cc3F)C(=O)N1CCN(c1cccnc1)C2=O] | (9aR)-7-[2,6-difluoro-4-(2-phenylethynyl)phenyl]-9a-(methoxymethyl)-2-(3-pyridyl)-4,9-dihydro-3H-pyrazino[1,2-c]pyrimidine-1,6,8-trione | 169 | 118 |
| 104 | 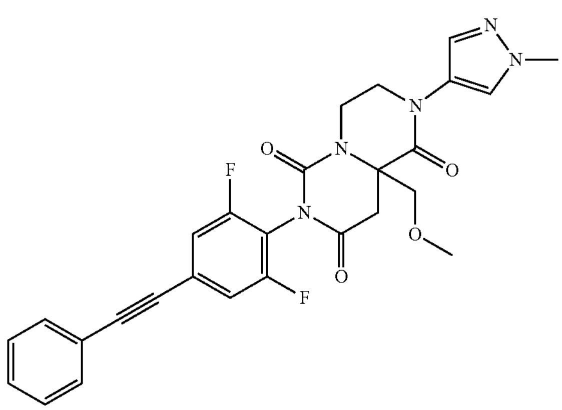 [SMILES: COCC12CC(=O)N(c3c(F)cc(C#Cc4ccccc4)cc3F)C(=O)N1CCN(c1cnn(C)c1)C2=O] | (9aRS)-7-[2,6-difluoro-4-(2-phenylethynyl)phenyl]-9a-(methoxymethyl)-2-(1-methylpyrazol-4-yl)-4,9-dihydro-3H-pyrazino[1,2-c]pyrimidine-1,6,8-trione | 273 | 148 |

-continued

List of Examples and data:

| Ex. | Structure | Name | EC$_{50}$ (nM) mGlu4PAM | Eff. (%) |
|---|---|---|---|---|
| 105 | 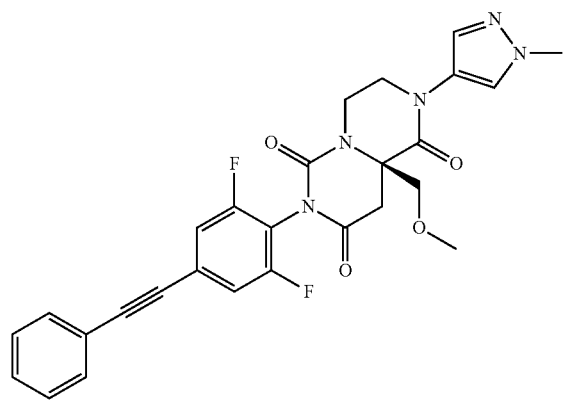 [SMILES: COC[C@@]12CC(=O)N(c3c(F)cc(C#Cc4ccccc4)cc3F)C(=O)N1CCN(c1cnn(C)c1)C2=O] | (9aR)-7-[2,6-difluoro-4-(2-phenylethynyl)phenyl]-9a-(methoxymethyl)-2-(1-methylpyrazol-4-yl)-4,9-dihydro-3H-pyrazino[1,2-c]pyrimidine-1,6,8-trione | 61 | 144 |
| 106 | 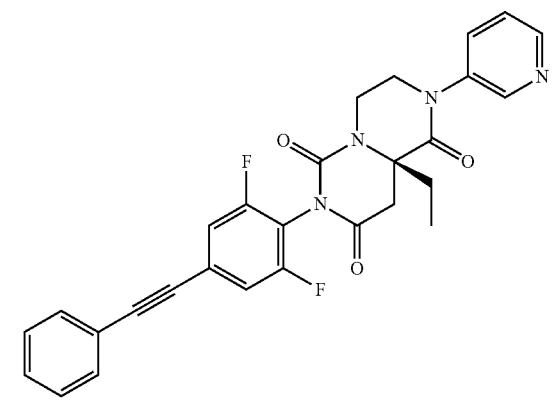 [SMILES: CC[C@@]12CC(=O)N(c3c(F)cc(C#Cc4ccccc4)cc3F)C(=O)N1CCN(c1cccnc1)C2=O] | (9aS)-7-[2,6-difluoro-4-(2-phenylethynyl)phenyl]-9a-ethyl-2-(3-pyridyl)-4,9-dihydro-3H-pyrazino[1,2-c]pyrimidine-1,6,8-trione | 95 | 112 |
| 107 | 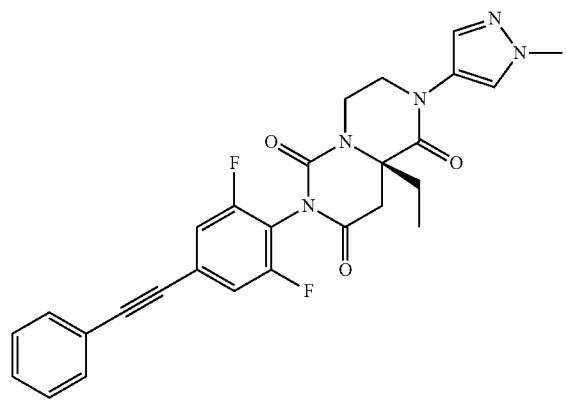 [SMILES: CC[C@@]12CC(=O)N(c3c(F)cc(C#Cc4ccccc4)cc3F)C(=O)N1CCN(c1cnn(C)c1)C2=O] | (9aS)-7-[2,6-difluoro-4-(2-phenylethynyl)phenyl]-9a-ethyl-2-(1-methylpyrazol-4-yl)-4,9-dihydro-3H-pyrazino[1,2-c]pyrimidine-1,6,8-trione | 104 | 125 |

-continued

List of Examples and data:

| Ex. | Structure | Name | EC$_{50}$ (nM) mGlu4PAM | Eff. (%) |
|---|---|---|---|---|
| 108 | 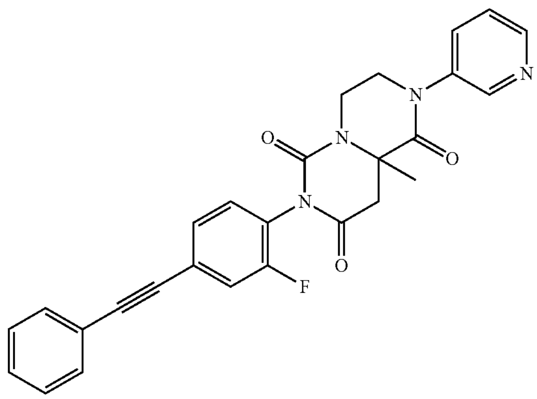 [SMILES: CC12CC(=O)N(c3ccc(C#Cc4ccccc4)cc3F)C(=O)N1CCN(c1cccnc1)C2=O] | (9aRS)-7-[2-fluoro-4-(2-phenylethynyl)phenyl]-9a-methyl-2-(3-pyridyl)-4,9-dihydro-3H-pyrazino[1,2-c]pyrimidine-1,6,8-trione | 267 | 103 |
| 109 | 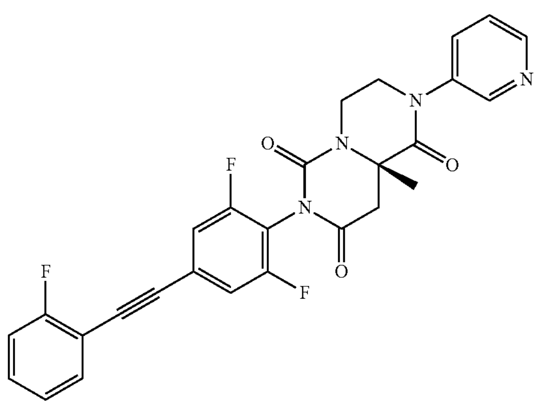 [SMILES: C[C@@]12CC(=O)N(c3c(F)cc(C#Cc4ccccc4F)cc3F)C(=O)N1CCN(c1cccnc1)C2=O] | (9aS)-7-[2,6-difluoro-4-[2-(2-fluorophenyl)ethynyl]phenyl]-9a-methyl-2-(3-pyridyl)-4,9-dihydro-3H-pyrazino[1,2-c]pyrimidine-1,6,8-trione | 56 | 85 |
| 110 | 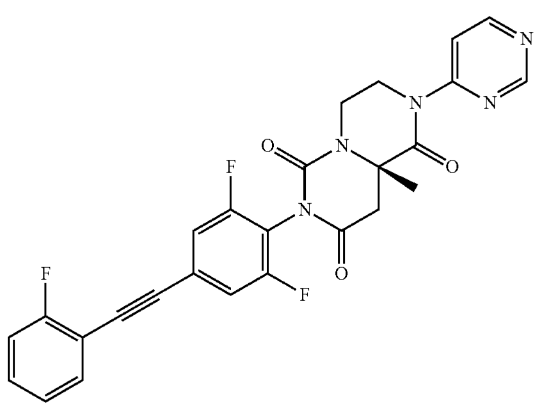 [SMILES: C[C@@]12CC(=O)N(c3c(F)cc(C#Cc4ccccc4F)cc3F)C(=O)N1CCN(c1ccncn1)C2=O] | (9aS)-7-[2,6-difluoro-4-[2-(2-fluorophenyl)ethynyl]phenyl]-9a-methyl-2-pyrimidin-4-yl-4,9-dihydro-3H-pyrazino[1,2-c]pyrimidine-1,6,8-trione | 31 | 90 |

List of Examples and data:

| Ex. | Structure | Name | EC$_{50}$ (nM) mGlu4PAM | Eff. (%) |
|---|---|---|---|---|
| 111 | 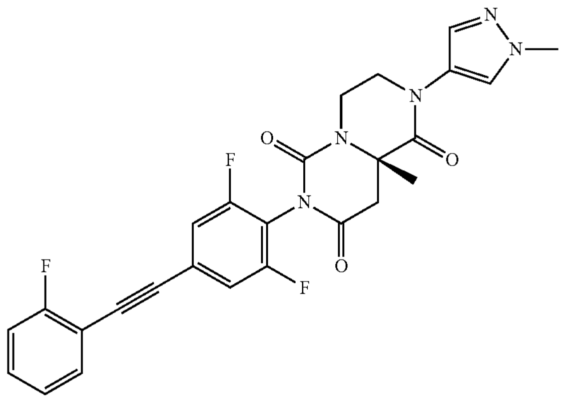 [SMILES: Cn1cc(N2CCN3C(=O)N(c4c(F)cc(C#Cc5ccccc5F)cc4F)C(=O)C[C@@]3(C)C2=O)cn1] | (9aS)-7-[2,6-difluoro-4-[2-(2-fluorophenyl)ethynyl]phenyl]-9a-methyl-2-(1-methylpyrazol-4-yl)-4,9-dihydro-3H-pyrazino[1,2-c]pyrimidine-1,6,8-trione | 56 | 120 |
| 112 | 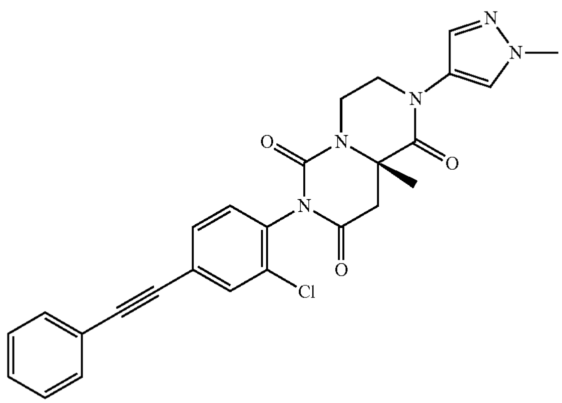 [SMILES: Cn1cc(N2CCN3C(=O)N(c4ccc(C#Cc5ccccc5)cc4Cl)C(=O)C[C@@]3(C)C2=O)cn1] | (9aS)-7-[2-chloro-4-(2-phenylethynyl)phenyl]-9a-methyl-2-(1-methyl-pyrazol-4-yl)-4,9-dihydro-3H-pyrazino[1,2-c]pyrimidine-1,6,8-trione | | |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention:

Tablets of the following composition are produced in a conventional manner:

|  | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Experimental Section

Example 1

(9aRS)-7-[2,6-difluoro-4-(2-phenylethynyl)phenyl]-2-(3-pyridyl)-3,4,9,9a-tetrahydropyrazino[1,2-c]pyrimidine-1,6,8-trione

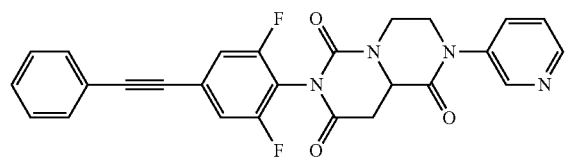 [SMILES: O=C1C2CC(=O)N(c3c(F)cc(C#Cc4ccccc4)cc3F)C(=O)N2CCN1c1cccnc1]

Step 1: 2,6-Difluoro-4-phenylethynyl-phenylamine

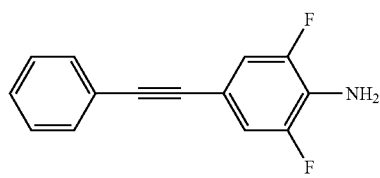

Bis-(triphenylphosphine)-palladium(II)dichloride (826 mg, 1.18 mmol, 0.02 equiv.) was dissolved in 100 ml THF. 2,6-Difluoro-4-iodoaniline (15 g, 58.8 mmol) and phenylacetylene (7.2 g, 7.8 ml, 70.6 mmol, 1.2 equiv.) were added at room temperature. Triethylamine (29.8 g, 41 ml, 0.29 mol, 5 equiv.), triphenylphosphine (617 mg, 2.35 mmol, 0.04 equiv.) and copper(I)iodide (112 mg, 0.58 mmol, 0.01 equiv.) were added and the mixture was stirred for 1 hour at 60° C.

The reaction mixture was cooled and extracted with saturated NaHCO$_3$ solution and two times with ethyl acetate. The organic layers were washed three times with water, dried over sodium sulfate and evaporated to dryness. The crude product was purified by flash chromatography on a silica gel column eluting with an ethyl acetate:heptane gradient 0:100 to 40:60. The desired 2,6-difluoro-4-phenylethynyl-phenylamine (12.6 g, 93% yield) was obtained as a yellow solid, MS: m/e=230.1 (M+H$^+$).

Step 2: (9aRS)-7-[2,6-difluoro-4-(2-phenylethynyl)phenyl]-3,4,9,9a-tetrahydro-2H-pyrazino[1,2-c]pyrimidine-1,6,8-trione

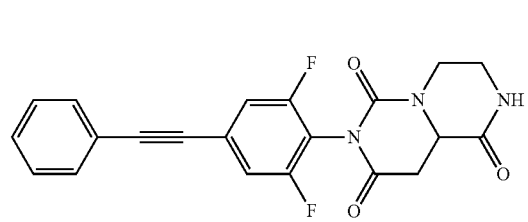

In a 6 ml closed vessel were introduced 2,6-Difluoro-4-phenylethynyl-phenylamine (Example 1, step 1) (100 mg, 0.44 mmol), and toluene (2.5 ml). Carbonyl diimidazole (149 mg, 0.92 mmol, 2.1 equiv.) was added at room temperature. The mixture was stirred for 40 min at 115° C. To the mixture ethyl 2-(3-oxopiperazin-2-yl)acetate [Abelman & al., Tetrahedron Lett. 44,1823 (2003)](81 mg, 0.44 mmol, 1.0 equiv.) were added and stirred for 16 hours at 115° C. The reaction mixture was cooled, concentrated in vaccuo and loaded directly onto a silica gel column. The crude product was purified by flash chromatography eluting with a 10:90 to 100:0 ethyl acetate:heptane gradient. The title compound (50 mg, 29% yield) was obtained as a light yellow solid, MS: m/e=396.1 (M+H$^+$).

Step 3: (9aRS)-7-[2,6-difluoro-4-(2-phenylethynyl)phenyl]-2-(3-pyridyl)-3,4,9,9a-tetrahydropyrazino[1,2-c]pyrimidine-1,6,8-trione (9aRS)-7-[2,6-difluoro-4-(2-phenylethynyl)phenyl]-3,4,9,9a-tetrahydro-2H-pyrazino[1,2-c]pyrimidine-1,6,8-trione (70 mg, 0.177 mmol) was dissolved in dioxane (2.0 ml). Cs$_2$CO$_3$ (115 mg, 0.354 mmol, 2.0 equiv.), 3-bromopyridine (31 mg, 0.195 mmol, 1.1 equiv.), palladium (II) acetate (8.0 mg, 0.035 mmol, 0.2 equiv.) and 4,5-bis(diphenylphosphino)-9,9-dimethylxanthene [Xantphos®] (30.7 mg, 0.053 mmol, 0.3 equiv.) were added at room temperature. The mixture was stirred for 4 hours at 110° C. The reaction mixture was evaporated and loaded directly onto a silica gel column. The crude product was purified by flash chromatography eluting with an ethyl acetate:heptane 0:100 to 100:0 gradient. The title compound (47 mg, 56% yield) was obtained as a white solid, MS: m/e=473.2 (M+H+).

Example 2

(9aRS)-7-[2,6-difluoro-4-(2-phenylethynyl)phenyl]-2-pyrimidin-4-yl-3,4,9,9a-tetrahydropyrazino[1,2-c]pyrimidine-1,6,8-trione

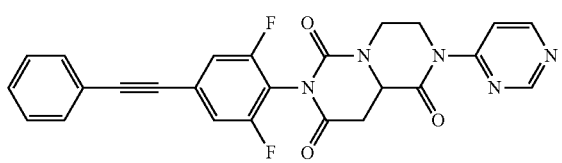 [SMILES: O=C1C2CC(=O)N(c3c(F)cc(C#Cc4ccccc4)cc3F)C(=O)N2CCN1c1ccncn1]

The title compound was obtained as a white solid, MS: m/e=474.2 (M+H$^+$), using chemistry similar to that described in example 1, step 3, from (9aRS)-7-[2,6-difluoro-4-(2-phenylethynyl)phenyl]-3,4,9,9a-tetrahydro-2H- pyrazino[1,2-c]pyrimidine-1,6,8-trione (Example 1, step 2) and 4-bromopyrimidine hydrochloride.

Example 3

(9aRS)-7-[2,6-difluoro-4-(2-phenylethynyl)phenyl]-2-(2-pyridyl)-3,4,9,9a-tetrahydropyrazino[1,2-c]pyrimidine-1,6,8-trione

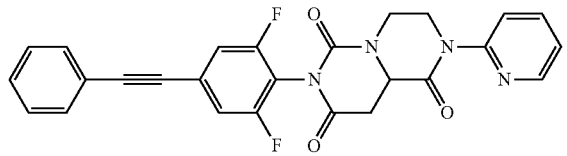 [SMILES: CC12CC(=O)N(c3c(F)cc(C#Cc4ccccc4)cc3F)C(=O)N1CCN(c1ccccn1)C2=O]

The title compound was obtained as a light yellow solid, MS: m/e=473.2 (M+H$^+$), using chemistry similar to that described in example 1, step 3, from (9aRS)-7-[2,6-difluoro-4-(2-phenylethynyl)phenyl]-3,4,9,9a-tetrahydro-2H-pyrazino[1,2-c]pyrimidine-1,6,8-trione (Example 1, step 2) and 2-bromopyrimidine.

Example 4

(9aRS)-7-[2,6-difluoro-4-(2-phenylethynyl)phenyl]-9a-methyl-2-(2-pyridyl)-4,9-dihydro-3H-pyrazino[1,2-c]pyrimidine-1,6,8-trione

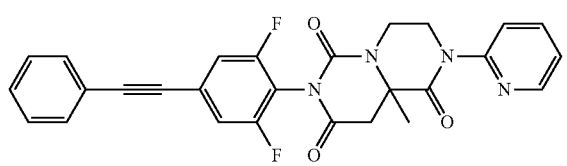

Step 1: (9aRS)-7-[2,6-difluoro-4-(2-phenylethynyl)phenyl]-9a-methyl-2,3,4,9-tetrahydropyrazino[1,2-c]pyrimidine-1,6,8-trione (4.1)

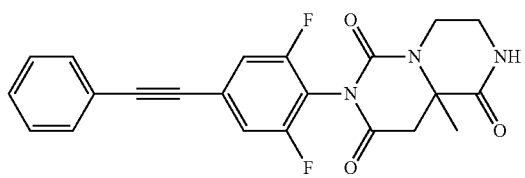

The title compound was obtained as a white solid, MS: m/e=410.2 (M+H$^+$), using chemistry similar to that described in Example 1, step 2 from 2,6-difluoro-4-phenylethynyl-phenylamine (Example 1, step 1) and methyl 2-[(2RS)-2-methyl-3-oxo-piperazin-2-yl]acetate [Abelman & al., Tetrahedron Lett. 44,1823 (2003)].

Step 2: (9aS)- and (9aR)-7-[2,6-difluoro-4-(2-phenylethynyl)phenyl]-9a-methyl-2,3,4,9-tetrahydropyrazino[1,2-c]pyrimidine-1,6,8-triones (4.2a & 4.2b)

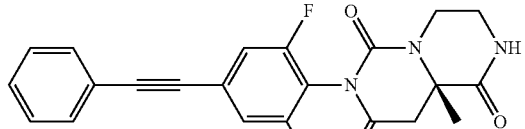

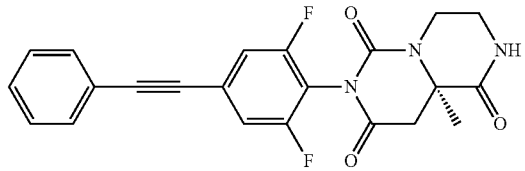

Chiral separation of the enantiomers was realized by chiral HPLC using a Chiralpak IE column using (hexane/EtOH/DCM/Et$_2$N—70/20/10/0.1%) to obtain (9aS)-7-[2,6-difluoro-4-(2-phenylethynyl)phenyl]-9a-methyl-2,3,4,9-tetrahydropyrazino[1,2-c]pyrimidine-1,6,8-trione (4.2a) as an off-white solid (MS: 410.1 (M+H$^+$)); and (9aR)-7-[2,6-difluoro-4-(2-phenylethynyl)phenyl]-9a-methyl-2,3,4,9-tetrahydropyrazino[1,2-c]pyrimidine-1,6,8-trione (4.2b) as an off-white solid (MS: 410.1 (M+H$^+$)).

Step 2: (9aRS)-7-[2,6-difluoro-4-(2-phenylethynyl)phenyl]-9a-methyl-2-(2-pyridyl)-4,9-dihydro-3H-pyrazino[1,2-c]pyrimidine-1,6,8-trione The title compound was obtained as a light yellow solid, MS: m/e=487.2 (M+H$^+$), using chemistry similar to that described in example 1, step 3, from (9aRS)-7-[2,6-difluoro-4-(2-phenylethynyl)phenyl]-9a-methyl-2,3,4,9-tetrahydropyrazino[1,2-c]pyrimidine-1,6,8-trione (4.1) (Example 4, step 1) and 2-bromopyridine.

Example 5

(9aS)-7-[2,6-difluoro-4-(2-phenylethynyl)phenyl]-9a-methyl-2-(2-pyridyl)-4,9-dihydro-3H-pyrazino[1,2-c]pyrimidine-1,6,8-trione

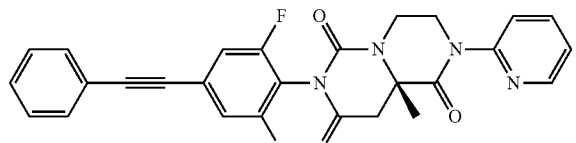

(9aS)-7-[2,6-difluoro-4-(2-phenylethynyl)phenyl]-9a-methyl-2,3,4,9-tetrahydropyrazino[1,2-c]pyrimidine-1,6,8-trione (4.2a) (Example 4, step 2) (60 mg, 0.15 mmol), 2-iodopyridine (60.1 mg, 0.29 mmol, 2.0 equiv.) and K$_2$CO$_3$ (40.5 mg, 0.29 mmol, 2.0 equiv.) were combined with dioxane (1.8 ml) to give a brown suspension. After sonication unter argon for 3 minutes, copper (I) iodide (5.58 mg, 0.29 mmol, 0.2 equiv.), and trans-N,N'-dimethylcyclohexane-1,2-diamine (8.34 mg, 9.27 µl, 0.59 mmol, 0.4 equiv.) were added. The reaction mixture was stirred under argon at 140° C. for 2 h.

The reaction mixture was concentrated in vacuo and absorbed on aminophase silicagel. The crude material was purified by flash chromatography on 20 g of silica gel, eluting with a 20% to 100% EtOAc/heptane gradient. The title compound (46 mg, 65% yield) was obtained as a white solid, MS: m/e=487.3 (M+H⁺).

Example 6

(9aRS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione

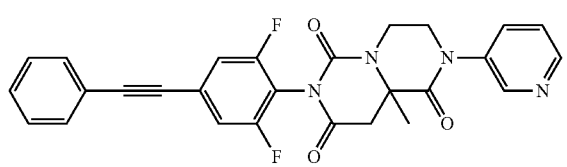 [SMILES: CC12CC(=O)N(c3c(F)cc(C#Cc4ccccc4)cc3F)C(=O)N1CCN(c1cccnc1)C2=O]

The title compound was obtained as an off-white solid, MS: m/e=487.2 (M+H⁺), using chemistry similar to that described in example 5, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 3-bromopyridine.

Example 7

(9aS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione

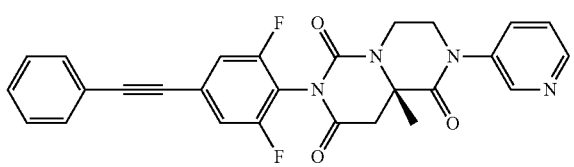 [SMILES: C[C@@]12CC(=O)N(c3c(F)cc(C#Cc4ccccc4)cc3F)C(=O)N1CCN(c1cccnc1)C2=O]

The title compound was obtained as an off-white solid, MS: m/e=487.3 (M+H⁺), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 3-iodopyridine.

Example 8

(9aRS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione

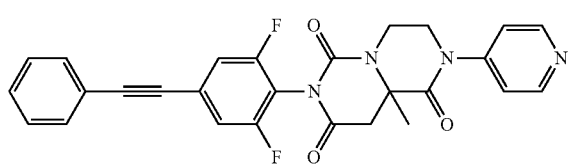

The title compound was obtained as an off-white solid, MS: m/e=487.2 (M+H⁺), using chemistry similar to that described in example 1, step 3, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 4-bromopyridine.

Example 9

(9aS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione

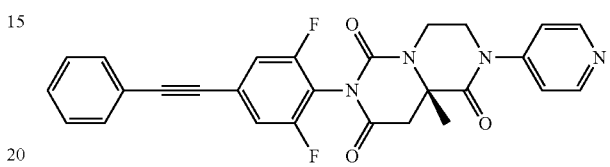

The title compound was obtained as a white solid, MS: m/e=487.3 (M+H⁺), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 4-iodopyridine.

Example 10

(9aRS)-7-[2,6-difluoro-4-(2-phenylethynyl)phenyl]-9a-methyl-2-(6-methyl-2-pyridyl)-4,9-dihydro-3H-pyrazino[1,2-c]pyrimidine-1,6,8-trione

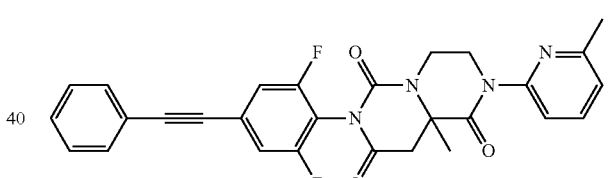

The title compound was obtained as a white solid, MS: m/e=501.2 (M+H⁺), using chemistry similar to that described in example 1, step 3, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 2-bromo-6-methyl pyridine.

Example 11

(9aRS)-7-[2,6-difluoro-4-(2-phenylethynyl)phenyl]-9a-methyl-2-(2-methyl-4-pyridyl)-4,9-dihydro-3H-pyrazino[1,2-c]pyrimidine-1,6,8-trione

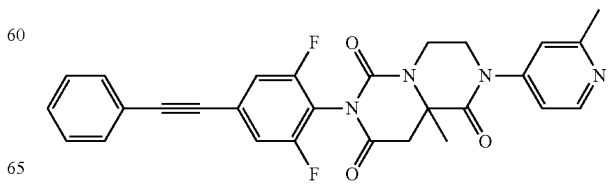

The title compound was obtained as a light yellow solid, MS: m/e=501.3 (M+H⁺), using chemistry similar to that described in example 1, step 3, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 4-bromo-2-methyl pyridine.

Example 12

(9aRS)-7-(2,6-difluoro-4-(phenylethynyl)phenyl)-9a-methyl-2-(4-methylpyridin-2-yl)tetrahydro-1H-pyrazino[1,2-c]pyrimidine-1,6,8(2H,7H)-trione

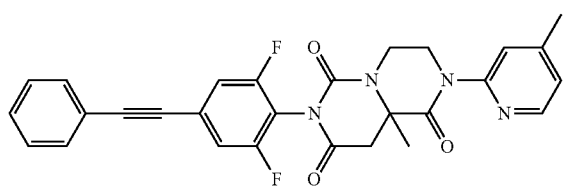

The title compound was obtained as a white solid, MS: m/e=501.2 (M+H⁺), using chemistry similar to that described in example 1, step 3, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 2-bromo-4-methylpyridine.

Example 13

(9aS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione

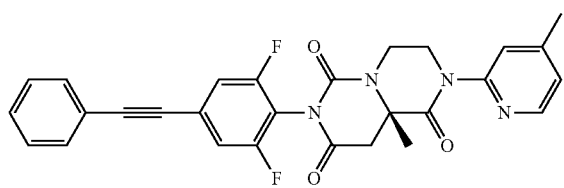 [SMILES: Cc1ccnc(N2CCN3C(=O)N(c4c(F)cc(C#Cc5ccccc5)cc4F)C(=O)C[C@@]3(C)C2=O)c1]

The title compound was obtained as a white solid, MS: m/e=501.3 (M+H⁺), using chemistry similar to that described in example 1, step 3, from (9aS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 2) and 2-bromo-4-methylpyridine.

Example 14

(9aRS)-7-[2,6-difluoro-4-(2-phenylethynyl)phenyl]-9a-methyl-2-(5-methyl-3-pyridyl)-4,9-dihydro-3H-pyrazino[1,2-c]pyrimidine-1,6,8-trione

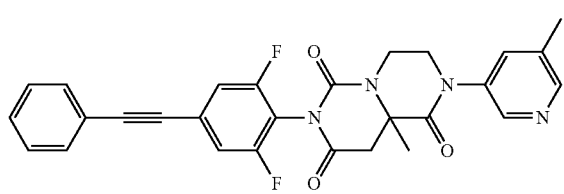 [SMILES: Cc1cncc(N2CCN3C(=O)N(c4c(F)cc(C#Cc5ccccc5)cc4F)C(=O)CC3(C)C2=O)c1]

The title compound was obtained as a white solid, MS: m/e=501.2 (M+H⁺), using chemistry similar to that described in example 1, step 3, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 3-bromo-5-methylpyridine.

Example 15

(9aS)-7-[2,6-difluoro-4-(2-phenylethynyl)phenyl]-9a-methyl-2-(5-methyl-3-pyridyl)-4,9-dihydro-3H-pyrazino[1,2-c]pyrimidine-1,6,8-trione

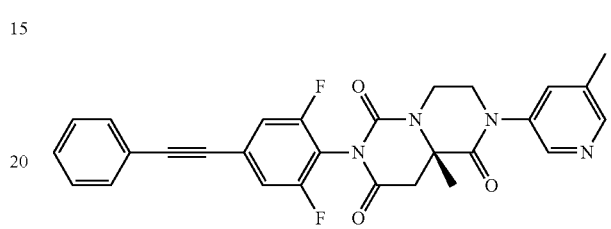

The title compound was obtained as an off-white solid, MS: m/e=501.2 (M+H⁺), using chemistry similar to that described in example 1, step 3, from (9aS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 3-bromo-5-methylpyridine.

Example 16

(9aRS)-7-[2,6-difluoro-4-(2-phenylethynyl)phenyl]-9a-methyl-2-(6-methyl-3-pyridyl)-4,9-dihydro-3H-pyrazino[1,2-c]pyrimidine-1,6,8-trione

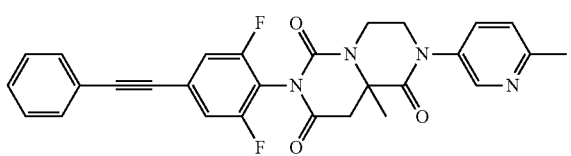 [SMILES: Cc1ccc(N2CCN3C(=O)N(c4c(F)cc(C#Cc5ccccc5)cc4F)C(=O)CC3(C)C2=O)cn1]

The title compound was obtained as a white crystalline solid, MS: m/e=501.3 (M+H⁺), using chemistry similar to that described in example 5, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 5-bromo-2-methylpyridine.

Example 17

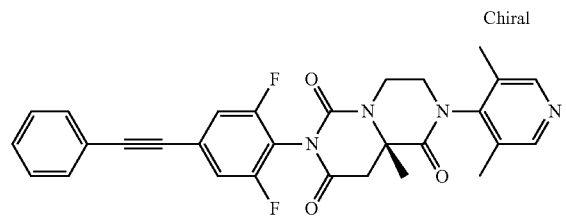 [SMILES: Cc1cncc(C)c1N1CCN2C(=O)N(c3c(F)cc(C#Cc4ccccc4)cc3F)C(=O)C[C@@]2(C)C1=O]

(9aS)-7-[2,6-difluoro-4-(2-phenylethynyl)phenyl]-2-(3,5-dimethyl-4-pyridyl)-9a-methyl-4,9-dihydro-3H-pyrazino[1,2-c]pyrimidine-1,6,8-trione The title compound was obtained as a light yellow solid, MS: m/e=515.2 (M+H⁺), using chemistry similar to that described in example 1, step 3, from (9aS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 2) and 4-bromo-3,5-dimethylpyridine hydrochloride.

Example 18

(9aRS)-2-(2-chloro-4-pyridyl)-7-[2,6-difluoro-4-(2-phenylethynyl)phenyl]-9a-methyl-4,9-dihydro-3H-pyrazino[1,2-c]pyrimidine-1,6,8-trione

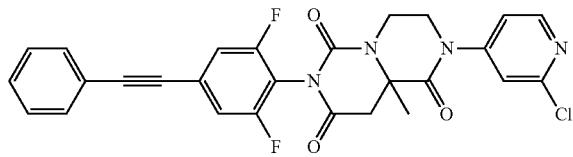

The title compound was obtained as a white solid, MS: m/e=521.2, 523.2 (M+H⁺), using chemistry similar to that described in example 1, step 3, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 2-chloro-4-iodopyridine.

Example 19

(9aS)-2-(2-chloro-4-pyridyl)-7-[2,6-difluoro-4-(2-phenylethynyl)phenyl]-9a-methyl-4,9-dihydro-3H-pyrazino[1,2-c]pyrimidine-1,6,8-trione

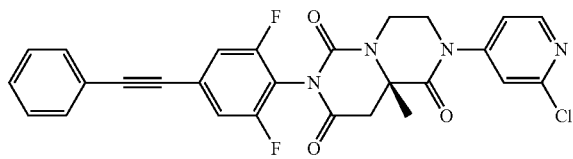 [SMILES: CC12CC(=O)N(c3c(F)cc(C#Cc4ccccc4)cc3F)C(=O)N1CCN(c1ccnc(Cl)c1)C2=O]

The title compound was obtained as a white solid, MS: m/e=521.2, 523.2 (M+H⁺), using chemistry similar to that described in example 1, step 3, from (9aS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 2) and 2-chloro-4-iodopyridine.

Example 20

(9aRS)-2-(6-chloro-3-pyridyl)-7-[2,6-difluoro-4-(2-phenylethynyl)phenyl]-9a-methyl-4,9-dihydro-3H-pyrazino[1,2-c]pyrimidine-1,6,8-trione

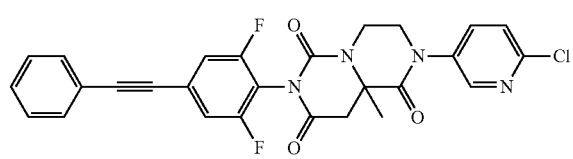 [SMILES: CC12CC(=O)N(c3c(F)cc(C#Cc4ccccc4)cc3F)C(=O)N1CCN(c1ccc(Cl)nc1)C2=O]

The title compound was obtained as a crystalline light yellow crystalline solid, MS: m/e=521.2, 523.2 (M+H⁺), using chemistry similar to that described in example 5, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 2-chloro-5-iodopyridine.

Example 21

(9aS)-2-(6-chloro-3-pyridyl)-7-[2,6-difluoro-4-(2-phenylethynyl)phenyl]-9a-methyl-4,9-dihydro-3H-pyrazino[1,2-c]pyrimidine-1,6,8-trione

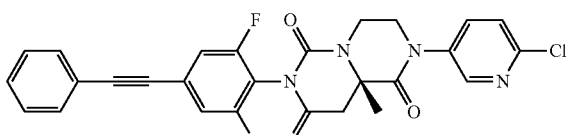

The title compound was obtained as a crystalline light yellow crystalline solid, MS: m/e=521.2, 523.2 (M+H⁺), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 2-chloro-5-iodopyridine.

Example 22

(9aRS)-7-[2,6-difluoro-4-(2-phenylethynyl)phenyl]-2-(6-methoxy-3-pyridyl)-9a-methyl-4,9-dihydro-3H-pyrazino[1,2-c]pyrimidine-1,6,8-trione

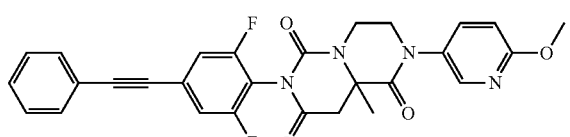

The title compound was obtained as a white crystalline solid, MS: m/e=517.4 (M+H⁺), using chemistry similar to that described in example 5, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 5-iodo-2-methoxypyridine.

Example 23

(9aS)-7-[2,6-difluoro-4-(2-phenylethynyl)phenyl]-2-(6-methoxy-3-pyridyl)-9a-methyl-4,9-dihydro-3H-pyrazino[1,2-c]pyrimidine-1,6,8-trione

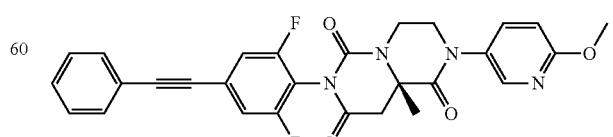

The title compound was obtained as a white crystalline solid, MS: m/e=517.3 (M+H⁺), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 5-iodo-2-methoxypyridine.

Example 24

(9aS)-7-[2,6-difluoro-4-(2-phenylethynyl)phenyl]-9a-methyl-2-(1-methyl-6-oxo-3-pyridyl)-4,9-dihydro-3H-pyrazino[1,2-c]pyrimidine-1,6,8-trione

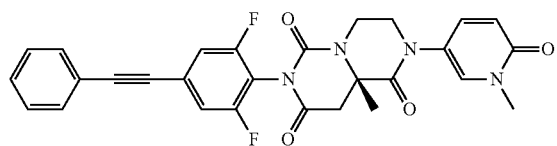

The title compound was obtained as a white crystalline solid, MS: m/e=517.3 (M+H$^+$), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 5-bromo-1-methylpyridin-2(1H)-one.

Example 25

(9aRS)-7-[2,6-difluoro-4-(2-phenylethynyl)phenyl]-9a-methyl-2-pyrimidin-2-yl-4,9-dihydro-3H-pyrazino[1,2-c]pyrimidine-1,6,8-trione

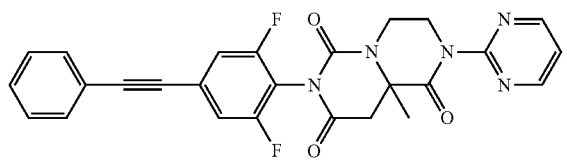 [SMILES: CC12CC(=O)N(c3c(F)cc(C#Cc4ccccc4)cc3F)C(=O)N1CCN(c1ncccn1)C2=O]

The title compound was obtained as a light yellow solid, MS: m/e=488.1 (M+H$^+$), using chemistry similar to that described in example 1, step 3, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 2-bromopyrimidine.

Example 26

(9aRS)-7-[2,6-difluoro-4-(2-phenylethynyl)phenyl]-9a-methyl-2-pyrimidin-4-yl-4,9-dihydro-3H-pyrazino[1,2-c]pyrimidine-1,6,8-trione

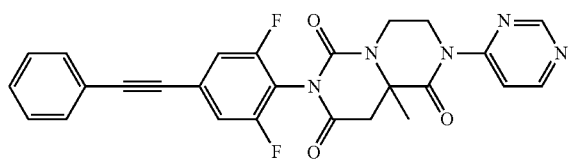 [SMILES: CC12CC(=O)N(c3c(F)cc(C#Cc4ccccc4)cc3F)C(=O)N1CCN(c1ccncn1)C2=O]

The title compound was obtained as a white solid, MS: m/e=488.2 (M+H$^+$), using chemistry similar to that described in example 1, step 3, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 4-bromopyrimidine hydrochloride.

Example 27

(9aS)-7-[2,6-difluoro-4-(2-phenylethynyl)phenyl]-9a-methyl-2-pyrimidin-4-yl-4,9-dihydro-3H-pyrazino[1,2-c]pyrimidine-1,6,8-trione

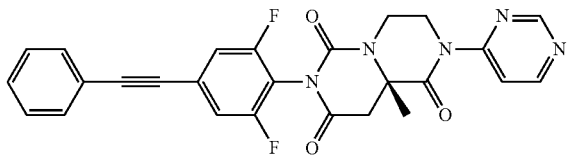 [SMILES: C[C@@]12CC(=O)N(c3c(F)cc(C#Cc4ccccc4)cc3F)C(=O)N1CCN(c1ccncn1)C2=O]

The title compound was obtained as a white crystalline solid, MS: m/e=488.3 (M+H$^+$), using chemistry similar to that described in example 1, step 3, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 4-bromopyrimidine hydrochloride.

Example 28

(9aRS)-7-[2,6-difluoro-4-(2-phenylethynyl)phenyl]-9a-methyl-2-pyrimidin-5-yl-4,9-dihydro-3H-pyrazino[1,2-c]pyrimidine-1,6,8-trione

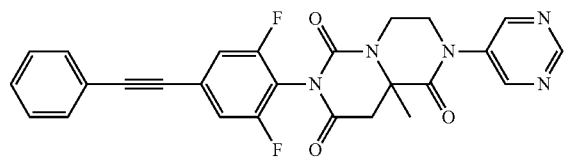

The title compound was obtained as a white solid, MS: m/e=488.2 (M+H$^+$), using chemistry similar to that described in example 1, step 3, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 5-bromopyrimidine.

Example 29

(9aRS)-7-[2,6-difluoro-4-(2-phenylethynyl)phenyl]-2-(2,6-dimethylpyrimidin-4-yl)-9a-methyl-4,9-dihydro-3H-pyrazino[1,2-c]pyrimidine-1,6,8-trione

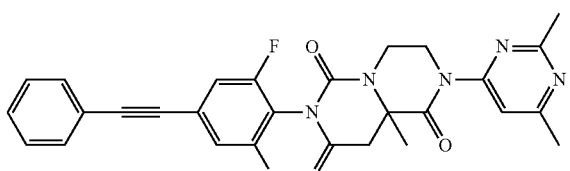

The title compound was obtained as a light yellow solid, MS: m/e=516.2 (M+H+), using chemistry similar to that described in example 1, step 3, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 4-bromo-2,6-dimethylpyrimidine.

Example 30

(9aRS)-7-[2,6-difluoro-4-(2-phenylethynyl)phenyl]-9a-methyl-2-(2-methylpyrimidin-4-yl)-4,9-dihydro-3H-pyrazino[1,2-c]pyrimidine-1,6,8-trione

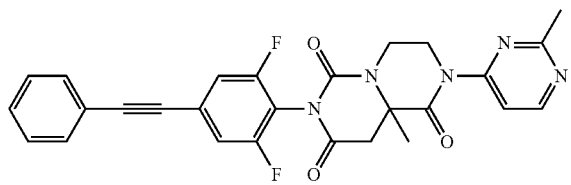 [SMILES: Cc1nccc(N2CCN3C(=O)N(c4c(F)cc(C#Cc5ccccc5)cc4F)C(=O)CC3(C)C2=O)n1]

The title compound was obtained as a white solid, MS: m/e=502.4 (M+H+), using chemistry similar to that described in example 1, step 3, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 4-bromo-2-methylpyrimidine.

Example 31

(9aS)-7-[2,6-difluoro-4-(2-phenylethynyl)phenyl]-9a-methyl-2-(2-methylpyrimidin-4-yl)-4,9-dihydro-3H-pyrazino[1,2-c]pyrimidine-1,6,8-trione

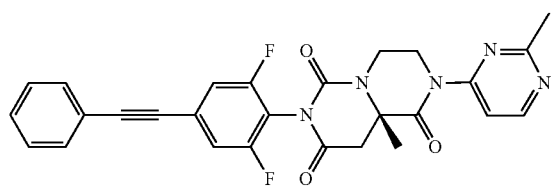 [SMILES: Cc1nccc(N2CCN3C(=O)N(c4c(F)cc(C#Cc5ccccc5)cc4F)C(=O)C[C@@]3(C)C2=O)n1]

The title compound was obtained as a white solid, MS: m/e=502.3 (M+H+), using chemistry similar to that described in example 1, step 3, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 4-bromo-2-methylpyrimidine.

Example 32

(9aRS)-7-[2,6-difluoro-4-(2-phenylethynyl)phenyl]-9a-methyl-2-pyrazin-2-yl-4,9-dihydro-3H-pyrazino[1,2-c]pyrimidine-1,6,8-trione

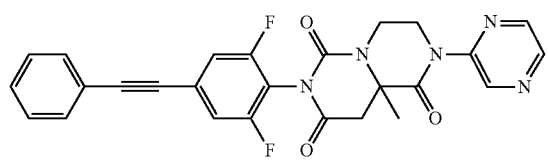 [SMILES: CC12CC(=O)N(c3c(F)cc(C#Cc4ccccc4)cc3F)C(=O)N1CCN(c1cnccn1)C2=O]

The title compound was obtained as a white crystalline solid, MS: m/e=488.2 (M+H+), using chemistry similar to that described in example 1, step 3, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 2-bromopyrazine.

Example 33

(9aS)-7-[2,6-difluoro-4-(2-phenylethynyl)phenyl]-9a-methyl-2-pyrazin-2-yl-4,9-dihydro-3H-pyrazino[1,2-c]pyrimidine-1,6,8-trione

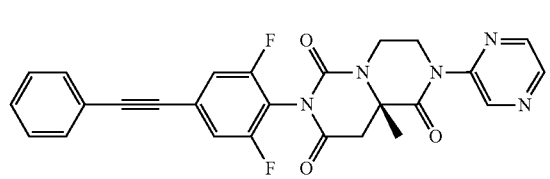 [SMILES: C[C@@]12CC(=O)N(c3c(F)cc(C#Cc4ccccc4)cc3F)C(=O)N1CCN(c1cnccn1)C2=O]

The title compound was obtained as a white solid, MS: m/e=488.4 (M+H+), using chemistry similar to that described in example 1, step 3, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 2-bromopyrazine.

Example 34

(9aRS)-7-[2,6-difluoro-4-(2-phenylethynyl)phenyl]-9a-methyl-2-(6-methylpyrazin-2-yl)-4,9-dihydro-3H-pyrazino[1,2-c]pyrimidine-1,6,8-trione

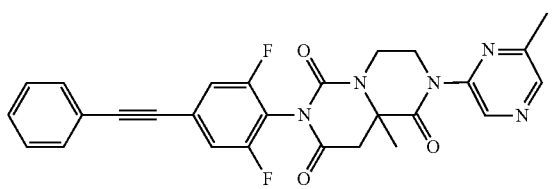 [SMILES: Cc1cncc(N2CCN3C(=O)N(c4c(F)cc(C#Cc5ccccc5)cc4F)C(=O)CC3(C)C2=O)n1]

The title compound was obtained as a white crystalline solid, MS: m/e=502.2 (M+H+), using chemistry similar to that described in example 1, step 3, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 2-bromopyrazine.

Example 35

(9aS)-7-[2,6-difluoro-4-(2-phenylethynyl)phenyl]-9a-methyl-2-(6-methylpyrimidin-4-yl)-4,9-dihydro-3H-pyrazino[1,2-c]pyrimidine-1,6,8-trione

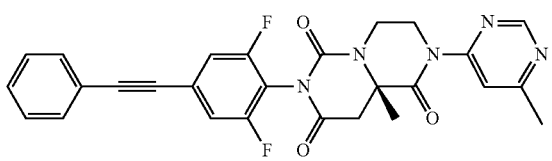 [SMILES: Cc1cc(N2CCN3C(=O)N(c4c(F)cc(C#Cc5ccccc5)cc4F)C(=O)C[C@@]3(C)C2=O)ncn1]

The title compound was obtained as a white solid, MS: m/e=502.2 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 4-bromo-6-methylpyrimidine.

Example 36

(9aS)-7-[2,6-difluoro-4-(2-phenylethynyl)phenyl]-9a-methyl-2-(5-methylpyrimidin-4-yl)-4,9-dihydro-3H-pyrazino[1,2-c]pyrimidine-1,6,8-trione

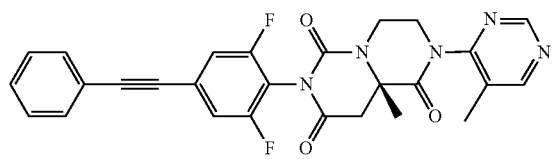 [SMILES: Cc1cncnc1N1CCN2C(=O)N(c3c(F)cc(C#Cc4ccccc4)cc3F)C(=O)C[C@@]2(C)C1=O]

The title compound was obtained as a white solid, MS: m/e=502.3 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 4-bromo-6-methylpyrimidine.

Example 37

(9aS)-7-[2,6-difluoro-4-(2-phenylethynyl)phenyl]-2-(2-methoxypyrimidin-5-yl)-9a-methyl-4,9-dihydro-3H-pyrazino[1,2-c]pyrimidine-1,6,8-trione

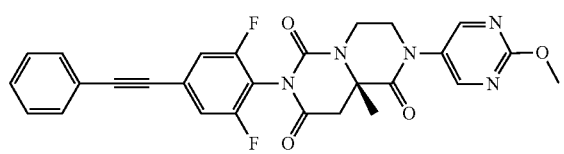 [SMILES: COc1ncc(N2CCN3C(=O)N(c4c(F)cc(C#Cc5ccccc5)cc4F)C(=O)C[C@@]3(C)C2=O)cn1]

The title compound was obtained as a light yellow solid, MS: m/e=518.3 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 5-bromo-2-methoxypyrimidine.

Example 38

(9aS)-2-(2-tert-butoxypyrimidin-5-yl)-7-[2,6-difluoro-4-(2-phenylethynyl)phenyl]-9a-methyl-4,9-dihydro-3H-pyrazino[1,2-c]pyrimidine-1,6,8-trione

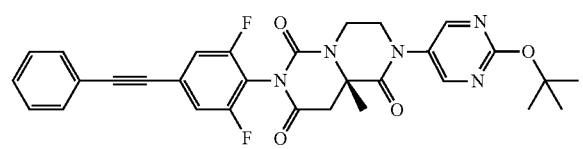 [SMILES: CC(C)(C)Oc1ncc(N2CCN3C(=O)N(c4c(F)cc(C#Cc5ccccc5)cc4F)C(=O)C[C@@]3(C)C2=O)cn1]

The title compound was obtained as a white solid, MS: m/e=504.3 ([M-tBu]+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 5-bromo-2-(tert-butoxy)pyrimidine.

Example 39

(9aS or 9aR)-7-[2,6-difluoro-4-(2-phenylethynyl)phenyl]-2-(2-ethoxypyrimidin-5-yl)-9a-methyl-4,9-dihydro-3H-pyrazino[1,2-c]pyrimidine-1,6,8-trione

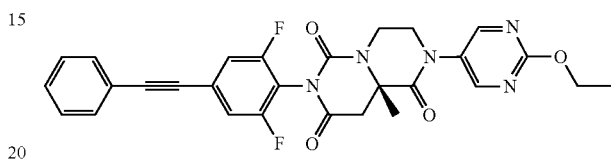

The title compound was obtained as a white solid, MS: m/e=532.3 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 5-bromo-2-ethoxypyrimidine.

Example 40

(9aS)-7-[2,6-difluoro-4-(2-phenylethynyl)phenyl]-2-(2-isopropoxypyrimidin-5-yl)-9a-methyl-4,9-dihydro-3H-pyrazino[1,2-c]pyrimidine-1,6,8-trione

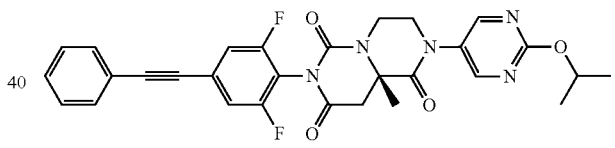

The title compound was obtained as a light yellow solid, MS: m/e=546.3 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 5-bromo-2-isopropoxypyrimidine.

Example 41

(9aS)-2-(2-benzyloxypyrimidin-5-yl)-7-[2,6-difluoro-4-(2-phenylethynyl)phenyl]-9a-methyl-4,9-dihydro-3H-pyrazino[1,2-c]pyrimidine-1,6,8-trione

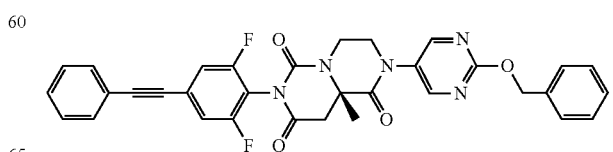

The title compound was obtained as a light yellow solid, MS: m/e=594.3 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 2-(benzyloxy)-5-bromopyrimidine.

Example 42

(9aS)-7-[2,6-difluoro-4-(2-phenylethynyl)phenyl]-2-(2-hydroxypyrimidin-5-yl)-9a-methyl-4,9-dihydro-3H-pyrazino[1,2-c]pyrimidine-1,6,8-trione

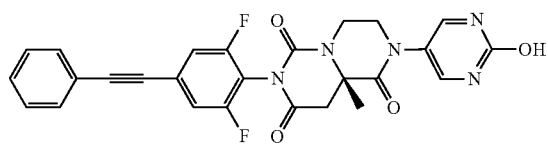 [SMILES: C[C@@]12CC(=O)N(c3c(F)cc(C#Cc4ccccc4)cc3F)C(=O)N1CCN(c1cnc(O)nc1)C2=O]

(9aS)-7-[2,6-difluoro-4-(2-phenylethynyl)phenyl]-2-(2-methoxypyrimidin-5-yl)-9a-methyl-4,9-dihydro-3H-pyrazino[1,2-c]pyrimidine-1,6,8-trione (Example 36) (60 mg, 0.116 mmol) was dissolved in chloroform (3.0 ml). A solution of 0.139 ml (0.139 mmol, 1.2 eq.) of a 1M solution of boron tribromide in dichloromethane in 0.5 ml of chloroform was added over a period of 5 min. The mixture was stirred for 3.5 h at room temperature, and then quenched by the addition of 5% $NaHCO_3$ solution (0.6 ml). The reaction mixture was diluted with 30 ml of ethyl acetate and evaporated. This operation was repeated twice. The crude product was purified by flash chromatography eluting with an ethyl acetate:heptane 50:50 to 100:0 gradient, then with MeOH:ethyl acetate 6:94, then with MeOH:dichloromethane 15:85. The title compound (19 mg, 33% yield) was obtained as a light yellow solid, MS: m/e=504.2 (M+H+).

Example 43

(9aS)-2-[2-(cyclopropoxy)pyrimidin-5-yl]-7-[2,6-difluoro-4-(2-phenylethynyl)phenyl]-9a-methyl-4,9-dihydro-3H-pyrazino[1,2-c]pyrimidine-1,6,8-trione

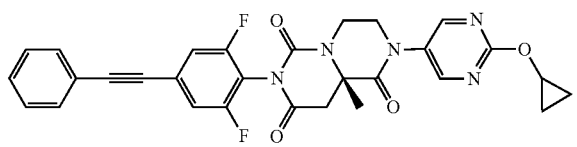 [SMILES: C[C@@]12CC(=O)N(c3c(F)cc(C#Cc4ccccc4)cc3F)C(=O)N1CCN(c1cnc(OC3CC3)nc1)C2=O]

The title compound was obtained as a white solid, MS: m/e=544.2 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 5-bromo-2-cyclopropoxypyrimidine.

Example 44

(9aS)-7-[2,6-difluoro-4-(2-phenylethynyl)phenyl]-2-(5-methoxypyrazin-2-yl)-9a-methyl-4,9-dihydro-3H-pyrazino[1,2-c]pyrimidine-1,6,8-trione

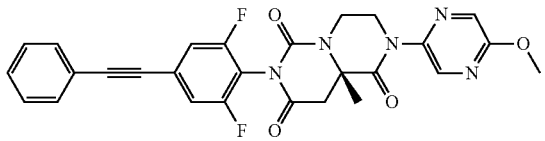 [SMILES: COc1cnc(N2CCN3C(=O)N(c4c(F)cc(C#Cc5ccccc5)cc4F)C(=O)C[C@@]3(C)C2=O)cn1]

The title compound was obtained as a light yellow crystalline solid, MS: m/e=518.3 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 2-bromo-5-methoxypyrazine.

Example 45

(9aS)-2-(5-benzyloxypyrazin-2-yl)-7-[2,6-difluoro-4-(2-phenylethynyl)phenyl]-9a-methyl-4,9-dihydro-3H-pyrazino[1,2-c]pyrimidine-1,6,8-trione

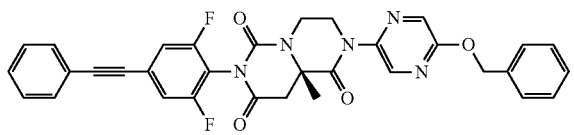 [SMILES: C[C@@]12CC(=O)N(c3c(F)cc(C#Cc4ccccc4)cc3F)C(=O)N1CCN(c1cnc(OCc3ccccc3)cn1)C2=O]

The title compound was obtained as a light yellow solid, MS: m/e=594.3 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 2-(benzyloxy)-5-bromopyrazine.

Example 46

(9aRS)-7-[2,6-difluoro-4-(2-phenylethynyl)phenyl]-9a-methyl-2-pyridazin-3-yl-4,9-dihydro-3H-pyrazino[1,2-c]pyrimidine-1,6,8-trione

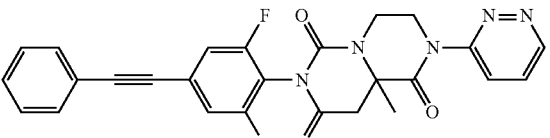

The title compound was obtained as a light yellow crystalline solid, MS: m/e=488.3 (M+H+), using chemistry similar to that described in example 5, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 3-iodopyridazine.

Example 47

(9aS)-7-[2,6-difluoro-4-(2-phenylethynyl)phenyl]-9a-methyl-2-pyrazin-2-yl-4,9-dihydro-3H-pyrazino[1,2-c]pyrimidine-1,6,8-trione

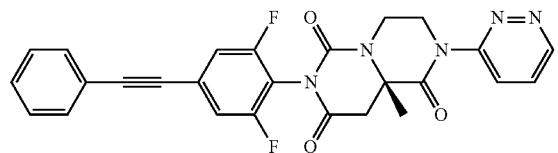 [SMILES: C[C@@]12CC(=O)N(c3c(F)cc(C#Cc4ccccc4)cc3F)C(=O)N1CCN(c1cccnn1)C2=O]

The title compound was obtained as an off-white solid, MS: m/e=488.3 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 3-iodopyridazine.

Example 48

(9aRS)-7-[2,6-difluoro-4-(2-phenylethynyl)phenyl]-9a-methyl-2-(6-methylpyridazin-3-yl)-4,9-dihydro-3H-pyrazino[1,2-c]pyrimidine-1,6,8-trione

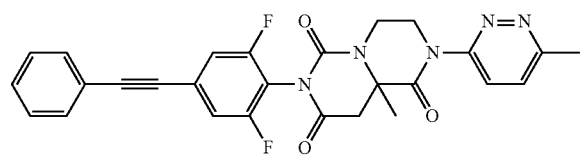 [SMILES: Cc1ccc(N2CCN3C(=O)N(c4c(F)cc(C#Cc5ccccc5)cc4F)C(=O)CC3(C)C2=O)nn1]

The title compound was obtained as a white solid, MS: m/e=502.2 (M+H+), using chemistry similar to that described in example 1, step 3, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 3-iodo-6-methylpyridazine.

Example 49

(9aS)-7-[2,6-difluoro-4-(2-phenylethynyl)phenyl]-9a-methyl-2-(1-methyl-6-oxo-pyridazin-3-yl)-4,9-dihydro-3H-pyrazino[1,2-c]pyrimidine-1,6,8-trione

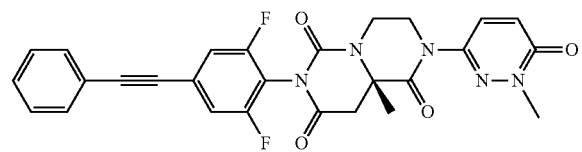

The title compound was obtained as a light yellow crystalline solid, MS: m/e=518.3 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 6-bromo-2-methylpyridazin-3(2H)-one (CAS: 1123169-25-4).

Example 50

(9aRS)-7-[2,6-difluoro-4-(2-phenylethynyl)phenyl]-9a-methyl-2-pyridazin-4-yl-4,9-dihydro-3H-pyrazino[1,2-c]pyrimidine-1,6,8-trione

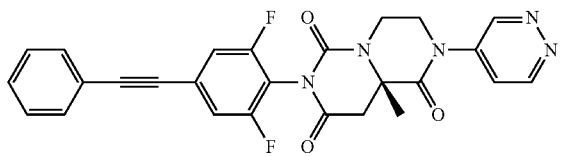 [SMILES: C[C@@]12CC(=O)N(c3c(F)cc(C#Cc4ccccc4)cc3F)C(=O)N1CCN(c1ccnnc1)C2=O]

The title compound was obtained as a yellow solid, MS: m/e=488.2 (M+H+), using chemistry similar to that described in example 5, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 4-bromopyridazine hydrobromide.

Example 51

(9aRS)-7-[2,6-difluoro-4-(2-phenylethynyl)phenyl]-9a-methyl-2-(1-methyl-6-oxo-pyridazin-4-yl)-4,9-dihydro-3H-pyrazino[1,2-c]pyrimidine-1,6,8-trione

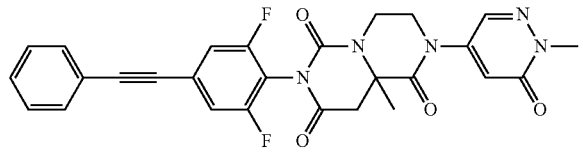

The title compound was obtained as a light red solid, MS: m/e=518.2 (M+H+), using chemistry similar to that described in example 1, step 3, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 5-iodo-2-methylpyridazin-3 (2H)-one (CAS: 153239-91-9).

Example 52

(9aRS)-7-[2,6-difluoro-4-(2-phenylethynyl)phenyl]-9a-methyl-2-thiazol-2-yl-4,9-dihydro-3H-pyrazino[1,2-c]pyrimidine-1,6,8-trione

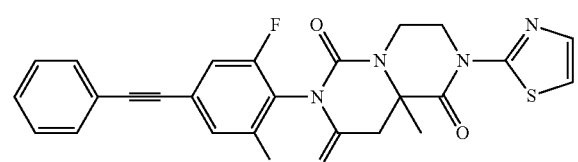

The title compound was obtained as a light yellow crystalline solid, MS: m/e=493.1 (M+H+), using chemistry similar to that described in example 1, step 3, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 2-bromothiazole.

Example 53

(9aRS)-7-[2,6-difluoro-4-(2-phenylethynyl)phenyl]-9a-methyl-2-(5-methylthiazol-2-yl)-4,9-dihydro-3H-pyrazino[1,2-c]pyrimidine-1,6,8-trione

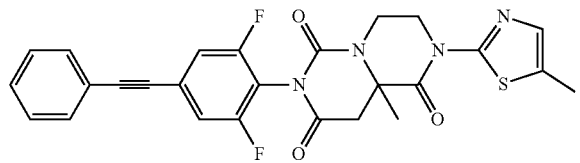 [SMILES: Cc1cnc(N2CCN3C(=O)N(c4c(F)cc(C#Cc5ccccc5)cc4F)C(=O)CC3(C)C2=O)s1]

The title compound was obtained as a white solid, MS: m/e=507.1 (M+H+), using chemistry similar to that described in example 1, step 3, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 2-bromo-5-methylthiazole.

Example 54

(9aRS)-7-[2,6-difluoro-4-(2-phenylethynyl)phenyl]-9a-methyl-2-(4-methylthiazol-2-yl)-4,9-dihydro-3H-pyrazino[1,2-c]pyrimidine-1,6,8-trione

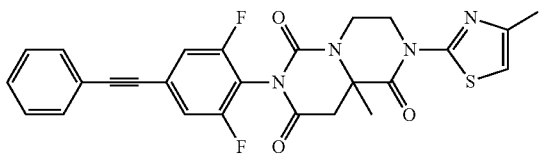 [SMILES: Cc1csc(N2CCN3C(=O)N(c4c(F)cc(C#Cc5ccccc5)cc4F)C(=O)CC3(C)C2=O)n1]

The title compound was obtained as a yellow solid, MS: m/e=507.1 (M+H+), using chemistry similar to that described in example 1, step 3, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 2-bromo-4-methylthiazole.

Example 55

2-[(9aRS)-7-[2,6-difluoro-4-(2-phenylethynyl)phenyl]-9a-methyl-1,6,8-trioxo-4,9-dihydro-3H-pyrazino[1,2-c]pyrimidin-2-yl]thiazole-4-carbonitrile

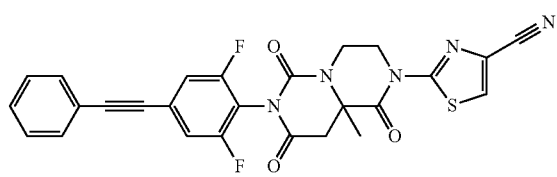 [SMILES: CC12CC(=O)N(c3c(F)cc(C#Cc4ccccc4)cc3F)C(=O)N1CCN(c1nc(C#N)cs1)C2=O]

The title compound was obtained as a light yellow solid, MS: m/e=518.1 (M+H+), using chemistry similar to that described in example 1, step 3, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 2-bromothiazole-4-carbonitrile.

Example 56

(9aRS)-7-[2,6-difluoro-4-(2-phenylethynyl)phenyl]-9a-methyl-2-[4-(trifluoromethyl)thiazol-2-yl]-4,9-dihydro-3H-pyrazino[1,2-c]pyrimidine-1,6,8-trione The title compound was obtained as a yellow solid, MS: m/e=561.1 (M+H+), using chemistry similar to that described in example 1, step 3, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 2-bromo-4-(trifluoromethyl)thiazole.

Example 57

(9aRS)-7-[2,6-difluoro-4-(2-phenylethynyl)phenyl]-9a-methyl-2-[5-(trifluoromethyl)thiazol-2-yl]-4,9-dihydro-3H-pyrazino[1,2-c]pyrimidine-1,6,8-trione The title compound was obtained as a light yellow solid, MS: m/e=561.1 (M+H+), using chemistry similar to that described in example 1, step 3, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 2-bromo-5-(trifluoromethyl)thiazole.

Example 58

(9aRS)-7-[2,6-difluoro-4-(2-phenylethynyl)phenyl]-9a-methyl-2-(1-methylimidazol-4-yl)-4,9-dihydro-3H-pyrazino[1,2-c]pyrimidine-1,6,8-trione The title compound was obtained as a light yellow solid, MS: m/e=490.2 (M+H+), using chemistry similar to that described in example 5, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 4-bromo-1-methyl-1H-imidazole.

Example 59

(9aRS)-7-[2,6-difluoro-4-(2-phenylethynyl)phenyl]-2-(1,4-dimethylimidazol-2-yl)-9a-methyl-4,9-dihydro-3H-pyrazino[1,2-c]pyrimidine-1,6,8-trione

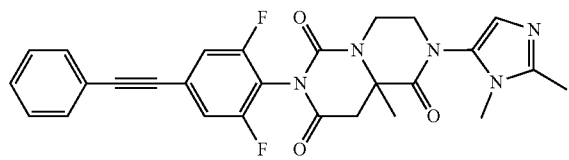 [SMILES: Cc1ncc(N2CCN3C(=O)N(c4c(F)cc(C#Cc5ccccc5)cc4F)C(=O)CC3(C)C2=O)n1C]

The title compound was obtained as a light yellow solid, MS: m/e=504.2 (M+H+), using chemistry similar to that described in example 5, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 2-bromo-1,4-dimethyl-1H-imidazole.

Example 60

(9aRS)-7-[2,6-difluoro-4-(2-phenylethynyl)phenyl]-2-(1,2-dimethylimidazol-4-yl)-9a-methyl-4,9-dihydro-3H-pyrazino[1,2-c]pyrimidine-1,6,8-trione

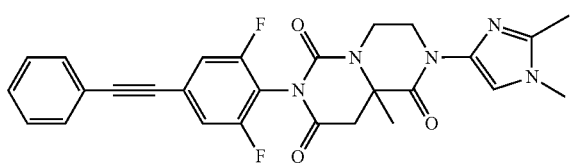 [SMILES: Cc1nc(N2CCN3C(=O)N(c4c(F)cc(C#Cc5ccccc5)cc4F)C(=O)CC3(C)C2=O)cn1C]

The title compound was obtained as a light yellow solid, MS: m/e=504.2 (M+H+), using chemistry similar to that described in example 5, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 4-bromo-1,2-dimethyl-1H-imidazole.

Example 61

(9aS)-7-[2,6-difluoro-4-(2-phenylethynyl)phenyl]-9a-methyl-2-[2-methyl-1-(2,2,2-trifluoroethyl)imidazol-4-yl]-4,9-dihydro-3H-pyrazino[1,2-c]pyrimidine-1,6,8-trione

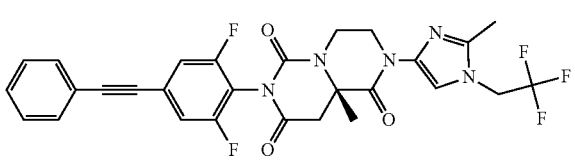 [SMILES: Cc1nc(N2CCN3C(=O)N(c4c(F)cc(C#Cc5ccccc5)cc4F)C(=O)C[C@@]3(C)C2=O)cn1CC(F)(F)F]

The title compound was obtained as a white solid, MS: m/e=572.2 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 4-iodo-2-methyl-1-(2,2,2-trifluoroethyl)-1H-imidazole.

Example 62

(9aRS)-7-[2,6-difluoro-4-(2-phenylethynyl)phenyl]-9a-methyl-2-(1-methylpyrazol-3-yl)-4,9-dihydro-3H-pyrazino[1,2-c]pyrimidine-1,6,8-trione

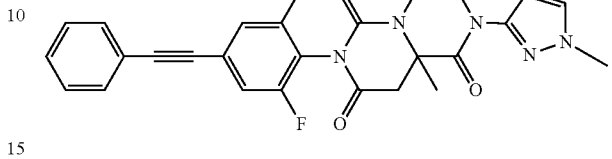

The title compound was obtained as a white solid, MS: m/e=490.2 (M+H+), using chemistry similar to that described in example 5, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 3-bromo-1-methyl-1H-pyrazole.

Example 63

(9aS)-7-[2,6-difluoro-4-(2-phenylethynyl)phenyl]-9a-methyl-2-(1-methylpyrazol-3-yl)-4,9-dihydro-3H-pyrazino[1,2-c]pyrimidine-1,6,8-trione

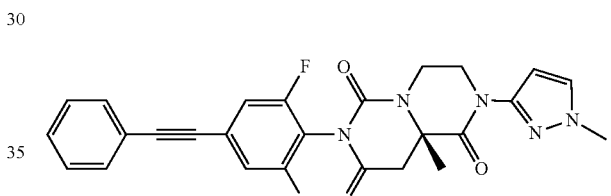

The title compound was obtained as a white solid, MS: m/e=490.2 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 3-bromo-1-methyl-1H-pyrazole.

Example 64

(9aRS)-7-[2,6-difluoro-4-(2-phenylethynyl)phenyl]-9a-methyl-2-(2-methylpyrazol-3-yl)-4,9-dihydro-3H-pyrazino[1,2-c]pyrimidine-1,6,8-trione

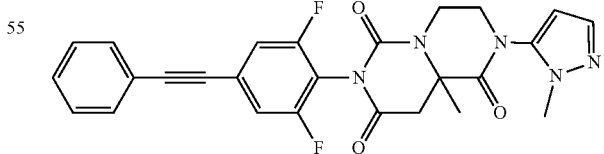

The title compound was obtained as a white crystalline solid, MS: m/e=490.2 (M+H+), using chemistry similar to that described in example 5, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 5-iodo-1-methyl-1H-pyrazole.

Example 65

(9aS)-7-[2,6-difluoro-4-(2-phenylethynyl)phenyl]-9a-methyl-2-(2-methylpyrazol-3-yl)-4,9-dihydro-3H-pyrazino[1,2-c]pyrimidine-1,6,8-trione

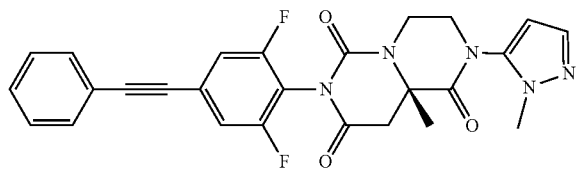 [SMILES: Cn1nccc1N1CCN2C(=O)N(c3c(F)cc(C#Cc4ccccc4)cc3F)C(=O)C[C@@]2(C)C1=O]

The title compound was obtained as a white crystalline solid, MS: m/e=490.2 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 5-iodo-1-methyl-1H-pyrazole.

Example 66

(9aRS)-7-[2,6-difluoro-4-(2-phenylethynyl)phenyl]-2-(2,5-dimethylpyrazol-3-yl)-9a-methyl-4,9-dihydro-3H-pyrazino[1,2-c]pyrimidine-1,6,8-trione

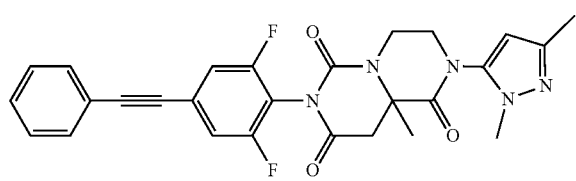 [SMILES: Cc1cc(N2CCN3C(=O)N(c4c(F)cc(C#Cc5ccccc5)cc4F)C(=O)CC3(C)C2=O)n(C)n1]

The title compound was obtained as a white solid, MS: m/e=504.2 (M+H+), using chemistry similar to that described in example 5, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 5-bromo-1,3-dimethyl-1H-pyrazole.

Example 67

(9aRS)-7-[2,6-difluoro-4-(2-phenylethynyl)phenyl]-9a-methyl-2-(1-methylpyrazol-4-yl)-4,9-dihydro-3H-pyrazino[1,2-c]pyrimidine-1,6,8-trione

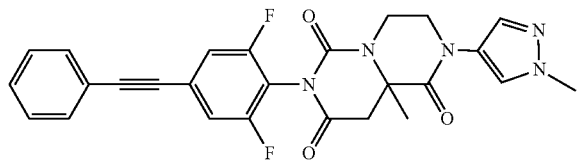

The title compound was obtained as a light yellow solid, MS: m/e=490.2 (M+H+), using chemistry similar to that described in example 5, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 3-bromo-1-methyl-1H-pyrazole.

Example 68

(9aS)-7-[2,6-difluoro-4-(2-phenylethynyl)phenyl]-9a-methyl-2-(1-methylpyrazol-4-yl)-4,9-dihydro-3H-pyrazino[1,2-c]pyrimidine-1,6,8-trione

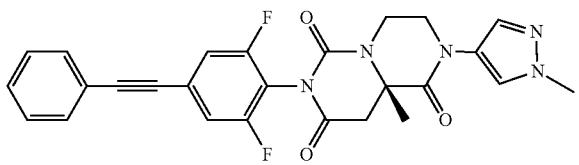 [SMILES: Cn1cc(N2CCN3C(=O)N(c4c(F)cc(C#Cc5ccccc5)cc4F)C(=O)CC3(C)C2=O)cn1]

The title compound was obtained as a white crystalline solid, MS: m/e=490.3 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 3-bromo-1-methyl-1H-pyrazole.

Example 69

(9aS)-7-[2,6-difluoro-4-(2-phenylethynyl)phenyl]-2-(1-ethylpyrazol-4-yl)-9a-methyl-4,9-dihydro-3H-pyrazino[1,2-c]pyrimidine-1,6,8-trione

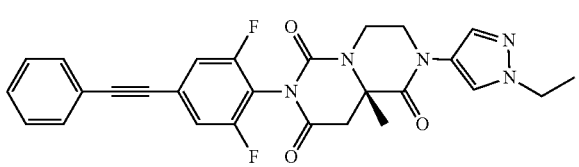 [SMILES: CC(C)n1cc(N2CCN3C(=O)N(c4c(F)cc(C#Cc5ccccc5)cc4F)C(=O)C[C@@]3(C)C2=O)cn1]

The title compound was obtained as a white crystalline solid, MS: m/e=504.3 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 1-ethyl-4-iodo-1H-pyrazole.

Example 70

(9aS)-7-[2,6-difluoro-4-(2-phenylethynyl)phenyl]-2-(1-isopropylpyrazol-4-yl)-9a-methyl-4,9-dihydro-3H-pyrazino[1,2-c]pyrimidine-1,6,8-trione

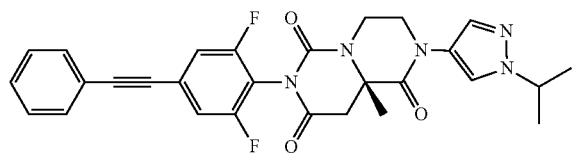

The title compound was obtained as a white crystalline solid, MS: m/e=518.3 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 1-isopropyl-4-iodo-1H-pyrazole.

Example 71

(9aS)-7-[2,6-difluoro-4-(2-phenylethynyl)phenyl]-9a-methyl-2-(1H-pyrazol-4-yl)-4,9-dihydro-3H-pyrazino[1,2-c]pyrimidine-1,6,8-trione

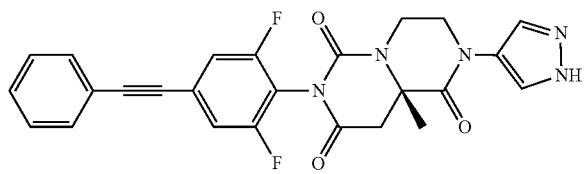 [SMILES: C[C@@]12CC(=O)N(c3c(F)cc(C#Cc4ccccc4)cc3F)C(=O)N1CCN(c1cn[nH]c1)C2=O]

Step 1: (9aS)-7-[2,6-difluoro-4-(2-phenylethynyl)phenyl]-9a-methyl-2-[1-(2-trimethylsilylethoxymethyl)pyrazol-4-yl]-4,9-dihydro-3H-pyrazino[1,2-c]pyrimidine-1,6,8-trione

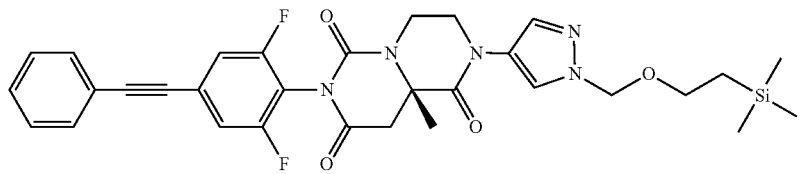 [SMILES: C[C@@]12CC(=O)N(c3c(F)cc(C#Cc4ccccc4)cc3F)C(=O)N1CCN(c1cnn(COCC[Si](C)(C)C)c1)C2=O]

The title compound was obtained as a white solid, using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 4-iodo-1-((2-(trimethylsilyl)ethoxy)methyl)-1H-pyrazole (CAS: [220299-49-0]).

Step 2: (9aS)-7-[2,6-difluoro-4-(2-phenylethynyl)phenyl]-9a-methyl-2-(1H-pyrazol-4-yl)-4,9-dihydro-3H-pyrazino[1,2-c]pyrimidine-1,6,8-trione To a well stirred solution of (9aS)-7-[2,6-difluoro-4-(2-phenylethynyl)phenyl]-9a-methyl-2-[1-(2-trimethylsilylethoxymethyl)pyrazol-4-yl]-4,9-dihydro-3H-pyrazino[1,2-c]pyrimidine-1,6,8-trione (85 mg, 0.140 mmol) in 2 ml of dioxane was added 0.35 ml (1.4 mmol, 10 eq.) of a 4M solution of HCl in dioxane. The reaction was stirred for 4 h at 55° C. and 16 h at r.t. The solution was adjusted to >8 by addition of 25% ammonium hydroxide solution (0.48 ml, 3.08 mmol, 22 eq.) and concentrated in vaccuo. The residue was taken up in ethyl acetate. The organic phase was washed with water, and concentrated in vaccuo. The crude material was purified by flash chromatography over SiO$_2$ (20 g) using 50:50 to 0:100 heptane-ethyl acetate gradient followed by 4% MeOH in ethyl acetate as eluent. The title compound (43 mg, 64% yield) was obtained as a white solid, MS: m/e=476.2 (M+H$^+$).

Example 72

(9aS)-7-[2,6-difluoro-4-(2-phenylethynyl)phenyl]-2-[1-(3-methoxypropyl)pyrazol-4-yl]-9a-methyl-4,9-dihydro-3H-pyrazino[1,2-c]pyrimidine-1,6,8-trione To a solution of (9aS)-7-[2,6-difluoro-4-(2-phenylethynyl)phenyl]-9a-methyl-2-(1H-pyrazol-4-yl)-4,9-dihydro-3H-pyrazino[1,2-c]pyrimidine-1,6,8-trione (36 mg, 0.076 mmol) in DMF (2 ml) were added at 0° C. a 60% suspension of sodium hydride in mineral oil (3.9 mg, 0.1 mmol, 1.3 eq.). The reaction was stirred for 5 min and 1-bromo-3-methoxypropane (12.7 mg, 9.3 μl, 0.083 mmol, 1.1 eq.) was added.

The yellow solution was warmed to r.t. and stirred for 2 h. The reaction mixture was quenched with water. After standard work-up with ethyl acetate/water the organic layers were dried over MgSO$_4$ and concentrated in vacuo. The crude material was purified by flash chromatography (SiO$_2$ (20 g)) using a 50% to 100% ethyl acetate in heptane gradient. The title compound (16 mg, 39% yield) was obtained as an off-white solid, MS: m/e=548.2 (M+H$^+$).

Example 73

(9aS)-7-[2,6-difluoro-4-(2-phenylethynyl)phenyl]-9a-methyl-2-(1-methyl-1,2,4-triazol-3-yl)-4,9-dihydro-3H-pyrazino[1,2-c]pyrimidine-1,6,8-trione

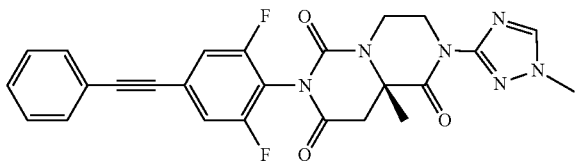 [SMILES: Cn1cnc(N2CCN3C(=O)N(c4c(F)cc(C#Cc5ccccc5)cc4F)C(=O)C[C@@]3(C)C2=O)n1]

The title compound was obtained as a white crystalline solid, MS: m/e=491.2 (M+H+), using chemistry similar to that described in example 5, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 3-iodo-1-methyl-1H-1,2,4-triazole.

Example 74

(9aRS)-7-[2-chloro-6-fluoro-4-(2-phenylethynyl)phenyl]-9a-methyl-2-(3-pyridyl)-4,9-dihydro-3H-pyrazino[1,2-c]pyrimidine-1,6,8-trione

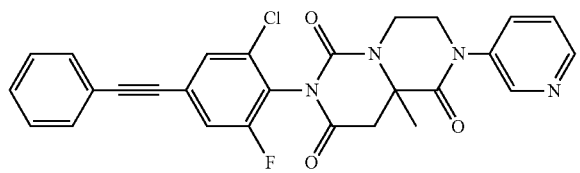 [SMILES: CC12CC(=O)N(c3c(F)cc(C#Cc4ccccc4)cc3Cl)C(=O)N1CCN(c1cccnc1)C2=O]

Step 1:
2-chloro-6-fluoro-4-phenylethynyl-phenylamine

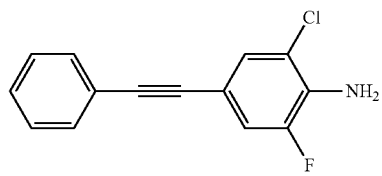 [SMILES: Nc1c(F)cc(C#Cc2ccccc2)cc1Cl]

The title compound was obtained as an orange solid, MS: m/e=246.1, 248.1 (M+H$^+$), using chemistry similar to that described in example 1, step 1 from 2-chloro-6-fluoro-4-iodoaniline and phenylacetylene.

Step 2: (9aRS)-7-[2-chloro-6-fluoro-4-(2-phenylethynyl)phenyl]-9a-methyl-2,3,4,9-tetrahydropyrazino[1,2-c]pyrimidine-1,6,8-trione

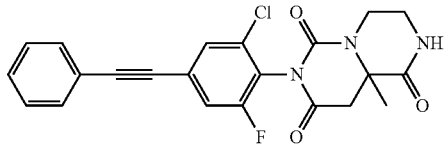

The title compound was obtained as a white solid, MS: m/e=424.3, 426.2 (M+H$^+$), using chemistry similar to that described in Example 1, step 2 from 2-chloro-6-fluoro-4-phenylethynyl-phenylamine (Example 73, step 1) and methyl 2-[(2RS)-2-methyl-3-oxo-piperazin-2-yl]acetate.

Step 3: (9aRS)-7-[2-chloro-6-fluoro-4-(2-phenylethynyl)phenyl]-9a-methyl-2-(3-pyridyl)-4,9-dihydro-3H-pyrazino[1,2-c]pyrimidine-1,6,8-trione The title compound was obtained as a light yellow solid, MS: m/e=503.2, 505.2 (M+H$^+$), using chemistry similar to that described in example 5, from (9aRS)-7-[2-chloro-6-fluoro-4-(2-phenylethynyl)phenyl]-9a-methyl-2,3,4,9-tetrahydropyrazino[1,2-c]pyrimidine-1,6,8-trione (Example 73, step 2) and 3-iodopyridine.

Example 75

(9aRS)-7-[2-chloro-6-fluoro-4-(2-phenylethynyl)phenyl]-9a-methyl-2-(4-pyridyl)-4,9-dihydro-3H-pyrazino[1,2-c]pyrimidine-1,6,8-trione

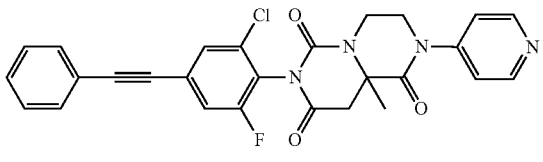 [SMILES: CC12CC(=O)N(c3c(F)cc(C#Cc4ccccc4)cc3Cl)C(=O)N1CCN(c1ccncc1)C2=O]

The title compound was obtained as a light brown solid, MS: m/e=503.2, 505.2 (M+H$^+$), using chemistry similar to that described in example 5, from (9aRS)-7-[2-chloro-6-fluoro-4-(2-phenylethynyl)phenyl]-9a-methyl-2,3,4,9-tetrahydropyrazino[1,2-c]pyrimidine-1,6,8-trione (Example 73, step 2) and 4-iodopyridine.

Example 76

(9aRS)-7-[2-chloro-6-fluoro-4-(2-phenylethynyl)phenyl]-9a-methyl-2-(2-pyridyl)-4,9-dihydro-3H-pyrazino[1,2-c]pyrimidine-1,6,8-trione

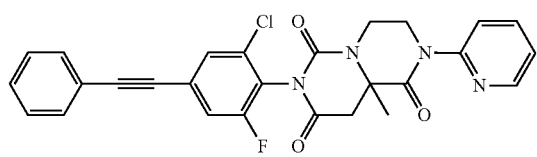 [SMILES: CC12CC(=O)N(c3c(F)cc(C#Cc4ccccc4)cc3Cl)C(=O)N1CCN(c1ccccn1)C2=O]

The title compound was obtained as a white solid, MS: m/e=503.2, 505.1 (M+H$^+$), using chemistry similar to that described in example 5, from (9aRS)-7-[2-chloro-6-fluoro-4-(2-phenylethynyl)phenyl]-9a-methyl-2,3,4,9-tetrahydropyrazino[1,2-c]pyrimidine-1,6,8-trione (Example 73, step 2) and 2-iodopyridine.

Example 77

(9aRS)-7-[2-chloro-6-fluoro-4-(2-phenylethynyl)phenyl]-9a-methyl-2-(4-pyridyl)-4,9-dihydro-3H-pyrazino[1,2-c]pyrimidine-1,6,8-trione

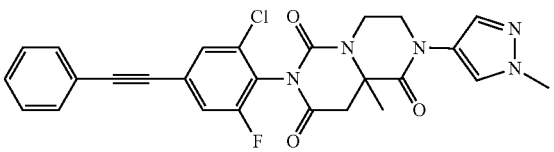 [SMILES: Cn1cc(N2CCN3C(=O)N(c4c(F)cc(C#Cc5ccccc5)cc4Cl)C(=O)CC3(C)C2=O)cn1]

The title compound was obtained as an off-white solid, MS: m/e=506.2, 508.2 (M+H$^+$), using chemistry similar to that described in example 5, from (9aRS)-7-[2-chloro-6-fluoro-4-(2-phenylethynyl)phenyl]-9a-methyl-2,3,4,9-tetrahydropyrazino[1,2-c]pyrimidine-1,6,8-trione (Example 73, step 2) and 4-iodo-1-methyl-1H-pyrazole.

Example 78

(9aS)-7-[2-chloro-6-fluoro-4-(2-phenylethynyl)phenyl]-9a-methyl-2-(4-pyridyl)-4,9-dihydro-3H-pyrazino[1,2-c]pyrimidine-1,6,8-trione

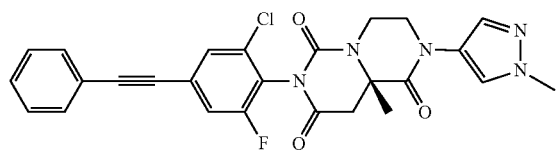 [SMILES: Cn1cc(N2CCN3C(=O)N(c4c(F)cc(C#Cc5ccccc5)cc4Cl)C(=O)C[C@@]3(C)C2=O)cn1]

Using similar separation techniques as described in example 4, step 2; chiral separation of the enantiomers was realized by chiral HPLC using a Chiralpak AD column using (heptane/EtOH/NH$_4$OAc—60/39.9/0.1%) as eluent to obtain (9aS)-7-[2-chloro-6-fluoro-4-(2-phenylethynyl)phenyl]-9a-methyl-2-(4-pyridyl)-4,9-dihydro-3H-pyrazino[1,2-c]pyrimidine-1,6,8-trione (1:1 mixture of stable atropisomers) as a light brown solid, MS: m/e=506.3, 508.2 (M+H$^+$); as well as (9aR)-7-[2-chloro-6-fluoro-4-(2-phenylethynyl)phenyl]-9a-methyl-2-(4-pyridyl)-4,9-dihydro-3H-pyrazino[1,2-c]pyrimidine-1,6,8-trione (1 stable atropisomer=entity A) as a light brown solid (MS: 506.2, 508.2 (M+H$^+$)); and (9aR)-7-[2-chloro-6-fluoro-4-(2-phenylethynyl)phenyl]-9a-methyl-2-(4-pyridyl)-4,9-dihydro-3H-pyrazino[1,2-c]pyrimidine-1,6,8-trione (Istable atropisomer=entity B) as a light brown solid (MS: 506.2, 508.1 (M+H$^+$)).

Example 79

(9aS)-7-[2,6-difluoro-4-(2-phenylethynyl)phenyl]-2-(2-methoxyethyl)-9a-methyl-4,9-dihydro-3H-pyrazino[1,2-c]pyrimidine-1,6,8-trione

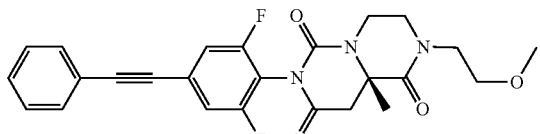

To a solution of (9aS)-7-[2,6-difluoro-4-(2-phenylethynyl)phenyl]-9a-methyl-2-(1H-pyrazol-4-yl)-4,9-dihydro-3H-pyrazino[1,2-c]pyrimidine-1,6,8-trione (60 mg, 0.147 mmol) in DMF (2 ml) were added at 0° C. a 60% suspension of sodium hydride in mineral oil (12 mg, 0.3 mmol, 2 eq.). The reaction was stirred for 10 min and 2-bromo-2-methoxyethane (61 mg, 42 µl, 0.44 mmol, 3 eq.) were added. The solution was stirred for 2 h at 0° C. and then warmed to r.t and stirred for 1 h. The reaction mixture was quenched with water. After standard work-up with ethyl acetate/water the organic layers were dried over MgSO$_4$ and concentrated in vacuo. The crude material was purified by flash chromatography (SiO$_2$ (20 g)) using a 20% to 100% ethyl acetate in heptane gradient. The title compound (18 mg, 26% yield) was obtained as a white solid, MS: m/e=468.2 (M+H$^+$).

Example 80

(9aS)-7-[2,6-difluoro-4-(2-phenylethynyl)phenyl]-2-(3-methoxypropyl)-9a-methyl-4,9-dihydro-3H-pyrazino[1,2-c]pyrimidine-1,6,8-trione

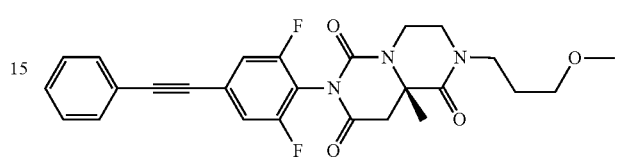

The title compound was obtained as a white crystalline solid, MS: m/e=482.2 (M+H+), using chemistry similar to that described in example 79, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 1-bromo-3-methoxypropane.

Example 81

(9aS)-7-[2,6-difluoro-4-(2-phenylethynyl)phenyl]-9a-methyl-2-(2,2,2-trifluoroethyl)-4,9-dihydro-3H-pyrazino[1,2-c]pyrimidine-1,6,8-trione

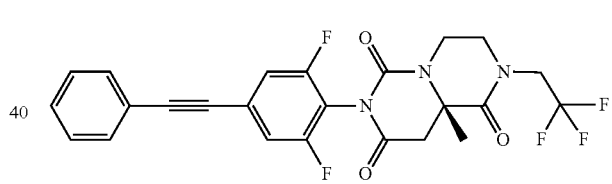

To a solution of (9aS)-7-[2,6-difluoro-4-(2-phenylethynyl)phenyl]-9a-methyl-2-(1H-pyrazol-4-yl)-4,9-dihydro-3H-pyrazino[1,2-c]pyrimidine-1,6,8-trione (60 mg, 0.147 mmol) and 2,2,2-trifluoroethyl trifluoromethanesulfonate (61 mg, 38 µl, 0.26 mmol, 1.8 eq.) in DMF (2 ml) were added at r.t. K$_2$CO$_3$ (61 mg, 0.44 mmol, 3 eq.). The reaction was stirred for 10 min and 2-bromo-2-methoxyethane (61 mg, 42 µl, 0.44 mmol, 3 eq.) were added. The solution was stirred for 1 h at r.t. and then warmed to 65° C. and stirred for 6 h. Then 2,2,2-trifluoroethyl trifluoromethane-sulfonate (20 µl) was added and the reaction was stirred for 16 h at 65° C. Another 20 µl of 2,2,2-trifluoroethyl trifluoromethanesulfonate were added and the mixture was stirred for 1 h at 65° C. The reaction mixture was quenched with water. After standard work-up with ethyl acetate/water the organic layers were dried over MgSO$_4$ and concentrated in vacuo. The crude material was purified and separated from unreacted starting material by flash chromatography (SiO$_2$ (20 g)) using a 10% to 100% ethyl acetate in heptane gradient. The title compound was obtained as a white crystalline solid, MS: m/e=492.2 (M+H+).

Example 82

Ethyl 4-[(9aS)-7-[2,6-difluoro-4-(2-phenylethynyl)phenyl]-9a-methyl-1,6,8-trioxo-4,9-dihydro-3H-pyrazino[1,2-c]pyrimidin-2-yl]butanoate

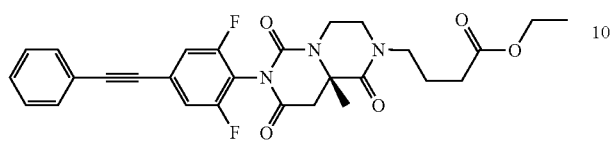

To a solution of (9aS)-7-[2,6-difluoro-4-(2-phenylethynyl)phenyl]-9a-methyl-2-(1H-pyrazol-4-yl)-4,9-dihydro-3H-pyrazino[1,2-c]pyrimidine-1,6,8-trione (Example 4, step 2) (55 mg, 0.134 mmol) and ethyl 4-bromobutanoate (52 mg, 39 µl, 0.27 mmol, 2.0 eq.) in DMF (1.5 ml) were added at r.t. $Cs_2CO_3$ (88 mg, 0.27 mmol, 2.0 eq.). The reaction was stirred for 16 h at 70° C. The reaction mixture was quenched with water. After standard work-up with ethyl acetate/water the organic layers were dried over $MgSO_4$ and concentrated in vacuo. The crude material was purified and separated from unreacted starting material by flash chromatography ($SiO_2$ (20 g)) using a 10% to 100% ethyl acetate in heptane gradient. The title compound was obtained as a light yellow waxy solid, MS: m/e=524.3 (M+H+).

Example 83

(9aRS)-7-[2,6-difluoro-4-(2-phenylethynyl)phenyl]-9a-methyl-2-(m-tolylmethyl)-4,9-dihydro-3H-pyrazino[1,2-c]pyrimidine-1,6,8-trione

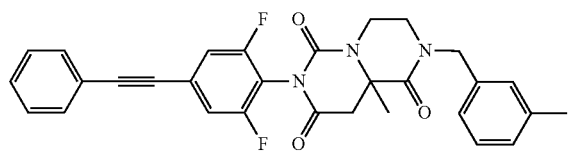 [SMILES: Cc1cccc(CN2CCN3C(=O)N(c4c(F)cc(C#Cc5ccccc5)cc4F)C(=O)CC3(C)C2=O)c1]

To a solution of (9aRS)-7-[2,6-difluoro-4-(2-phenylethynyl)phenyl]-9a-methyl-2-(1H-pyrazol-4-yl)-4,9-dihydro-3H-pyrazino[1,2-c]pyrimidine-1,6,8-trione (Example 4, step 1) (50 mg, 0.122 mmol) and 1-(bromomethyl)-3-methylbenzene (27 mg, 20 µl, 0.147 mmol, 1.2 eq.) in DMF (1.8 ml) were added at r.t. $Cs_2CO_3$ (80 mg, 0.24 mmol, 2.0 eq.). The reaction was stirred for 24 h at r.t. The reaction mixture was quenched with water. After standard work-up with ethyl acetate/water the organic layers were dried over $MgSO_4$ and concentrated in vacuo. The crude material was purified and separated from unreacted starting material by flash chromatography ($SiO_2$ (20 g)) using a 10% to 80% ethyl acetate in heptane gradient. The title compound (59 mg, 94%) was obtained as a white solid, MS: m/e=514.3 (M+H+).

Example 84

(9aRS)-7-[2,6-difluoro-4-(2-phenylethynyl)phenyl]-9a-methyl-2-(p-tolylmethyl)-4,9-dihydro-3H-pyrazino[1,2-c]pyrimidine-1,6,8-trione

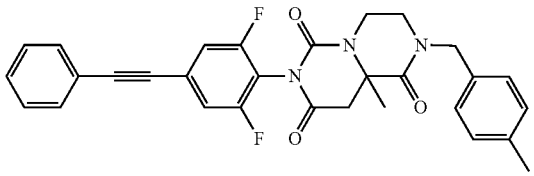 [SMILES: Cc1ccc(CN2CCN3C(=O)N(c4c(F)cc(C#Cc5ccccc5)cc4F)C(=O)CC3(C)C2=O)cc1]

The title compound was obtained as a white crystalline solid, MS: m/e=514.3 (M+H+), using chemistry similar to that described in Example 83, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 1-(bromomethyl)-4-methylbenzene.

Example 85

(9aRS)-7-[2,6-difluoro-4-(2-phenylethynyl)phenyl]-9a-methyl-2-(o-tolylmethyl)-4,9-dihydro-3H-pyrazino[1,2-c]pyrimidine-1,6,8-trione

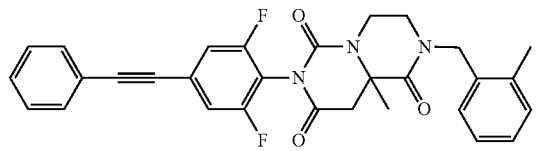 [SMILES: Cc1ccccc1CN1CCN2C(=O)N(c3c(F)cc(C#Cc4ccccc4)cc3F)C(=O)CC2(C)C1=O]

The title compound was obtained as a white crystalline solid, MS: m/e=514.3 (M+H+), using chemistry similar to that described in Example 83, from (9aRS)-7-[2,6-difluoro-4-(2-phenylethynyl)phenyl]-9a-methyl-2,3,4,9-tetrahydro-pyrazino[1,2-c]pyrimidine-1,6,8-trione (Example 4, step 1) and 1-(bromomethyl)-2-methylbenzene.

Example 86

(9aRS)-7-[2,6-difluoro-4-(2-phenylethynyl)phenyl]-2-[(2,6-dimethylphenyl)methyl]-9a-methyl-4,9-dihydro-3H-pyrazino[1,2-c]pyrimidine-1,6,8-trione

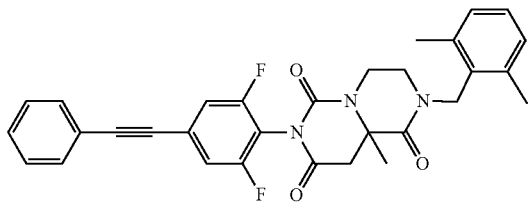 [SMILES: Cc1cccc(C)c1CN1CCN2C(=O)N(c3c(F)cc(C#Cc4ccccc4)cc3F)C(=O)CC2(C)C1=O]

The title compound was obtained as a white solid, MS: m/e=528.4 (M+H+), using chemistry similar to that described in Example 83, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 2-(bromomethyl)-1,3-dimethylbenzene.

Example 87

(9aRS)-2-[(2-chlorophenyl)methyl]-7-[2,6-difluoro-4-(2-phenylethynyl)phenyl]-9a-methyl-4,9-dihydro-3H-pyrazino[1,2-c]pyrimidine-1,6,8-trione

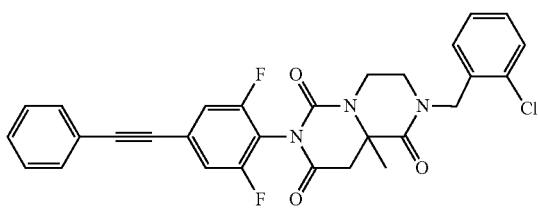 [SMILES: CC12CC(=O)N(c3c(F)cc(C#Cc4ccccc4)cc3F)C(=O)N1CCN(Cc1ccccc1Cl)C2=O]

The title compound was obtained as a white solid, MS: m/e=534.3, 536.3 (M+H+), using chemistry similar to that described in Example 83, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 1-(bromomethyl)-2-chlorobenzene.

Example 88

(9aRS)-2-[(3-chlorophenyl)methyl]-7-[2,6-difluoro-4-(2-phenylethynyl)phenyl]-9a-methyl-4,9-dihydro-3H-pyrazino[1,2-c]pyrimidine-1,6,8-trione

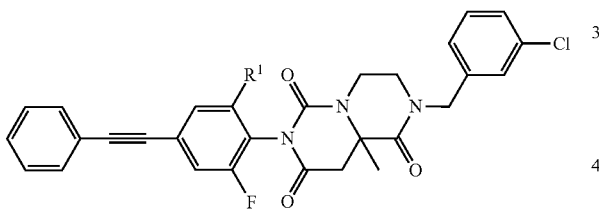

The title compound was obtained as a white solid, MS: m/e=534.3, 536.3 (M+H+), using chemistry similar to that described in Example 83, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 1-(bromomethyl)-3-chlorobenzene.

Example 89

(9aS)-7-[2,6-difluoro-4-(2-phenylethynyl)phenyl]-2-[(2-fluorophenyl)methyl]-9a-methyl-4,9-dihydro-3H-pyrazino[1,2-c]pyrimidine-1,6,8-trione

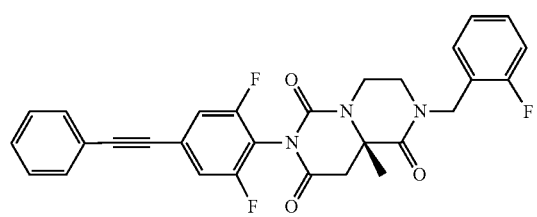 [SMILES: C[C@@]12CC(=O)N(c3c(F)cc(C#Cc4ccccc4)cc3F)C(=O)N1CCN(Cc1ccccc1F)C2=O]

The title compound was obtained as a white crystalline solid, MS: m/e=518.3 (M+H+), using chemistry similar to that described in Example 83, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 1-(bromomethyl)-2-fluorobenzene.

Example 90

(9aS)-7-[2,6-difluoro-4-(2-phenylethynyl)phenyl]-2-[(3-fluorophenyl)methyl]-9a-methyl-4,9-dihydro-3H-pyrazino[1,2-c]pyrimidine-1,6,8-trione

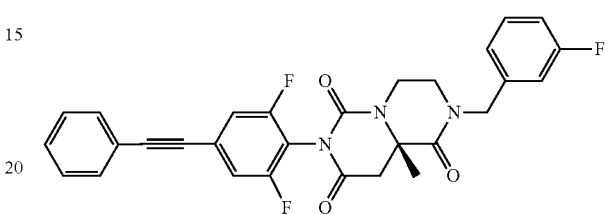

The title compound was obtained as a white solid, MS: m/e=518.3 (M+H+), using chemistry similar to that described in Example 83, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 1-(bromomethyl)-3-fluorobenzene.

Example 91

(9aS)-7-[2,6-difluoro-4-(2-phenylethynyl)phenyl]-2-[(4-fluorophenyl)methyl]-9a-methyl-4,9-dihydro-3H-pyrazino[1,2-c]pyrimidine-1,6,8-trione

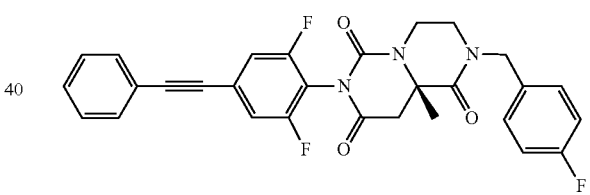

The title compound was obtained as a white solid, MS: m/e=518.3 (M+H+), using chemistry similar to that described in Example 83, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 1-(bromomethyl)-3-fluorobenzene.

Example 92

(9aRS)-7-[2,6-difluoro-4-(2-phenylethynyl)phenyl]-9a-methyl-2-(2-pyridylmethyl)-4,9-dihydro-3H-pyrazino[1,2-c]pyrimidine-1,6,8-trione

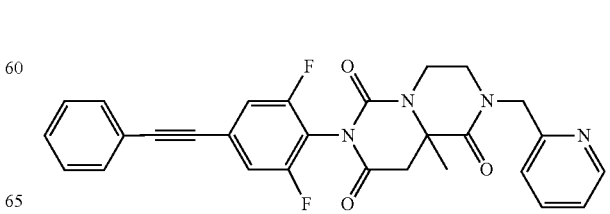

The title compound was obtained as a light yellow crystalline solid, MS: m/e=501.3 (M+H+), using chemistry similar to that described in Example 83, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 2-(bromomethyl)pyridine hydrobromide.

Example 93

(9aRS)-7-[2,6-difluoro-4-(2-phenylethynyl)phenyl]-9a-methyl-2-(3-pyridylmethyl)-4,9-dihydro-3H-pyrazino[1,2-c]pyrimidine-1,6,8-trione

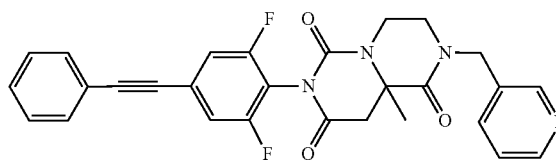

The title compound was obtained as a white solid, MS: m/e=501.3 (M+H+), using chemistry similar to that described in Example 83, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 3-(bromomethyl)pyridine hydrobromide.

Example 94

(9aRS)-7-[2,6-difluoro-4-(2-phenylethynyl)phenyl]-9a-methyl-2-(4-pyridylmethyl)-4,9-dihydro-3H-pyrazino[1,2-c]pyrimidine-1,6,8-trione

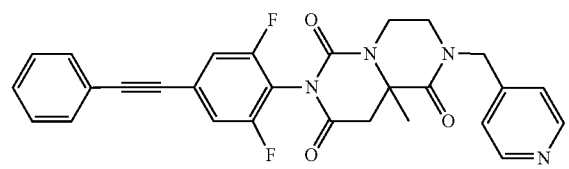 [SMILES: CC12CC(=O)N(c3c(F)cc(C#Cc4ccccc4)cc3F)C(=O)N1CCN(Cc1ccncc1)C2=O]

The title compound was obtained as a light yellow solid, MS: m/e=501.3 (M+H+), using chemistry similar to that described in Example 83, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 4-(bromomethyl)pyridine hydrobromide.

Example 95

(9aRS)-7-[2,6-difluoro-4-(2-phenylethynyl)phenyl]-9a-methyl-2-(pyrimidin-4-ylmethyl)-4,9-dihydro-3H-pyrazino[1,2-c]pyrimidine-1,6,8-trione

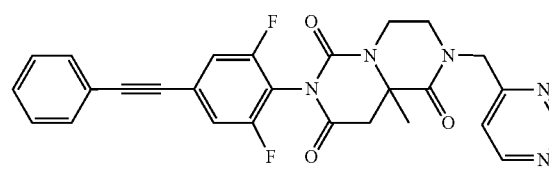

The title compound was obtained as a light yellow solid, MS: m/e=502.3 (M+H+), using chemistry similar to that described in Example 83, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 4-(bromomethyl)pyrimidine hydrobromide.

Example 96

(9aRS)-7-[2,6-difluoro-4-(2-phenylethynyl)phenyl]-9a-methyl-2-[(1-methylpyrazol-4-yl)methyl]-4,9-dihydro-3H-pyrazino[1,2-c]pyrimidine-1,6,8-trione

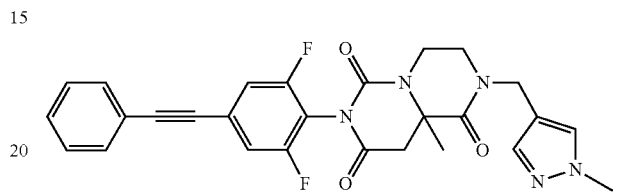

The title compound was obtained as a light brown solid, MS: m/e=504.3 (M+H+), using chemistry similar to that described in Example 79, from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 4, step 1) and 4-(bromomethyl)-1-methyl-1H-pyrazole hydrobromide.

Example 97

(9aS)-7-[2,6-difluoro-4-(2-phenylethynyl)phenyl]-9a-methyl-2-[(2-methylpyrazol-3-yl)methyl]-4,9-dihydro-3H-pyrazino[1,2-c]pyrimidine-1,6,8-trione

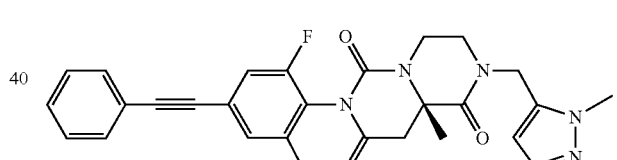

The title compound was obtained as a light yellow solid, MS: m/e=504.3 (M+H+), using chemistry similar to that described in Example 79, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 5-(bromomethyl)-1-methyl-1H-pyrazole.

Example 98

(9aS)-7-[2,6-difluoro-4-(2-phenylethynyl)phenyl]-2-(2-imidazol-1-ylethyl)-9a-methyl-4,9-dihydro-3H-pyrazino[1,2-c]pyrimidine-1,6,8-trione

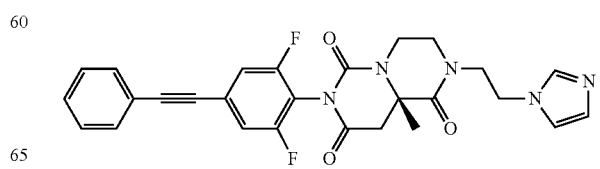

The title compound was obtained as a white solid, MS: m/e=504.2 (M+H+), using chemistry similar to that described in Example 79, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 5-(bromomethyl)-1-methyl-1H-pyrazole.

Example 99

(9aS)-7-[2,6-difluoro-4-(2-phenylethynyl)phenyl]-9a-methyl-2-[2-(2-methylimidazol-1-yl)ethyl]-4,9-dihydro-3H-pyrazino[1,2-c]pyrimidine-1,6,8-trione

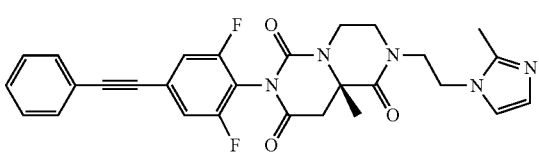 [SMILES: Cc1nccn1CCN1CCN2C(=O)N(c3c(F)cc(C#Cc4ccccc4)cc3F)C(=O)C[C@@]2(C)C1=O]

The title compound was obtained as a white solid, MS: m/e=518.2 (M+H+), using chemistry similar to that described in Example 79, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 1-(2-bromoethyl)-2-methyl-1H-imidazole hydrobromide.

Example 100

(9aS)-7-[2,6-difluoro-4-(2-phenylethynyl)phenyl]-9a-methyl-2-[2-(2-methylpyrazol-3-yl)ethyl]-4,9-dihydro-3H-pyrazino[1,2-c]pyrimidine-1,6,8-trione

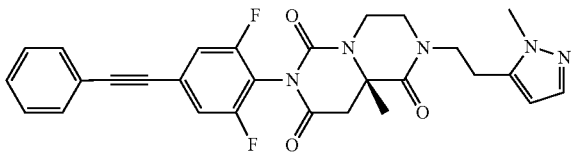 [SMILES: Cn1nccc1CCN1CCN2C(=O)N(c3c(F)cc(C#Cc4ccccc4)cc3F)C(=O)C[C@@]2(C)C1=O]

The title compound was obtained as a light yellow solid, MS: m/e=518.3 (M+H+), using chemistry similar to that described in Example 79, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 5-(2-bromoethyl)-1-methyl-1H-pyrazole.

Example 101

(9aS)-7-[2,6-difluoro-4-(2-phenylethynyl)phenyl]-9a-methyl-2-[2-(1-methylpyrazol-4-yl)ethyl]-4,9-dihydro-3H-pyrazino[1,2-c]pyrimidine-1,6,8-trione

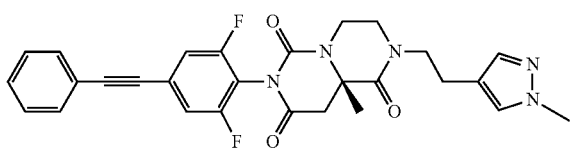 [SMILES: Cn1cc(CCN2CCN3C(=O)N(c4c(F)cc(C#Cc5ccccc5)cc4F)C(=O)C[C@@]3(C)C2=O)cn1]

The title compound was obtained as a white solid, MS: m/e=518.2 (M+H+), using chemistry similar to that described in Example 79, from (9aS)-7-[2,6-difluoro-4-(2-phenylethynyl)phenyl]-9a-methyl-2,3,4,9-tetrahydropyrazino[1,2-c]pyrimidine-1,6,8-trione (Example 4, step 2) and 4-(2-bromoethyl)-1-methyl-1H-pyrazole.

Example 102

(9aRS)-7-[2,6-difluoro-4-(2-phenylethynyl)phenyl]-9a-(methoxymethyl)-2-(3-pyridyl)-4,9-dihydro-3H-pyrazino[1,2-c]pyrimidine-1,6,8-trione

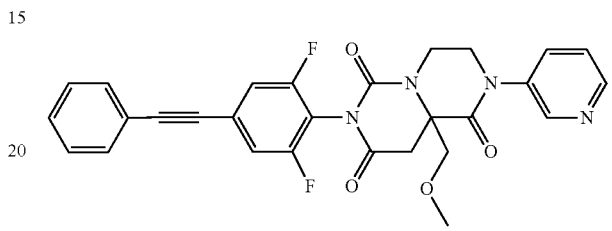

Step 1: 1-[(E)-cinnamyl]oxy-3-methoxy-propan-2-ol

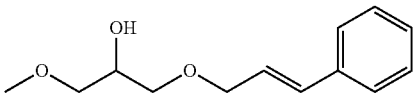 [SMILES: COCC(O)COC/C=C/c1ccccc1]

NaH (60% in oil) (5.44 g, 136.2 mmol) was added to stirred solution of trans-cinnamyl alcohol (18.27 g, 136.2 mmol) in THF (150 ml) at 0° C. and reaction mixture was stirred at 25° C. for 30 min. Then glycidyl methyl ether (10 g, 113.5 mmol) was added to the reaction mixture and reaction mixture was stirred at 70° C. for 16 h. The reaction mixture was quenched with water and extracted with ethyl acetate (2×250 ml). The combined organic layer was washed with brine, dried over $Na_2SO_4$ and concentrated. The resulting crude material was purified by column chromatography over silica gel (10-12% EtOAc/hexane). The title compound (8.4 g, 25%) was obtained as a yellow liquid.

Step 2: 1-[(E)-cinnamyl]oxy-3-methoxy-propan-2-one

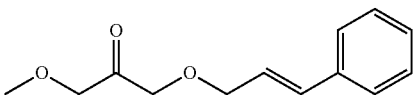 [SMILES: COCC(=O)COC/C=C/c1ccccc1]

Dess-Martin periodinane (6.93 g, 16.4 mmol) was added to a stirred solution of 1-[(E)-cinnamyl]oxy-3-methoxy-propan-2-ol (example 102, step 1) (2.42 g, 10.9 mmol) in dichloromethane (60 ml) at 25° C. and the reaction mixture was stirred at 25° C. for 3 h, quenched with water and extracted with dichloromethane (2×60 ml). The combined organic layer was washed with saturated aqueous $NaHCO_3$ solution and brine, dried over $Na_2SO_4$ and concentrated. The resulting crude material was purified by column chromatog- Step 3: Ethyl (Z)-3-[[(E)-cinnamyl]oxymethyl]-4-methoxy-but-2-enoate

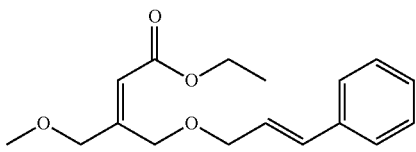 [SMILES: CCOC(=O)/C=C(/COC)COC/C=C/c1ccccc1]

To a solution of 1-[(E)-cinnamyl]oxy-3-methoxy-propan-2-one (example 102, step 2) (3.00 g, 13.6 mmol) in dichloromethane (150 ml) was added (carbethoxymethylene)triphenyl-phosphorane (9.50 g, 27.3 mmol) and the reaction mixture was stirred at 25° C. for 24 h. The solvent was evaporated and the resulting crude material was purified by column chromatography (10-15% EtOAc/hexane). The title compound (3.26 g, 82%) was obtained as a light yellow oil, MS: m/e=291.3 (M+H+).

Step 4: Ethyl (3RS)-3-amino-3-[[(E)-cinnamyl]oxymethyl]-4-methoxy-butanoate

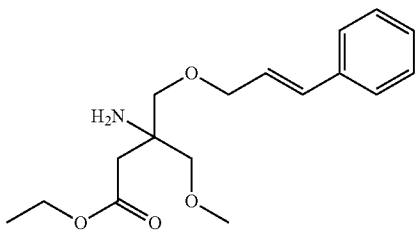 [SMILES: CCOC(=O)CC(N)(COC)COC/C=C/c1ccccc1]

Ethyl (Z)-3-[[(E)-cinnamyl]oxymethyl]-4-methoxy-but-2-enoate (example 102, step 3) (3.62 g, 12.5 mmol) was dissolved in a saturated solution of NH$_3$ in ethanol (4 ml) in a sealed tube which was heated at 90° C. for 24 h. The solvent was evaporated and the resulting crude material was purified by column chromatography (EtOAc). The title compound (1.9 g, 85% based on recovered starting material) was obtained as a yellow oil, MS: m/e=307.9 (M+H+).

Step 5: Ethyl (3RS)-3-[[(E)-cinnamyl]oxymethyl]-3-[[2,6-difluoro-4-(2-phenylethynyl)phenyl]-carbamoylamino]-4-methoxy-butanoate

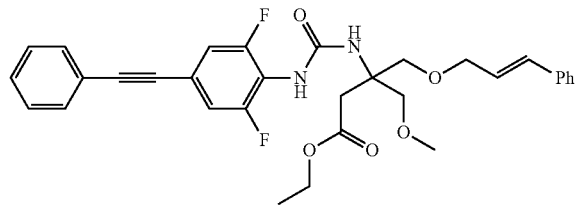 [SMILES: CCOC(=O)CC(COC)(COC/C=C/c1ccccc1)NC(=O)Nc1c(F)cc(C#Cc2ccccc2)cc1F]

Triphosgene (1.29 g, 4.37 mmol) was added to stirred solution of 2,6-difluoro-4-phenylethynyl-phenyl amine (example 1, step 1) (1.00 g, 4.37 mmol) in toluene (100 ml) at 25° C. and the reaction mixture was stirred at 90° C. for 4 h. The solvent was evaporated, and the resulting isocyanate was diluted with dichloromethane (50 ml) and added to a stirred solution of ethyl (3RS)-3-amino-3-[[(E)-cinnamyl]oxymethyl]-4-methoxy-butanoate (example 102, step 4) (1.34 g, 4.37 mmol) and Et$_3$N (1.82 ml, 13.1 mmol) in dichloromethane (30 ml) at 0° C. Then the reaction mixture was stirred for at r.t. for 16 h. The reaction mixture was diluted with dichloromethane and washed with water. The organic layer was dried over Na$_2$SO$_4$ and concentrated. The resulting crude material was purified by column chromatography over silica gel (30-40% EtOAc/hexane) to yield the title compound (1.38 g, 56%) as an off white solid, MS: m/e=563.2 (M+H+).

Step 6: (6RS)-6-[[(E)-cinnamyl]oxymethyl]-3-[2,6-difluoro-4-(2-phenylethynyl)phenyl]-6-(methoxymethyl)hexahydropyrimidine-2,4-dione

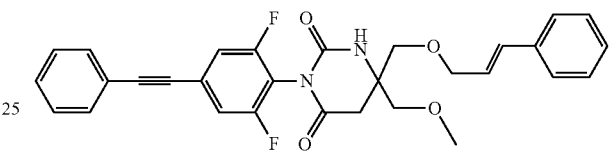

A solution of ethyl (3RS)-3-[[(E)-cinnamyl]oxymethyl]-3-[[2,6-difluoro-4-(2-phenylethynyl)-phenyl]-carbamoylamino]-4-methoxy-butanoate (example 102, step 5) (3.00 g, 5.34 mmol) in THF (30 ml) was added to a well stirred solution of NaH (60% in oil) (320 mg, 8.01 mmol) in THF (40 ml) at 0° C. and reaction mixture was stirred at 25° C. for 2 h. Reaction mixture was quenched with water and extracted with EtOAc (2×120 ml). The combined organic layer was dried over Na$_2$SO$_4$ and evaporated. The resulting crude material was purified by column chromatography over silica gel (20-30% EA/hexane) to obtain the title compound (2.50 g, 91%) as an off white solid, MS: m/e=517.0 (M+H+).

Step 7: tert-butyl N-[2-[(6RS)-6-[[(E)-cinnamyl]oxymethyl]-3-[2,6-difluoro-4-(2-phenylethynyl)phenyl]-6-(methoxymethyl)-2,4-dioxo-hexahydropyrimidin-1-yl]ethyl]carbamate

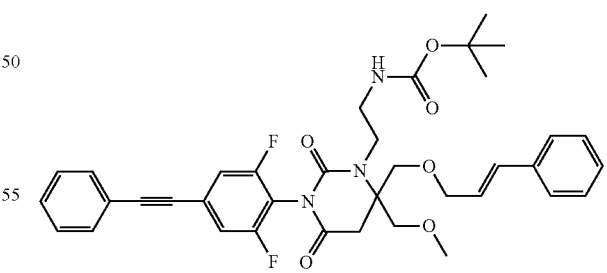

To a solution of (6RS)-6-[[(E)-cinnamyl]oxymethyl]-3-[2,6-difluoro-4-(2-phenylethynyl)-phenyl]-6-(methoxymethyl)hexahydropyrimidine-2,4-dione (example 102, step 6) (1.00 g, 1.94 mmol) in DMF (6.7 ml) were added tert-butyl (2-bromoethyl)carbamate (0.868 g, 3.87 mmol) and cesium carbonate (1.39 g, 4.26 mmol). The reaction mixture was stirred for 16 h at 55° C. The solvent was evaporated in vaccuo, and the residue was taken up in 60 ml EtOAc/

Heptane 3:1. The unsoluble material was filtered off and the filtrate was washed with water, brine, dried over Na₂SO₄ and concentrated. The resulting crude material was purified by flash chromatography over silica gel using a 0-40% EtOAc in hexane gradient to obtain the title compound (1.18 g, 92%) as a white foam, MS: m/e=560.2 ((M-Boc)+H+).

Step 8: tert-butyl N-[2-[(6RS)-3-[2,6-difluoro-4-(2-phenylethynyl)phenyl]-6-(hydroxymethyl)-6-(methoxymethyl)-2,4-dioxo-hexahydropyrimidin-1-yl]ethyl]carbamate

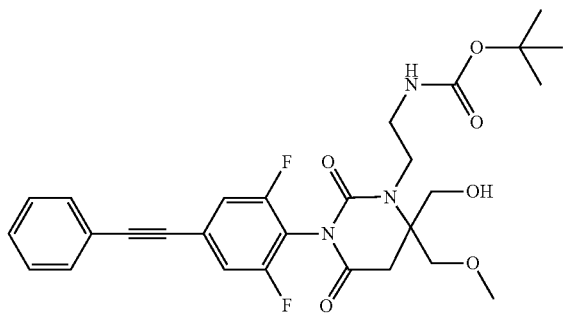 [SMILES: COCC1(CO)CC(=O)N(c2c(F)cc(C#Cc3ccccc3)cc2F)C(=O)N1CCNC(=O)OC(C)(C)C]

To a solution of tert-butyl N-[2-[(6RS)-6-[[(E)-cinnamyl]oxymethyl]-3-[2,6-difluoro-4-(2-phenylethynyl)phenyl]-6-(methoxymethyl)-2,4-dioxo-hexahydropyrimidin-1-yl]ethyl]carbamate (example 102, step 7) (1.150 g, 1.74 mmol) in nitromethane (30 ml) were added cerium (III) chloride heptahydrate (0.714 g, 1.92 mmol), sodium iodide (0.287 g, 1.92 mmol), and 1,3-propanediol (0.208 g, 194 ul, 1.92 mmol). The mixture was stirred 32 h at 100° C. The reaction mixture was concentrated in vaccuo and taken up in 60 ml of dichloromethane/MeOH 93:7. The solids were filtered off and the filtrate was washed with water. The organic phase was concentrated and the residue was purified by flash chromatography over a Silica-Aminophase column using a 1:1 EtOAc/Heptane, then EtOAc and finally EtOAc/MeOH 95:5 as eluant to yield 490 mg of a light yellow solid containing debocylated material and a difficult to separate impurity. This material was dissolved in THF (22 ml), triethylamine (0.168 g, 231 ul, 1.66 mmol) and di-tert-Butyl dicarbonate (0.289 g, 1.33 mmol) were added and the mixture was stirred for 2 h at 25° C. The mixture was concentrated and the residue was purified by flash chromatography over silicagel using a 0-100% EtOAc in Heptane gradient to yield the title compound (0.362 g, 38%) as a white solid, MS: m/e=444.2 ((M-Boc)+H+).

Step 9: tert-butyl (9aRS)-7-[2,6-difluoro-4-(2-phenylethynyl)phenyl]-9a-(methoxymethyl)-1,6,8-trioxo-4,9-dihydro-3H-pyrazino[1,2-c]pyrimidine-2-carboxylate

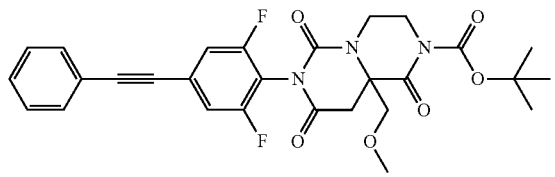 [SMILES: COCC12CC(=O)N(c3c(F)cc(C#Cc4ccccc4)cc3F)C(=O)N1CCN(C(=O)OC(C)(C)C)C2=O]

To a solution of tert-butyl N-[2-[(6RS)-3-[2,6-difluoro-4-(2-phenylethynyl)phenyl]-6-(hydroxymethyl)-6-(methoxymethyl)-2,4-dioxo-hexahydropyrimidin-1-yl]ethyl]carbamate (example 102, step 8) (0.260 g, 0.478 mmol) in dichloromethane (11 ml) and DMF (1.6 ml) were added 0.900 g of powdered activated 4 A molecular sieves, pyridinium dichromate (0.675 g, 1.79 mmol, 3.75 eq.) and acetic acid (0.124 g, 118 ul, 2.06 mmol). The mixture was stirred for 16 h at r.t. The reaction was diluted with 50 ml EtOAc, then Speedex (ca. 5 g) was added and the suspension was stirred for 5 min. The solids were filtered off and washed with 50 ml EtOAc. The filtrate was dried over Na₂SO₄ and evaporated. The resulting crude material was purified by column chromatography over silica gel using a 0-80% EtOAc in heptane gradient to obtain the title compound (0.114 g, 54%) as a white solid, MS: m/e=440.2 ((M-Boc)+H+).

Step 10: (9aRS)-7-[2,6-difluoro-4-(2-phenylethynyl)phenyl]-9a-(methoxymethyl)-2,3,4,9-tetrahydropyrazino[1,2-c]pyrimidine-1,6,8-trione

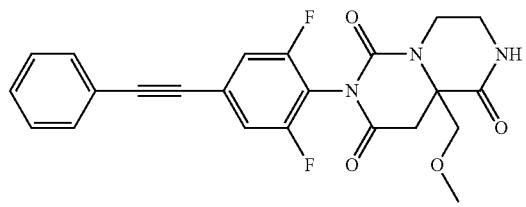 [SMILES: COCC12CC(=O)N(c3c(F)cc(C#Cc4ccccc4)cc3F)C(=O)N1CCNC2=O]

A solution of tert-butyl (9aRS)-7-[2,6-difluoro-4-(2-phenylethynyl)phenyl]-9a-(methoxymethyl)-1,6,8-trioxo-4,9-dihydro-3H-pyrazino[1,2-c]pyrimidine-2-carboxylate (example 102, step 9) (0.140 g, 0.259 mmol) in 7 ml of dichloromethane was cooled to 0-2° C. Then a 4N solution (0.519 ml, 2.08 mmol, 8 eq.) of HCl/dioxane were added. After stirring for 2 h at r.t., the solution was diluted with 20 ml of dichloromethane, quenched by addition of 5 ml 5% NaHCO₃ solution followed by extraction with dichloromethane. The organic layer was washed with brine, dried over Na₂SO₄ and concentrated to yield the title compound (0.109 g, 96%) as a crystalline white solid, MS: m/e=440.2 (M+H+).

Step 11: (9aRS)-7-[2,6-difluoro-4-(2-phenylethynyl)phenyl]-9a-(methoxymethyl)-2-(3-pyridyl)-4,9-dihydro-3H-pyrazino[1,2-c]pyrimidine-1,6,8-trione The title compound was obtained as a white solid, MS: m/e=517.2 (M+H⁺), using chemistry similar to that described in example 5, from (9aRS)-7-[2,6-difluoro-4-(2-phenylethynyl)phenyl]-9a-(methoxymethyl)-2,3,4,9-tetrahydropyrazino[1,2-c]pyrimidine-1,6,8-trione (Example 102, step 10) and 3-iodopyridine.

Example 103

(9aR)-7-[2,6-difluoro-4-(2-phenylethynyl)phenyl]-9a-(methoxymethyl)-2-(3-pyridyl)-4,9-dihydro-3H-pyrazino[1,2-c]pyrimidine-1,6,8-trione

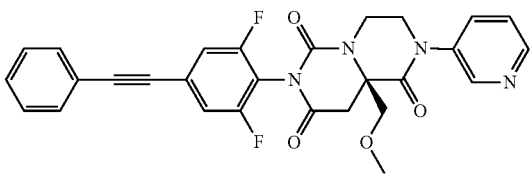 [SMILES: COC[C@@]12CC(=O)N(c3c(F)cc(C#Cc4ccccc4)cc3F)C(=O)N1CCN(c1cccnc1)C2=O]

Chiral separation of the racemate of example 102 was realized by chiral HPLC on a Reprosil Chiral-NR column using (hexane/EtOH/NH$_4$OAc—70/30/0.1%) as eluent which yielded (9aR)-7-[2,6-difluoro-4-(2-phenylethynyl)phenyl]-9a-(methoxymethyl)-2-(3-pyridyl)-4,9-dihydro-3H-pyrazino[1,2-c]pyrimidine-1,6,8-trione as a white solid (MS: 517.3 (M+H$^+$)); and (9aS)-7-[2,6-difluoro-4-(2-phenylethynyl)phenyl]-9a-(methoxymethyl)-2-(3-pyridyl)-4,9-dihydro-3H-pyrazino[1,2-c]pyrimidine-1,6,8-trione as a white solid (MS: 517.3 (M+H$^+$)).

Example 104

(9aRS)-7-[2,6-difluoro-4-(2-phenylethynyl)phenyl]-9a-(methoxymethyl)-2-(1-methylpyrazol-4-yl)-4,9-dihydro-3H-pyrazino[1,2-c]pyrimidine-1,6,8-trione

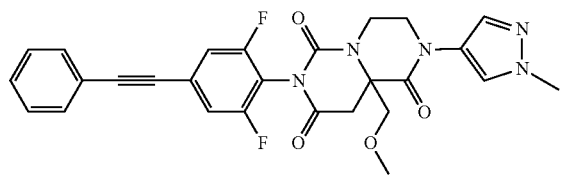 [SMILES: COCC12CC(=O)N(c3c(F)cc(C#Cc4ccccc4)cc3F)C(=O)N1CCN(c1cnn(C)c1)C2=O]

The title compound was obtained as a white solid, MS: m/e=520.2 (M+H$^+$), using chemistry similar to that described in example 5, from (9aRS)-7-[2,6-difluoro-4-(2-phenylethynyl)phenyl]-9a-(methoxymethyl)-2,3,4,9-tetrahydropyrazino[1,2-c]pyrimidine-1,6,8-trione (Example 102, step 10) and 4-iodo-1-methyl-1H-pyrazole.

Example 105

(9aR)-7-[2,6-difluoro-4-(2-phenylethynyl)phenyl]-9a-(methoxymethyl)-2-(1-methylpyrazol-4-yl)-4,9-dihydro-3H-pyrazino[1,2-c]pyrimidine-1,6,8-trione

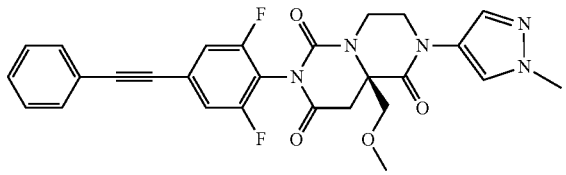 [SMILES: COC[C@@]12CC(=O)N(c3c(F)cc(C#Cc4ccccc4)cc3F)C(=O)N1CCN(c1cnn(C)c1)C2=O]

The title compound was obtained as an off-white solid, MS: m/e=520.2 (M+H$^+$), by chiral HPLC separation of racemic (9aRS)-7-[2,6-difluoro-4-(2-phenylethynyl)phenyl]-9a-(methoxymethyl)-2-(1-methylpyrazol-4-yl)-4,9-dihydro-3H-pyrazino[1,2-c]pyrimidine-1,6,8-trione (Example 104) on a Chiralpak AD column using (heptane/EtOH/NH$_4$OAc—60/40/0.1%) as eluent.

Example 106

(9aS)-7-[2,6-difluoro-4-(2-phenylethynyl)phenyl]-9a-ethyl-2-(3-pyridyl)-4,9-dihydro-3H-pyrazino[1,2-c]pyrimidine-1,6,8-trione

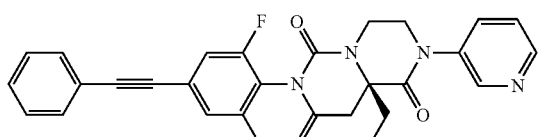

Step 1: 1-allyloxybutan-2-ol

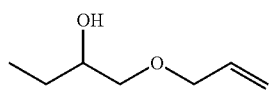

A solution of 1,2-epoxybutane (19.33 g, 332.82 mmol) in THF (100 ml) was added to a suspension of NaH (13.31 g, 332.82 mmol) in THF (130 ml) at 0° C. and reaction mixture was stirred at 25° C. for 30 min. Then a solution of allyl alcohol (20.0 g, 277.35 mmol) in THF (70 ml) was added at 25° C. and the reaction mixture was refluxed for 16 h. After quenching with water and extraction with EtOAc (2×500 ml), the combined organic layer was dried over Na$_2$SO$_4$ and concentrated. The resulting crude material was purified by column chromatography over silica gel (15-20% EtOAc/hexane). The title compound (13 g, 36%) was obtained as as yellow liquid.

Step 2: 1-allyloxybutan-2-one

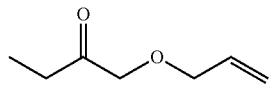

To a solution of 1-allyloxy-butan-2-ol (example 106, step 1) (5.0 g, 38.5 mmol) in dichloromethane (100 ml) at 25° C. was added pyridinium dichromate (20.72 g, 96.15 mmol) and the reaction mixture was stirred at 25° C. for 5 h, filtered through the celite and the filtrate was concentrated. The title compound (4.3 g, 87%) was obtained as a brown oil which was sufficiently pure to be used directly in the next step.

Step 3: ethyl (EZ)-3-(allyloxymethyl)pent-2-enoate

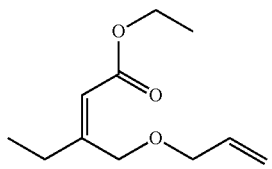

To a suspension of NaH (405 mg, 10.1 mmol) in THF (20 ml) at 0° C. was added triethyl phosphonoacetate (2.62 g, 11.7 mmol) and reaction mixture was stirred at 25° C. for 30 min. Then a solution of 1-allyloxy-butan-2-one (example 106, step 2) (1 g, 7.80 mmol) in THF (5 ml) was added and reaction mixture was stirred at 25° C. for 3 h. The reaction mixture was quenched with saturated aqueous NH₄Cl solution and extracted with EtOAc (2×40 ml). The combined organic layer was dried over Na₂SO₄, concentrated, and the resulting crude material was purified by column chromatography over silica gel (10-15% EtOAc/hexane). The title compound (1.0 g, 65%) was obtained as a yellow liquid.

Step 4: Ethyl (3RS)-3-(allyloxymethyl)-3-amino-pentanoate

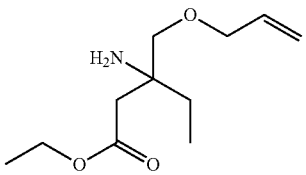

Ethyl (EZ)-3-(allyloxymethyl)pent-2-enoate (example 102, step 3) (2.8 g, 14.12 mmol) was dissolved in a saturated solution of NH₃ in ethanol (5 ml) in a sealed tube was heated at 90° C. for 16 h. The solvent was evaporated and the resulting crude material was purified by column chromatography over silica gel (80-100% EtOAc/hexane. The title compound (1.5 g, 49% based on recovered starting material (1.0 g)) was obtained as light yellow liquid.

Step 5: Ethyl (3RS)-3-(allyloxymethyl)-3-[[2,6-difluoro-4-(2-phenylethynyl)phenyl]-carbamoylamino]pentanoate

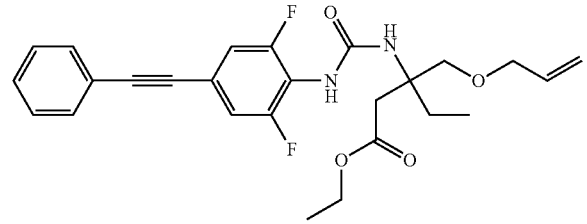 [SMILES: C=CCOCC(CC)(CC(=O)OCC)NC(=O)Nc1c(F)cc(C#Cc2ccccc2)cc1F]

Triphosgene (2.76 g, 9.3 mmol) was added to stirred solution of 2,6-difluoro-4-phenylethynyl-phenyl amine (example 1, step 1) (2.13 g, 9.3 mmol) in toluene (100 ml) at 25° C. and the reaction mixture stirred at 90° C. for 4 h. The solvent was evaporated, and the resulting isocyanate was diluted with dichloromethane (50 ml) and added to a stirred solution of ethyl (3RS)-3-(allyloxymethyl)-3-aminopentanoate (example 106, step 4) (2.0 g, 9.3 mmol) and Et₃N (3.91 ml, 27.9 mmol) in dichloromethane (50 ml) at 0° C. Then the reaction mixture was stirred for at 25° C. for 16 h. The reaction mixture was diluted with dichloromethane and washed with water. The organic layer was dried over Na₂SO₄ and concentrated. The resulting crude material was purified by column chromatography over silica gel (15% EtOAc/hexane) to yield the title compound (2.0 g, 46%) as an off white solid, MS: m/e=471.1 (M+H+).

Step 6: (6RS)-6-(allyloxymethyl)-3-[2,6-difluoro-4-(2-phenylethynyl)phenyl]-6-ethyl-hexahydropyrimidine-2,4-dione

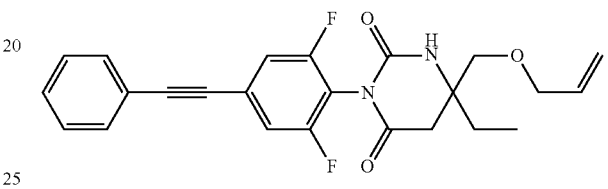

A solution of ethyl (3RS)-3-(allyloxymethyl)-3-[[2,6-difluoro-4-(2-phenylethynyl)phenyl]-carbamoylamino]pentanoate (example 106, step 5) (3.1 g, 5.51 mmol) in THF (20 ml) was added to a well stirred suspension of NaH (60% in oil) (0.220 g, 5.51 mmol) in THF (20 ml) at 0° C. and the reaction mixture was stirred at 25° C. for 2 h. The reaction mixture was quenched with water and extracted with EtOAc (2×200 ml). The combined organic layer was dried over Na₂SO₄ and evaporated. The resulting crude material was purified by column chromatography over silica gel (20% EtOAc/hexane) to obtain the title compound (2.0 g, 85%) as an off white solid, MS: m/e=425.4 (M+H+).

Step 7: tert-butyl N-[2-[(6RS)-6-(allyloxymethyl)-3-[2,6-difluoro-4-(2-phenylethynyl)phenyl]-6-ethyl-2,4-dioxo-hexahydropyrimidin-1-yl]ethyl]carbamate

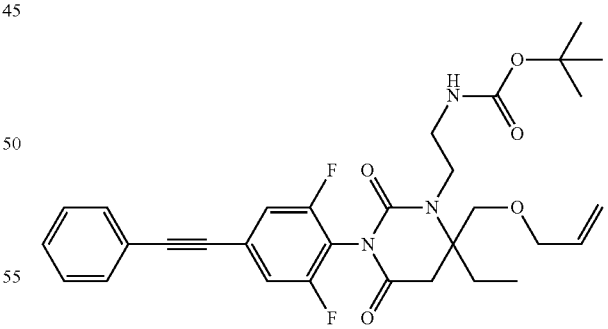

To a solution of ethyl (3RS)-3-(allyloxymethyl)-3-[[2,6-difluoro-4-(2-phenylethynyl)phenyl]-carbamoylamino]pentanoate (example 106, step 6) (1.00 g, 2.36 mmol) in DMF (8.0 ml) were added tert-butyl (2-bromoethyl)carbamate (1.06 g, 4.71 mmol) and cesium carbonate (1.69 g, 5.18 mmol). The reaction mixture was stirred for 16 h at 55° C. and 6 h at 70° C. The solvent was evaporated in vaccuo, and the residue was taken up in 60 ml EtOAc/Heptane 3:1. The unsoluble material was filtered off and the filtrate was washed with water, brine, dried over Na₂SO₄ and concentrated. The resulting crude material was purified by flash chromatography over silica gel using a 0-40% EtOAc in hexane gradient to obtain the title compound (1.34 g, 92%) as a light yellow foam, MS: m/e=468.3 ((M-Boc)+H+).

Step 8: tert-butyl N-[2-[(6RS)-3-[2,6-difluoro-4-(2-phenylethynyl)phenyl]-6-ethyl-6-(hydroxymethyl)-2,4-dioxo-hexahydropyrimidin-1-yl]ethyl]carbamate

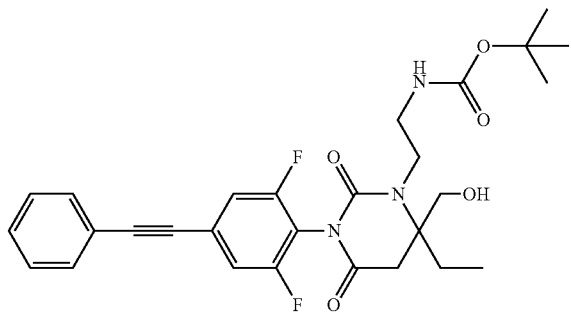 [SMILES: CCC1(CO)CC(=O)N(c2c(F)cc(C#Cc3ccccc3)cc2F)C(=O)N1CCNC(=O)OC(C)(C)C]

In a 25 ml glass pressure vessel, a solution of tert-butyl N-[2-[(6RS)-6-(allyloxymethyl)-3-[2,6-difluoro-4-(2-phenylethynyl)phenyl]-6-ethyl-2,4-dioxo-hexahydropyrimidin-1-yl]ethyl]carbamate (example 106, step 7) (0.525 g, 0.925 mmol) and 1,3-dimethylbarbituric acid (0.289 g, 1.85 mmol) in methanol (10 ml) was degassed with an argon stream and Pd(TPP)₄ catalyst (53.4 mg, 46.2 umol, 5 mol %) was added. The vessel was closed and the mixture was stirred for 3 h at 80° C. and then another 16 h at r.t. The mixture was concentrated and the residue was purified by flash chromatography over silicagel using a 0-100% EtOAc in heptane gradient to yield the title compound (0.34 g, 70%) as an amorphous colorless resin, MS: m/e=428.3 ((M-Boc)+H+).

Step 9: tert-butyl (9aRS)-7-[2,6-difluoro-4-(2-phenylethynyl)phenyl]-9a-ethyl-1,6,8-trioxo-4,9-dihydro-3H-pyrazino[1,2-c]pyrimidine-2-carboxylate

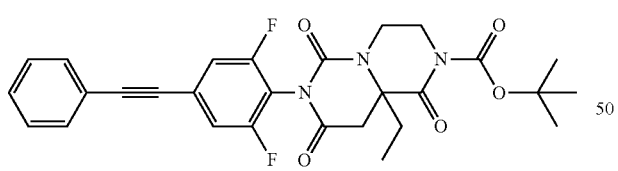

To a solution of tert-butyl N-[2-[(6RS)-6-(allyloxymethyl)-3-[2,6-difluoro-4-(2-phenylethynyl)phenyl]-6-ethyl-2,4-dioxo-hexahydropyrimidin-1-yl]ethyl]carbamate (example 106, step 8) (0.620 g, 1.18 mmol) in dichloromethane (33 ml) and DMF (3.5 ml) were added 1.5 g of powdered activated 4 A molecular sieves, pyridinium dichromate (1.55 g, 4.11 mmol) and acetic acid (0.282 g, 269 ul, 4.7 mmol). The mixture was stirred for 16 h at r.t. The reaction was diluted with 60 ml EtOAc, then Speedex (ca. 5 g) was added and the suspension was stirred for 5 min. The solids were filtered off and washed with 60 ml EtOAc. The filtrate was dried over Na₂SO₄ and evaporated. The resulting crude material was purified by column chromatography over silica gel using a 0-80% EtOAc in heptane gradient to obtain the title compound (0.274 g, 45%) as a white solid, MS: m/e=424.2 ((M-Boc)+H+).

Step 10: (9aRS)-7-[2,6-difluoro-4-(2-phenylethynyl)phenyl]-9a-ethyl-2,3,4,9-tetrahydropyrazino[1,2-c]pyrimidine-1,6,8-trione

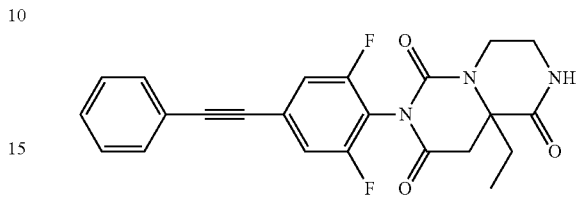

A solution of tert-butyl (9aRS)-7-[2,6-difluoro-4-(2-phenylethynyl)phenyl]-9a-ethyl-1,6,8-trioxo-4,9-dihydro-3H-pyrazino[1,2-c]pyrimidine-2-carboxylate (example 106, step 9) (0.280 g, 0.535 mmol) in 12 ml of dichloromethane was cooled to 0-2° C. Then a 4N solution (1.07 ml, 4.28 mmol, 8 equiv.) of HCl in dioxane was added. After stirring for 2 h at r.t., the solution was diluted with 20 ml of dichloromethane, quenched by addition of 5 ml 5% NaHCO₃ solution followed by extraction with dichloromethane. The organic layer was washed with brine, dried over Na₂SO₄ and concentrated to yield the title compound (0.221 g, 98%) as a crystalline white solid, MS: m/e=424.2 (M+H+).

Step 11: (9aS)- and (9aR)-7-[2,6-difluoro-4-(2-phenylethynyl)phenyl]-9a-ethyl-2,3,4,9-tetrahydropyrazino[1,2-c]pyrimidine-1,6,8-triones

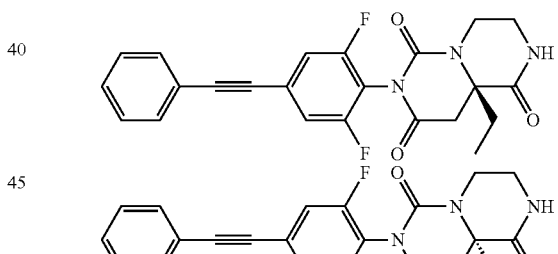

Chiral separation of the enantiomers was realized by chiral HPLC using a Chiralpak IE column using (hexane/EtOH/DCM/Et₂N—70/20/10/0.1%) as eluant to obtain (9aS)-7-[2,6-difluoro-4-(2-phenylethynyl)phenyl]-9a-ethyl-2,3,4,9-tetrahydropyrazino[1,2-c]pyrimidine-1,6,8-trione as a light yellow solid (MS: 424.2 (M+H⁺)); and (9aR)-7-[2,6-difluoro-4-(2-phenylethynyl)-phenyl]-9a-ethyl-2,3,4,9-tetrahydropyrazino[1,2-c]pyrimidine-1,6,8-trione as a light yellow solid (MS: 424.2 (M+H⁺)).

Step 12: (9aS)-7-[2,6-difluoro-4-(2-phenylethynyl)phenyl]-9a-ethyl-2-(3-pyridyl)-4,9-dihydro-3H-pyrazino[1,2-c]pyrimidine-1,6,8-trione The title compound was obtained as a white solid, MS: m/e=501.3 (M+H⁺), using chemistry similar to that described in example 5, from (9aS)-7-[2,6-difluoro-4-(2-phenylethynyl)phenyl]-9a-ethyl-2,3,4,9-tetrahydropyrazino[1,2-c]pyrimidine-1,6,8-trione (Example 106, step 11) and 3-iodopyridine.

Example 107

(9aS)-7-[2,6-difluoro-4-(2-phenylethynyl)phenyl]-9a-ethyl-2-(1-methylpyrazol-4-yl)-4,9-dihydro-3H-pyrazino[1,2-c]pyrimidine-1,6,8-trione

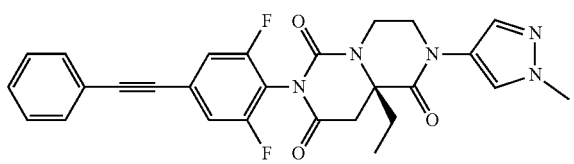 [SMILES: CC[C@@]12CC(=O)N(c3c(F)cc(C#Cc4ccccc4)cc3F)C(=O)N1CCN(c1cnn(C)c1)C2=O]

The title compound was obtained as a white solid, MS: m/e=504.3 (M+H⁺), using chemistry similar to that described in example 5, from (9aS)-7-[2,6-difluoro-4-(2-phenylethynyl)phenyl]-9a-ethyl-2,3,4,9-tetrahydropyrazino[1,2-c]pyrimidine-1,6,8-trione (Example 106, step 11) and 4-iodo-1-methyl-1H-pyrazole.

Example 108

(9aRS)-7-[2-fluoro-4-(2-phenylethynyl)phenyl]-9a-methyl-2-(3-pyridyl)-4,9-dihydro-3H-pyrazino[1,2-c]pyrimidine-1,6,8-trione

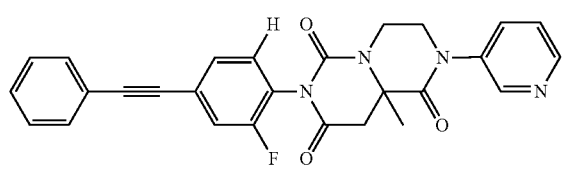 [SMILES: CC12CC(=O)N(c3ccc(C#Cc4ccccc4)cc3F)C(=O)N1CCN(c1cccnc1)C2=O]

Step 1: 2-fluoro-4-phenylethynyl-phenylamine

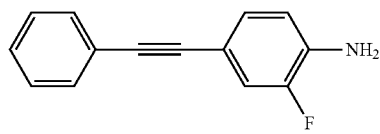 [SMILES: Nc1ccc(C#Cc2ccccc2)cc1F]

The title compound was obtained as a brown solid, MS: m/e=212.2 (M+H⁺), using chemistry similar to that described in example 1, step 1 from 2-fluoro-4-iodoaniline and phenylacetylene.

Step 2: (9aRS)-7-[2-fluoro-4-(2-phenylethynyl)phenyl]-9a-methyl-2,3,4,9-tetrahydropyrazino[1,2-c]pyrimidine-1,6,8-trione

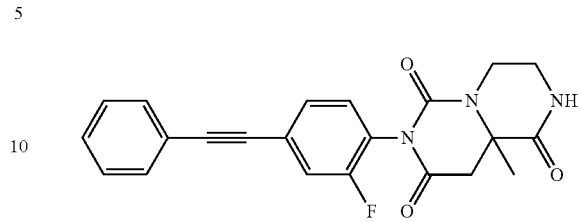

The title compound was obtained as a white solid, MS: m/e=392.2 (M+H⁺), using chemistry similar to that described in Example 1, step 2 from 2-fluoro-4-phenylethynyl-phenylamine (Example 107, step 1) and methyl 2-[(2RS)-2-methyl-3-oxo-piperazin-2-yl]acetate.

Step 3: (9aRS)-7-[2-fluoro-4-(2-phenylethynyl)phenyl]-9a-methyl-2-(3-pyridyl)-4,9-dihydro-3H-pyrazino[1,2-c]pyrimidine-1,6,8-trione The title compound was obtained as a white solid, MS: m/e=469.3 (M+H⁺), using chemistry similar to that described in example 5, from (9aRS)-7-[2-fluoro-4-(2-phenylethynyl)phenyl]-9a-methyl-2,3,4,9-tetrahydropyrazino[1,2-c]pyrimidine-1,6,8-trione (Example 107, step 2) and 3-iodopyridine.

Example 109

(9aS)-7-[2,6-difluoro-4-[2-(2-fluorophenyl)ethynyl]phenyl]-9a-methyl-2-(3-pyridyl)-4,9-dihydro-3H-pyrazino[1,2-c]pyrimidine-1,6,8-trione

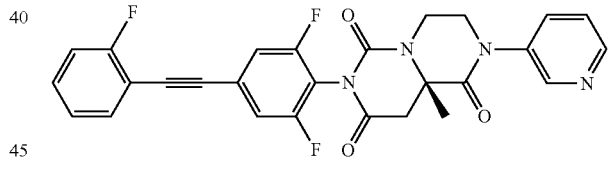

Step 1: (9aRS)-7-(2,6-difluoro-4-iodo-phenyl)-9a-methyl-2,3,4,9-tetrahydropyrazino[1,2-c]pyrimidine-1,6,8-trione

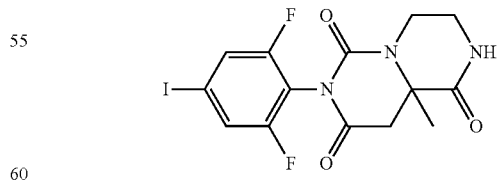

To a solution of 2,6-difluoro-4-iodo-phenyl amine (3.00 g, 11.8 mmol) in toluene (80 ml) was added CDI (5.72 g, 35.3 mmol) and reaction mixture was stirred for 1 h at 110° C. Then (2-methyl-3-oxo-piperazin-2-yl)-acetic acid methyl ester (2.63 g, 14.1 mmol) was added and reaction mixture was refluxed for 2 h. Reaction mixture was concentrated and resulting crude was purified by column chromatography over silica gel (70% EA/hexane) to obtain the title compound (4.37 g, 85%) as an off-white solid, MS: m/e=436.2 (M+H⁺).

Step 2: (9aRS)-7-[2,6-difluoro-4-[2-(2-fluorophenyl)ethynyl]phenyl]-9a-methyl-2,3,4,9-tetrahydropyrazino[1,2-c]pyrimidine-1,6,8-trione

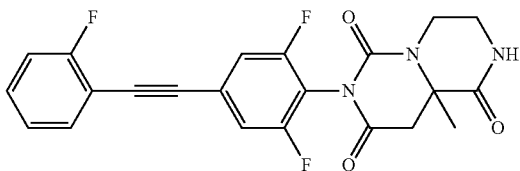 [SMILES: CC12CC(=O)N(c3c(F)cc(C#Cc4ccccc4F)cc3F)C(=O)N1CCNC2=O]

To a solution of (9aRS)-7-(2,6-difluoro-4-iodophenyl)-9a-methyltetrahydro-1H-pyrazino[1,2-c]pyrimidine-1,6,8(2H,7H)-trione (Example 109, step 1) (2.5 g, 5.74 mmol) under argon in THF (15 ml) were added 1-ethynyl-2-fluorobenzene (1.04 g, 977 μl, 8.62 mmol), Et₃N (2.91 g, 4 ml, 28.7 mmol), bis(triphenylphosphine)palladium (II) chloride (80.6 mg, 115 μmol, 0.02 eq.), triphenylphosphine (15.1 mg, 57.4 μmol, 0.01 eq.) and copper (I) iodide (5.47 mg, 28.7 μmol, 0.005 eq.). The reaction mixture was heated to 50° C. and stirred for 2 h. The crude material was purified by flash chromatography (silica gel, 50 g, 50% to 100% EtOAc in heptane). The fractions were concentrated in vacuo to give 2.00 g of the title compound as a white powder, MS: m/e=428.2 (M+H⁺).

Step 3: (9aS)- and (9aR)-7-[2,6-difluoro-4-[2-(2-fluorophenyl)ethynyl]phenyl]-9a-methyl-2,3,4,9-tetrahydropyrazino[1,2-c]pyrimidine-1,6,8-triones

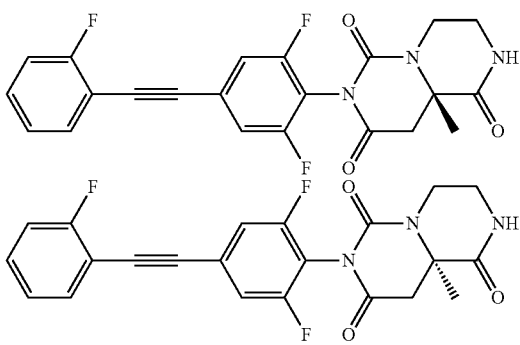

Chiral separation of the enantiomers was realized by chiral HPLC using a Chiral AD column using (heptane/EtOH—60/40) to obtain (9aS)-7-[2,6-difluoro-4-[2-(2-fluorophenyl)ethynyl]phenyl]-9a-methyl-2,3,4,9-tetrahydropyrazino[1,2-c]pyrimidine-1,6,8-trione as a light yellow solid (MS: 428.3 (M+H⁺)); and (9aR)-7-[2,6-difluoro-4-[2-(2-fluorophenyl)ethynyl]phenyl]-9a-methyl-2,3,4,9-tetrahydropyrazino[1,2-c]pyrimidine-1,6,8-trione as a light yellow solid (MS: 428.3 (M+H⁺)).

Step 4: (9aS)-7-[2,6-difluoro-4-[2-(2-fluorophenyl)ethynyl]phenyl]-9a-methyl-2-(3-pyridyl)-4,9-dihydro-3H-pyrazino[1,2-c]pyrimidine-1,6,8-trione The title compound was obtained as a white solid, MS: m/e=505.3 (M+H⁺), using chemistry similar to that described in example 5, from (9aS)-7-[2,6-difluoro-4-[2-(2-fluorophenyl)ethynyl]phenyl]-9a-methyl-2,3,4,9-tetrahydropyrazino[1,2-c]pyrimidine-1,6,8-trione (example 109, step 3) and 3-iodopyridine.

Example 110

(9aS)-7-[2,6-difluoro-4-[2-(2-fluorophenyl)ethynyl]phenyl]-9a-methyl-2-pyrimidin-4-yl-4,9-dihydro-3H-pyrazino[1,2-c]pyrimidine-1,6,8-trione

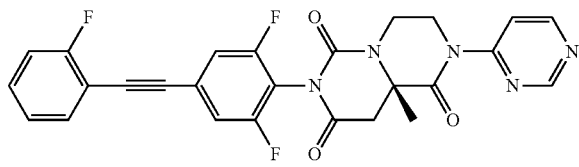 [SMILES: C[C@@]12CC(=O)N(c3c(F)cc(C#Cc4ccccc4F)cc3F)C(=O)N1CCN(c1ccncn1)C2=O]

The title compound was obtained as a light yellow solid, MS: m/e=506.2 (M+H⁺), using chemistry similar to that described in example 1, step 3; from (9aS)-7-[2,6-difluoro-4-[2-(2-fluorophenyl)ethynyl]phenyl]-9a-methyl-2,3,4,9-tetrahydropyrazino[1,2-c]pyrimidine-1,6,8-trione (example 109, step 3) and 4-bromopyrimidine hydrochloride.

Example 111

(9aS)-7-[2,6-difluoro-4-[2-(2-fluorophenyl)ethynyl]phenyl]-9a-methyl-2-(1-methylpyrazol-4-yl)-4,9-dihydro-3H-pyrazino[1,2-c]pyrimidine-1,6,8-trione

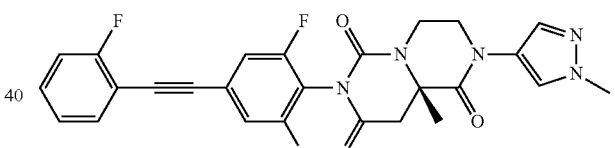

The title compound was obtained as a light yellow crystalline solid, MS: m/e=508.3 (M+H⁺), using chemistry similar to that described in example 5, from (9aS)-7-[2,6-difluoro-4-[2-(2-fluorophenyl)ethynyl]phenyl]-9a-methyl-2,3,4,9-tetrahydropyrazino[1,2-c]pyrimidine-1,6,8-trione (example 109, step 3) and 4-iodo-1-methyl-1H-pyrazole.

Example 112

(9aS)-7-[2-chloro-4-(2-phenylethynyl)phenyl]-9a-methyl-2-(1-methylpyrazol-4-yl)-4,9-dihydro-3H-pyrazino[1,2-c]pyrimidine-1,6,8-trione

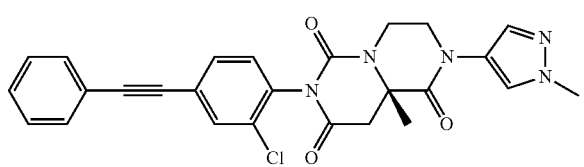 [SMILES: Cn1cc(N2CCN3C(=O)N(c4ccc(C#Cc5ccccc5)cc4Cl)C(=O)C[C@@]3(C)C2=O)cn1]

Step 1: 2-chloro-4-phenylethynyl-phenylamine

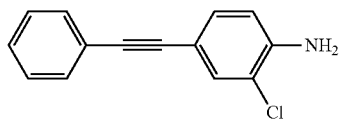

The title compound was obtained as a light brown solid, MS: m/e=228.1, 230.0 (M+H⁺), using chemistry similar to that described in example 1, step 1 from 2-chloro-4-iodoaniline and phenylacetylene.

Step 2: (9aRS)-7-[2-chloro-4-(2-phenylethynyl)phenyl]-9a-methyl-2,3,4,9-tetrahydropyrazino[1,2-c]pyrimidine-1,6,8-trione

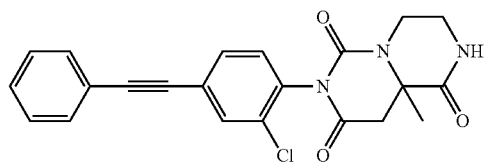 [SMILES: CC12CC(=O)N(c3ccc(C#Cc4ccccc4)cc3Cl)C(=O)N1CCNC2=O]

The title compound was obtained as a white solid, MS: m/e=406.3, 408.2 (M+H⁺), using chemistry similar to that described in Example 1, step 2 from 2-chloro-4-phenylethynyl-phenylamine (Example 112, step 1) and methyl 2-[(2RS)-2-methyl-3-oxo-piperazin-2-yl]acetate.

Step 3: (9aS)- and (9aR)-7-[2-chloro-4-(2-phenylethynyl)phenyl]-9a-methyl-2,3,4,9-tetrahydropyrazino[1,2-c]pyrimidine-1,6,8-triones

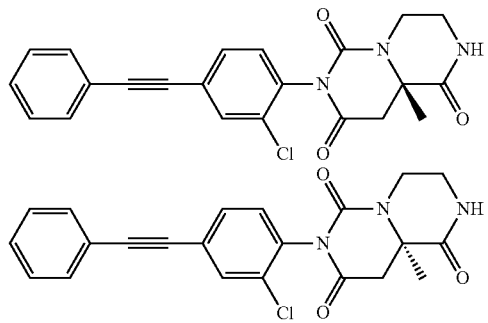

Chiral separation of the enantiomers was realized by chiral HPLC using a Reprosil Chiral NR column using (heptane/EtOH—60/40) to obtain (9aS)-7-[2-chloro-4-(2-phenylethynyl)phenyl]-9a-methyl-2,3,4,9-tetrahydropyrazino[1,2-c]pyrimidine-1,6,8-trione as a white solid (MS: 428.3 (M+H⁺)); and (9aR)-7-[2-chloro-4-(2-phenylethynyl)phenyl]-9a-methyl-2,3,4,9-tetrahydropyrazino[1,2-c]pyrimidine-1,6,8-trione as a white solid (MS: 428.3 (M+H⁺)).

Step 4: (9aS)-7-[2-chloro-4-(2-phenylethynyl)phenyl]-9a-methyl-2-(1-methylpyrazol-4-yl)-4,9-dihydro-3H-pyrazino[1,2-c]pyrimidine-1,6,8-trione The title compound was obtained as an off-white solid, MS: m/e=488.2, 490.2 (M+H⁺), using chemistry similar to that described in example 5, from (9aS)-7-[2-chloro-4-(2-phenylethynyl)phenyl]-9a-methyl-2,3,4,9-tetrahydropyrazino[1,2-c]pyrimidine-1,6,8-trione (Example 112, step 3) and 4-iodo-1-methyl-1H-pyrazole.

We claim:
1. A compound of formula I

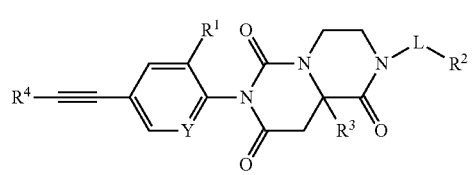

wherein
R¹ is hydrogen, F or Cl;
L is a bond or lower alkylene;
R² is —(CH₂)ₙO-lower alkyl, lower alkyl substituted by halogen, —(CH₂)ₙC(O)O-lower alkyl, phenyl substituted by lower alkyl or halogen, or is a 5 or 6-membered heteroaryl group, selected from pyridinyl, pyrimidinyl, pyridazinyl, thiazolyl, imidazolyl, pyrazolyl or triazolyl, which are optionally substituted by lower alkyl, halogen, lower alkoxy, =O, benzyloxy, cycloalkyloxy, hydroxy, cyano, lower alkyl substituted by halogen, or by —(CH₂)ₙO-lower alkyl;
n is 1, 2 or 3;
R³ is hydrogen, lower alkyl or —(CH₂)ₙO-lower alkyl;
R⁴ is phenyl, pyridinyl or pyrimidinyl, each optionally substituted by F;
Y is CF or CCl;
or a pharmaceutically acceptable salt or acid addition salt, a racemic mixture, or its corresponding enantiomer and/or optical isomer and/or stereoisomers thereof.

2. The compound of formula Ia according to claim 1,

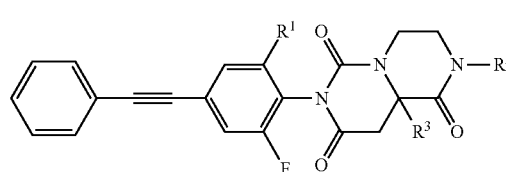

wherein
R¹ is F or Cl;
R² is —(CH₂)ₙO-lower alkyl, lower alkyl substituted by halogen or —(CH₂)ₙC(O)O-lower alkyl,
n is 1, 2 or 3;
R³ hydrogen, lower alkyl or —(CH₂)ₙO-lower alkyl;
or a pharmaceutically acceptable salt or acid addition salt, a racemic mixture, or its corresponding enantiomer and/or optical isomer and/or stereoisomers thereof.

3. The compound of formula Ia according to claim 1, wherein said compound is:
(9aS)-7-[2,6-difluoro-4-(2-phenylethynyl)phenyl]-2-(2-methoxyethyl)-9a-methyl-4,9-dihydro-3H-pyrazino[1,2-c]pyrimidine-1,6,8-trione;
(9aS)-7-[2,6-difluoro-4-(2-phenylethynyl)phenyl]-2-(3-methoxypropyl)-9a-methyl-4,9-dihydro-3H-pyrazino[1,2-c]pyrimidine-1,6,8-trione;

(9aS)-7-[2,6-difluoro-4-(2-phenylethynyl)phenyl]-9a-methyl-2-(2,2,2-trifluoroethyl)-4,9-dihydro-3H-pyrazino[1,2-c]pyrimidine-1,6,8-trione; or, Ethyl 4-[(9aS)-7-[2,6-difluoro-4-(2-phenylethynyl)phenyl]-9a-methyl-1,6,8-trioxo-4,9-dihydro-3H-pyrazino[1,2-c]pyrimidin-2-yl]butanoate.

4. The compound of formula Ib according to claim 1

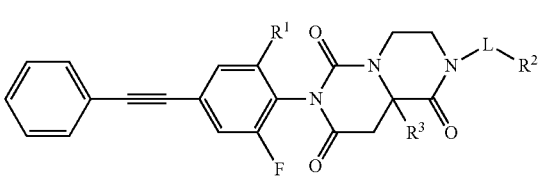

wherein
$R^1$ is F or Cl;
L is lower alkylene;
$R^2$ is phenyl substituted by lower alkyl or by halogen;
$R^3$ hydrogen, lower alkyl or —$(CH_2)_n$O-lower alkyl;
n is 1, 2 or 3;
or a pharmaceutically acceptable salt or acid addition salt, a racemic mixture, or its corresponding enantiomer and/or optical isomer and/or stereoisomers thereof.

5. The compound of formula Ib according to claim 4, wherein said compound is:
(9aRS)-7-[2,6-difluoro-4-(2-phenylethynyl)phenyl]-9a-methyl-2-(m-tolylmethyl)-4,9-dihydro-3H-pyrazino[1,2-c]pyrimidine-1,6,8-trione;
(9aRS)-7-[2,6-difluoro-4-(2-phenylethynyl)phenyl]-9a-methyl-2-(p-tolylmethyl)-4,9-dihydro-3H-pyrazino[1,2-c]pyrimidine-1,6,8-trione;
(9aRS)-7-[2,6-difluoro-4-(2-phenylethynyl)phenyl]-9a-methyl-2-(o-tolylmethyl)-4,9-dihydro-3H-pyrazino[1,2-c]pyrimidine-1,6,8-trione;
(9aRS)-7-[2,6-difluoro-4-(2-phenylethynyl)phenyl]-2-[(2,6-dimethylphenyl)methyl]-9a-methyl-4,9-dihydro-3H-pyrazino[1,2-c]pyrimidine-1,6,8-trione;
(9aRS)-2-[(2-chlorophenyl)methyl]-7-[2,6-difluoro-4-(2-phenylethynyl)phenyl]-9a-methyl-4,9-dihydro-3H-pyrazino[1,2-c]pyrimidine-1,6,8-trione;
(9aRS)-2-[(3-chlorophenyl)methyl]-7-[2,6-difluoro-4-(2-phenylethynyl)phenyl]-9a-methyl-4,9-dihydro-3H-pyrazino[1,2-c]pyrimidine-1,6,8-trione;
(9aS)-7-[2,6-difluoro-4-(2-phenylethynyl)phenyl]-2-[(2-fluorophenyl)methyl]-9a-methyl-4,9-dihydro-3H-pyrazino[1,2-c]pyrimidine-1,6,8-trione;
(9aS)-7-[2,6-difluoro-4-(2-phenylethynyl)phenyl]-2-[(3-fluorophenyl)methyl]-9a-methyl-4,9-dihydro-3H-pyrazino[1,2-c]pyrimidine-1,6,8-trione; or,
(9aS)-7-[2,6-difluoro-4-(2-phenylethynyl)phenyl]-2-[(4-fluorophenyl)methyl]-9a-methyl-4,9-dihydro-3H-pyrazino[1,2-c]pyrimidine-1,6,8-trione.

6. The compound of formula I according to claim 1

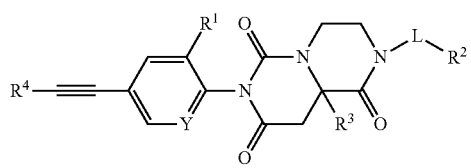

wherein
$R^1$ is hydrogen, F or Cl;
L is a bond or lower alkylene;
$R^2$ is a 5 or 6-membered heteroaryl group, selected from pyridinyl, pyrimidinyl, pyridazinyl, thiazolyl, imidazolyl, pyrazolyl or triazolyl, which are optionally substituted by lower alkyl, halogen, lower alkoxy, =O, benzyloxy, cycloalkyloxy, hydroxy, cyano, lower alkyl substituted by halogen, or by —$(CH_2)_n$O-lower alkyl;
n is 1, 2 or 3;
$R^3$ is hydrogen, lower alkyl or —$(CH_2)_n$O-lower alkyl;
$R^4$ is phenyl, pyridinyl or pyrimidinyl, each optionally substituted by F;
Y is CF or CCl;
or a pharmaceutically acceptable salt or acid addition salt, a racemic mixture, or its corresponding enantiomer and/or optical isomer and/or stereoisomers thereof.

7. The compound of formula I according to claim 1, wherein said compound is:
(9aRS)-7-[2,6-difluoro-4-(2-phenylethynyl)phenyl]-2-(3-pyridyl)-3,4,9,9a-tetrahydropyrazino[1,2-c]pyrimidine-1,6,8-trione;
(9aRS)-7-[2,6-difluoro-4-(2-phenylethynyl)phenyl]-2-pyrimidin-4-yl-3,4,9,9a-tetrahydropyrazino[1,2-c]pyrimidine-1,6,8-trione;
(9aRS)-7-[2,6-difluoro-4-(2-phenylethynyl)phenyl]-2-(2-pyridyl)-3,4,9,9a-tetrahydropyrazino[1,2-c]pyrimidine-1,6,8-trione;
(9aRS)-7-[2,6-difluoro-4-(2-phenylethynyl)phenyl]-9a-methyl-2-(2-pyridyl)-4,9-dihydro-3H-pyrazino[1,2-c]pyrimidine-1,6,8-trione;
(9aS)-7-[2,6-difluoro-4-(2-phenylethynyl)phenyl]-9a-methyl-2-(2-pyridyl)-4,9-dihydro-3H-pyrazino[1,2-c]pyrimidine-1,6,8-trione;
(9aRS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione;
(9aS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione;
(9aRS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione;
(9aS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione;
(9aRS)-7-[2,6-difluoro-4-(2-phenylethynyl)phenyl]-9a-methyl-2-(6-methyl-2-pyridyl)-4,9-dihydro-3H-pyrazino[1,2-c]pyrimidine-1,6,8-trione;
(9aRS)-7-[2,6-difluoro-4-(2-phenylethynyl)phenyl]-9a-methyl-2-(2-methyl-4-pyridyl)-4,9-dihydro-3H-pyrazino[1,2-c]pyrimidine-1,6,8-trione;
(9aRS)-7-(2,6-difluoro-4-(phenylethynyl)phenyl)-9a-methyl-2-(4-methylpyridin-2-yl)tetrahydro-1H-pyrazino[1,2-c]pyrimidine-1,6,8(2H,7H)-trione;
(9aS)-7-[2,6-difluoro-4-(2-phenylethynyl)phenyl]-9a-methyl-2-(3-pyridyl)-4,9-dihydro-3H-pyrazino[1,2-c]pyrimidine-1,6,8-trione;
(9aRS)-7-[2,6-difluoro-4-(2-phenylethynyl)phenyl]-9a-methyl-2-(5-methyl-3-pyridyl)-4,9-dihydro-3H-pyrazino[1,2-c]pyrimidine-1,6,8-trione;
(9aS)-7-[2,6-difluoro-4-(2-phenylethynyl)phenyl]-9a-methyl-2-(5-methyl-3-pyridyl)-4,9-dihydro-3H-pyrazino[1,2-c]pyrimidine-1,6,8-trione;
(9aRS)-7-[2,6-difluoro-4-(2-phenylethynyl)phenyl]-9a-methyl-2-(6-methyl-3-pyridyl)-4,9-dihydro-3H-pyrazino[1,2-c]pyrimidine-1,6,8-trione;

(9aS)-7-[2,6-difluoro-4-(2-phenylethynyl)phenyl]-2-(3,5-dimethyl-4-pyridyl)-9a-methyl-4,9-dihydro-3H-pyrazino[1,2-c]pyrimidine-1,6,8-trione;

(9aRS)-2-(2-chloro-4-pyridyl)-7-[2,6-difluoro-4-(2-phenylethynyl)phenyl]-9a-methyl-4,9-dihydro-3H-pyrazino[1,2-c]pyrimidine-1,6,8-trione;

(9aS)-2-(2-chloro-4-pyridyl)-7-[2,6-difluoro-4-(2-phenylethynyl)phenyl]-9a-methyl-4,9-dihydro-3H-pyrazino[1,2-c]pyrimidine-1,6,8-trione;

(9aRS)-2-(6-chloro-3-pyridyl)-7-[2,6-difluoro-4-(2-phenylethynyl)phenyl]-9a-methyl-4,9-dihydro-3H-pyrazino[1,2-c]pyrimidine-1,6,8-trione;

(9aS)-2-(6-chloro-3-pyridyl)-7-[2,6-difluoro-4-(2-phenylethynyl)phenyl]-9a-methyl-4,9-dihydro-3H-pyrazino[1,2-c]pyrimidine-1,6,8-trione;

(9aRS)-7-[2,6-difluoro-4-(2-phenylethynyl)phenyl]-2-(6-methoxy-3-pyridyl)-9a-methyl-4,9-dihydro-3H-pyrazino[1,2-c]pyrimidine-1,6,8-trione;

(9aS)-7-[2,6-difluoro-4-(2-phenylethynyl)phenyl]-2-(6-methoxy-3-pyridyl)-9a-methyl-4,9-dihydro-3H-pyrazino[1,2-c]pyrimidine-1,6,8-trione;

(9aS)-7-[2,6-difluoro-4-(2-phenylethynyl)phenyl]-9a-methyl-2-(1-methyl-6-oxo-3-pyridyl)-4,9-dihydro-3H-pyrazino[1,2-c]pyrimidine-1,6,8-trione;

(9aRS)-7-[2,6-difluoro-4-(2-phenylethynyl)phenyl]-9a-methyl-2-pyrimidin-2-yl-4,9-dihydro-3H-pyrazino[1,2-c]pyrimidine-1,6,8-trione;

(9aRS)-7-[2,6-difluoro-4-(2-phenylethynyl)phenyl]-9a-methyl-2-pyrimidin-4-yl-4,9-dihydro-3H-pyrazino[1,2-c]pyrimidine-1,6,8-trione;

(9aS)-7-[2,6-difluoro-4-(2-phenylethynyl)phenyl]-9a-methyl-2-pyrimidin-4-yl-4,9-dihydro-3H-pyrazino[1,2-c]pyrimidine-1,6,8-trione;

(9aRS)-7-[2,6-difluoro-4-(2-phenylethynyl)phenyl]-9a-methyl-2-pyrimidin-5-yl-4,9-dihydro-3H-pyrazino[1,2-c]pyrimidine-1,6,8-trione;

(9aRS)-7-[2,6-difluoro-4-(2-phenylethynyl)phenyl]-2-(2,6-dimethylpyrimidin-4-yl)-9a-methyl-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(2-methylpyrimidin-4-yl)-4,9-dihydro-3H-pyrazino[1,2-c]pyrimidine-1,6,8-trione;

(9aS)-7-[2,6-difluoro-4-(2-phenylethynyl)phenyl]-9a-methyl-2-(2-methylpyrimidin-4-yl)-4,9-dihydro-3H-pyrazino[1,2-c]pyrimidine-1,6,8-trione;

(9aRS)-7-[2,6-difluoro-4-(2-phenylethynyl)phenyl]-9a-methyl-2-pyrazin-2-yl-4,9-dihydro-3H-pyrazino[1,2-c]pyrimidine-1,6,8-trione;

(9aS)-7-[2,6-difluoro-4-(2-phenylethynyl)phenyl]-9a-methyl-2-pyrazin-2-yl-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(6-methylpyrazin-2-yl)-4,9-dihydro-3H-pyrazino[1,2-c]pyrimidine-1,6,8-trione;

(9aS)-7-[2,6-difluoro-4-(2-phenylethynyl)phenyl]-9a-methyl-2-(6-methylpyrimidin-4-yl)-4,9-dihydro-3H-pyrazino[1,2-c]pyrimidine-1,6,8-trione;

(9aS)-7-[2,6-difluoro-4-(2-phenylethynyl)phenyl]-9a-methyl-2-(5-methylpyrimidin-4-yl)-4,9-dihydro-3H-pyrazino[1,2-c]pyrimidine-1,6,8-trione;

(9aS)-7-[2,6-difluoro-4-(2-phenylethynyl)phenyl]-2-(2-methoxypyrimidin-5-yl)-9a-methyl-4,9-dihydro-3H-pyrazino[1,2-c]pyrimidine-1,6,8-trione (9aS)-2-(2-tert-butoxypyrimidin-5-yl)-7-[2,6-difluoro-4-(2-phenylethynyl)phenyl]-9a-methyl-4,9-dihydro-3H-pyrazino[1,2-c]pyrimidine-1,6,8-trione (9aS or 9aR)-7-[2,6-difluoro-4-(2-phenylethynyl)phenyl]-2-(2-ethoxypyrimidin-5-yl)-9a-methyl-4,9-dihydro-3H-pyrazino[1,2-c]pyrimidine-1,6,8-trione (9aS)-7-[2,6-difluoro-4-(2-phenylethynyl)phenyl]-2-(2-isopropoxypyrimidin-5-yl)-9a-methyl-4,9-dihydro-3H-pyrazino[1,2-c]pyrimidine-1,6,8-trione;

(9aS)-2-(2-benzyloxypyrimidin-5-yl)-7-[2,6-difluoro-4-(2-phenylethynyl)phenyl]-9a-methyl-4,9-dihydro-3H-pyrazino[1,2-c]pyrimidine-1,6,8-trione;

(9aS)-7-[2,6-difluoro-4-(2-phenylethynyl)phenyl]-2-(2-hydroxypyrimidin-5-yl)-9a-methyl-4,9-dihydro-3H-pyrazino[1,2-c]pyrimidine-1,6,8-trione;

(9aS)-2-[2-(cyclopropoxy)pyrimidin-5-yl]-7-[2,6-difluoro-4-(2-phenylethynyl)phenyl]-9a-methyl-4,9-dihydro-3H-pyrazino[1,2-c]pyrimidine-1,6,8-trione;

(9aS)-7-[2,6-difluoro-4-(2-phenylethynyl)phenyl]-2-(5-methoxypyrazin-2-yl)-9a-methyl-4,9-dihydro-3H-pyrazino[1,2-c]pyrimidine-1,6,8-trione;

(9aS)-2-(5-benzyloxypyrazin-2-yl)-7-[2,6-difluoro-4-(2-phenylethynyl)phenyl]-9a-methyl-4,9-dihydro-3H-pyrazino[1,2-c]pyrimidine-1,6,8-trione;

(9aRS)-7-[2,6-difluoro-4-(2-phenylethynyl)phenyl]-9a-methyl-2-pyridazin-3-yl-4,9-dihydro-3H-pyrazino[1,2-c]pyrimidine-1,6,8-trione;

(9aS)-7-[2,6-difluoro-4-(2-phenylethynyl)phenyl]-9a-methyl-2-pyrazin-2-yl-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(6-methylpyridazin-3-yl)-4,9-dihydro-3H-pyrazino[1,2-c]pyrimidine-1,6,8-trione;

(9aS)-7-[2,6-difluoro-4-(2-phenylethynyl)phenyl]-9a-methyl-2-(1-methyl-6-oxo-pyridazin-3-yl)-4,9-dihydro-3H-pyrazino[1,2-c]pyrimidine-1,6,8-trione;

(9aS)-7-[2,6-difluoro-4-(2-phenylethynyl)phenyl]-9a-methyl-2-pyridazin-4-yl-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(1-methyl-6-oxo-pyridazin-4-yl)-4,9-dihydro-3H-pyrazino[1,2-c]pyrimidine-1,6,8-trione;

(9aRS)-7-[2,6-difluoro-4-(2-phenylethynyl)phenyl]-9a-methyl-2-thiazol-2-yl-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(5-methylthiazol-2-yl)-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(4-methylthiazol-2-yl)-4,9-dihydro-3H-pyrazino[1,2-c]pyrimidine-1,6,8-trione;

2-[(9aRS)-7-[2,6-difluoro-4-(2-phenylethynyl)phenyl]-9a-methyl-1,6,8-trioxo-4,9-dihydro-3H-pyrazino[1,2-c]pyrimidin-2-yl]thiazole-4-carbonitrile;

(9aRS)-7-[2,6-difluoro-4-(2-phenylethynyl)phenyl]-9a-methyl-2-[4-(trifluoromethyl)thiazol-2-yl]-4,9-dihydro-3H-pyrazino[1,2-c]pyrimidine-1,6,8-trione;

(9aRS)-7-[2,6-difluoro-4-(2-phenylethynyl)phenyl]-9a-methyl-2-[5-(trifluoromethyl)thiazol-2-yl]-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(1-methylimidazol-4-yl)-4,9-dihydro-3H-pyrazino[1,2-c]pyrimidine-1,6,8-trione;

(9aRS)-7-[2,6-difluoro-4-(2-phenylethynyl)phenyl]-2-(1,4-dimethylimidazol-2-yl)-9a-methyl-4,9-dihydro-3H-pyrazino[1,2-c]pyrimidine-1,6,8-trione;

(9aRS)-7-[2,6-difluoro-4-(2-phenylethynyl)phenyl]-2-(1,2-dimethylimidazol-4-yl)-9a-methyl-4,9-dihydro-3H-pyrazino[1,2-c]pyrimidine-1,6,8-trione;

(9aS)-7-[2,6-difluoro-4-(2-phenylethynyl)phenyl]-9a-methyl-2-[2-methyl-1-(2,2,2-trifluoroethyl)imidazol-4-yl]-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(1-methylpyrazol-3-yl)-4,9-dihydro-3H-pyrazino[1,2-c]pyrimidine-1,6,8-trione;

(9aS)-7-[2,6-difluoro-4-(2-phenylethynyl)phenyl]-9a-methyl-2-(1-methylpyrazol-3-yl)-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(2-methylpyrazol-3-yl)-4,9-dihydro-3H-pyrazino[1,2-c]pyrimidine-1,6,8-trione;

(9aS)-7-[2,6-difluoro-4-(2-phenylethynyl)phenyl]-9a-methyl-2-(2-methylpyrazol-3-yl)-4,9-dihydro-3H-pyrazino[1,2-c]pyrimidine-1,6,8-trione;

(9aRS)-7-[2,6-difluoro-4-(2-phenylethynyl)phenyl]-2-(2,5-dimethylpyrazol-3-yl)-9a-methyl-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(1-methylpyrazol-4-yl)-4,9-dihydro-3H-pyrazino[1,2-c]pyrimidine-1,6,8-trione;

(9aS)-7-[2,6-difluoro-4-(2-phenylethynyl)phenyl]-9a-methyl-2-(1-methylpyrazol-4-yl)-4,9-dihydro-3H-pyrazino[1,2-c]pyrimidine-1,6,8-trione;

(9aS)-7-[2,6-difluoro-4-(2-phenylethynyl)phenyl]-2-(1-ethylpyrazol-4-yl)-9a-methyl-4,9-dihydro-3H-pyrazino[1,2-c]pyrimidine-1,6,8-trione;

(9aS)-7-[2,6-difluoro-4-(2-phenylethynyl)phenyl]-2-(1-isopropylpyrazol-4-yl)-9a-methyl-4,9-dihydro-3H-pyrazino[1,2-c]pyrimidine-1,6,8-trione;

(9aS)-7-[2,6-difluoro-4-(2-phenylethynyl)phenyl]-9a-methyl-2-(1H-pyrazol-4-yl)-4,9-dihydro-3H-pyrazino[1,2-c]pyrimidine-1,6,8-trione;

(9aS)-7-[2,6-difluoro-4-(2-phenylethynyl)phenyl]-2-[1-(3-methoxypropyl)pyrazol-4-yl]-9a-methyl-4,9-dihydro-3H-pyrazino[1,2-c]pyrimidine-1,6,8-trione;

(9aS)-7-[2,6-difluoro-4-(2-phenylethynyl)phenyl]-9a-methyl-2-(1-methyl-1,2,4-triazol-3-yl)-4,9-dihydro-3H-pyrazino[1,2-c]pyrimidine-1,6,8-trione;

(9aRS)-7-[2-chloro-6-fluoro-4-(2-phenylethynyl)phenyl]-9a-methyl-2-(3-pyridyl)-4,9-dihydro-3H-pyrazino[1,2-c]pyrimidine-1,6,8-trione;

(9aRS)-7-[2-chloro-6-fluoro-4-(2-phenylethynyl)phenyl]-9a-methyl-2-(4-pyridyl)-4,9-dihydro-3H-pyrazino[1,2-c]pyrimidine-1,6,8-trione;

(9aRS)-7-[2-chloro-6-fluoro-4-(2-phenylethynyl)phenyl]-9a-methyl-2-(2-pyridyl)-4,9-dihydro-3H-pyrazino[1,2-c]pyrimidine-1,6,8-trione;

(9aRS)-7-[2-chloro-6-fluoro-4-(2-phenylethynyl)phenyl]-9a-methyl-2-(4-pyridyl)-4,9-dihydro-3H-pyrazino[1,2-c]pyrimidine-1,6,8-trione;

(9aS)-7-[2-chloro-6-fluoro-4-(2-phenylethynyl)phenyl]-9a-methyl-2-(4-pyridyl)-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(2-pyridylmethyl)-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(3-pyridylmethyl)-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(4-pyridylmethyl)-4,9-dihydro-3H-pyrazino[1,2-c]pyrimidine-1,6,8-trione;

(9aRS)-7-[2,6-difluoro-4-(2-phenylethynyl)phenyl]-9a-methyl-2-(pyrimidin-4-ylmethyl)-4,9-dihydro-3H-pyrazino[1,2-c]pyrimidine-1,6,8-trione;

(9aRS)-7-[2,6-difluoro-4-(2-phenylethynyl)phenyl]-9a-methyl-2-[(1-methylpyrazol-4-yl)methyl]-4,9-dihydro-3H-pyrazino[1,2-c]pyrimidine-1,6,8-trione;

(9aS)-7-[2,6-difluoro-4-(2-phenylethynyl)phenyl]-9a-methyl-2-[(2-methylpyrazol-3-yl)methyl]-4,9-dihydro-3H-pyrazino[1,2-c]pyrimidine-1,6,8-trione;

(9aS)-7-[2,6-difluoro-4-(2-phenylethynyl)phenyl]-2-(2-imidazol-1-ylethyl)-9a-methyl-4,9-dihydro-3H-pyrazino[1,2-c]pyrimidine-1,6,8-trione;

(9aS)-7-[2,6-difluoro-4-(2-phenylethynyl)phenyl]-9a-methyl-2-[2-(2-methylimidazol-1-yl)ethyl]-4,9-dihydro-3H-pyrazino[1,2-c]pyrimidine-1,6,8-trione;

(9aS)-7-[2,6-difluoro-4-(2-phenylethynyl)phenyl]-9a-methyl-2-[2-(2-methylpyrazol-3-yl)ethyl]-4,9-dihydro-3H-pyrazino[1,2-c]pyrimidine-1,6,8-trione;

(9aS)-7-[2,6-difluoro-4-(2-phenylethynyl)phenyl]-9a-methyl-2-[2-(1-methylpyrazol-4-yl)ethyl]-4,9-dihydro-3H-pyrazino[1,2-c]pyrimidine-1,6,8-trione;

(9aRS)-7-[2,6-difluoro-4-(2-phenylethynyl)phenyl]-9a-(methoxymethyl)-2-(3-pyridyl)-4,9-dihydro-3H-pyrazino[1,2-c]pyrimidine-1,6,8-trione;

(9aR)-7-[2,6-difluoro-4-(2-phenylethynyl)phenyl]-9a-(methoxymethyl)-2-(3-pyridyl)-4,9-dihydro-3H-pyrazino[1,2-c]pyrimidine-1,6,8-trione;

(9aRS)-7-[2,6-difluoro-4-(2-phenylethynyl)phenyl]-9a-(methoxymethyl)-2-(1-methylpyrazol-4-yl)-4,9-dihydro-3H-pyrazino[1,2-c]pyrimidine-1,6,8-trione;

(9aR)-7-[2,6-difluoro-4-(2-phenylethynyl)phenyl]-9a-(methoxymethyl)-2-(1-methylpyrazol-4-yl)-4,9-dihydro-3H-pyrazino[1,2-c]pyrimidine-1,6,8-trione;

(9aS)-7-[2,6-difluoro-4-(2-phenylethynyl)phenyl]-9a-ethyl-2-(3-pyridyl)-4,9-dihydro-3H-pyrazino[1,2-c]pyrimidine-1,6,8-trione;

(9aS)-7-[2,6-difluoro-4-(2-phenylethynyl)phenyl]-9a-ethyl-2-(1-methylpyrazol-4-yl)-4,9-dihydro-3H-pyrazino[1,2-c]pyrimidine-1,6,8-trione;

(9aRS)-7-[2-fluoro-4-(2-phenylethynyl)phenyl]-9a-methyl-2-(3-pyridyl)-4,9-dihydro-3H-pyrazino[1,2-c]pyrimidine-1,6,8-trione;

(9aS)-7-[2,6-difluoro-4-[2-(2-fluorophenyl)ethynyl]phenyl]-9a-methyl-2-(3-pyridyl)-4,9-dihydro-3H-pyrazino[1,2-c]pyrimidine-1,6,8-trione;

(9aS)-7-[2,6-difluoro-4-[2-(2-fluorophenyl)ethynyl]phenyl]-9a-methyl-2-pyrimidin-4-yl-4,9-dihydro-3H-pyrazino[1,2-c]pyrimidine-1,6,8-trione;

(9aS)-7-[2,6-difluoro-4-[2-(2-fluorophenyl)ethynyl]phenyl]-9a-methyl-2-(1-methylpyrazol-4-yl)-4,9-dihydro-3H-pyrazino[1,2-c]pyrimidine-1,6,8-trione; or, (9aS)-7-[2-chloro-4-(2-phenylethynyl)phenyl]-9a-methyl-2-(1-methylpyrazol-4-yl)-4,9-dihydro-3H-pyrazino[1,2-c]pyrimidine-1,6,8-trione.

8. A process for the preparation of a compound of formula I according to claim 1 which process comprises:

(a) the step of reacting a compound of formula IV

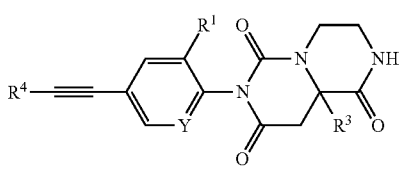

with a compound of formula $XLR^2$, wherein X is halogen, to afford a compound of formula I

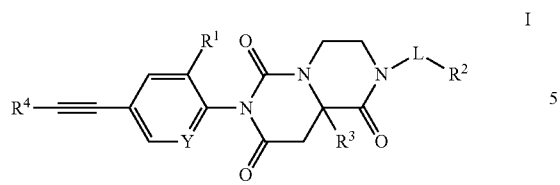

and, (b) if desired, converting the compounds obtained into pharmaceutically acceptable acid addition salts.

9. A pharmaceutical composition comprising a compound of formula I according to claim 1 and at least one pharmaceutically acceptable excipients.

10. A method for the treatment of Parkinson's disease, anxiety, emesis, obsessive compulsive disorder, autism, neuroprotection, depression and diabetes type 2, which method comprises administering a therapeutically effective amount of a compound of formula I according to claim 1 to a patient in need thereof.

* * * * *